US007794956B2

(12) United States Patent
Feng et al.

(10) Patent No.: US 7,794,956 B2
(45) Date of Patent: Sep. 14, 2010

(54) GAB1 INVOLVEMENT IN GLUCOSE HOMEOSTASIS REGULATION BY HEPATOCYTES

(75) Inventors: Gen-Sheng Feng, San Diego, CA (US); Emilie Chapeau, San Diego, CA (US)

(73) Assignee: Sanford-Burnham Medical Research Institute, La Jolla, CA (US)

(*) Notice: Subject to any disclaimer, the term of this patent is extended or adjusted under 35 U.S.C. 154(b) by 757 days.

(21) Appl. No.: 10/987,384

(22) Filed: Nov. 12, 2004

(65) Prior Publication Data

US 2005/0183144 A1 Aug. 18, 2005

Related U.S. Application Data

(60) Provisional application No. 60/519,358, filed on Nov. 12, 2003.

(51) Int. Cl.
*G01N 33/567* (2006.01)
*C12Q 1/00* (2006.01)
*C12N 5/02* (2006.01)

(52) U.S. Cl. .......................... 435/7.21; 435/4; 435/325

(58) Field of Classification Search ....................... None
See application file for complete search history.

(56) References Cited

U.S. PATENT DOCUMENTS 6,133,428 A * 10/2000 Wong et al. ............ 530/388.24

OTHER PUBLICATIONS

Harada et al. Grb-2-Associated Binder-1 Is Involved in Insulin-Induced egr-1 Gene Expression through its Phosphatidylinositol 3'-Kinase Binding Site. DNA and Cell Biology, 20(4): 223-229, 2001.*

Sesti et al. Defects of the insulin receptor substrate (IRS) system in human metabolic disorders. FASEB, 15: 2099-2111, 2001.*

Doman et al . Molecular docking and high-throughput screening for novel inhibitors of protein tyrosine phosphatase-1B. J. Med. Chem. 43: 2213-2221, 2002.*

Boess et al. Gene expression in two hepatic cell lines, cultured primary hepatocytes, and liver slices compared to the in vivo liver gene expression in rats: possible implications for toxicogenomics use of in vitro systems. Toxicological Sciences 73: 386-402, 2003.*

Gomez et al. Acute effect of different antidepressants on glycemia in diabetic and non-diabetic rats. Brazilian J. of Medical and Biological Res. 34: 57-64, 2001.*

Buchholz et al., Nucl. Acids Res, "Different thermostabilites of FLP and Cre recombinases: implications for applied site-specific recombination" 24(21), 4256-4262 (1996).

Buchholz, et al., Nature, "Imporved properites of FLP recombinase evolved by cycling mutagenesis" 16, 657-662 (1998).

De Fea, K., and Roth, R., Biochemistry, "Protein Kinase C Modulation of Insulin Receptor Substrate-1 Tyrosine Phosphorylation Requires Serine 612" 36, 12939-12947 (1997).

De Fea, K., and Roth, R., J Bio Chem, "Modulation of Insulin Receptor Substrate-1 Tyrosine Phosphorylation and Function by Mitogen-activated . . . " 272(50), 31400-31406 (1997).

Gu, H. and Neel, B., Trends in Cell Biology "The "Gab" in signal transduction" 13(3), 122-130 (2003).

Holgado-Madruga, M., et al., Nature, "A Grb2-associated docking protein in EGF- and insulin-receptor signaling" 379, 560-564 (1996).

Itoh M., et al., Mol Cell Bio., "Role of Gabl in Heart, Placenta, and Skin . . . " 20 (10), 3695-3704 (2000).

Kahn, B., and Rossetti, L., Nature Genetics, "Type 2 Diabetes—who is conducting the orchestra?" 20, 223-225 (1998).

Michael, M., Mol. Cell., "Loss of Insulin Signaling in Hepatocytes Leads to Severe Insulin Resistance and Progressive Hepatic Dysfunction" 6, 87-97 (2000).

Ruff, S., et al., J Bio Chem, "Peroxovanadate Induces Tyrosine Phosphorylation of Multiple Signaling Proteins in Mouse Liver and Kidney" 272 (2) 1263-1267 (1997).

Sachs, M., et al., J Cell Bio, "Essential role of Gab1 for Signaling by the c-Met Receptor in Vivo" 150 (6) 1375-1384 (2000).

Satiel A., and Kahn, R., Nature, "Insulin signaling and the regulation of glucose and lipid metabolism" 414, 799-806 (2001).

Shui, W., and Tan, T., Genesis, "Germlin Transmission and Efficeint DNA Recombination in Mouse Embryonic Stem Cells Mediated by Adenoviral-Cre Transduction" 39 217-223 (2004).

Tamemoto, H., et al., Nature, "Insulin resistance and growth retardation in mice lacking insulin receptor substrate-1" 372 (10) 182-186 (1994).

Wang, X., et al., PNAS "The Forkhead Box M1b transcription factor is essential fo repatocyte DNA replication . . . " 99 (26) 16881-1686 (2002).

Withers, D., et al., Nature, "Disruption of IRS-2 causes type 2 diabetes in mice" 391, 900-904 (1998).

Arakl, E., et al., Nature, "Alternative pathway of insulin signaling in mice with targeted disruption of the IRS-1 gene" 372 186-190 (1994).

* cited by examiner

*Primary Examiner*—Michele K Joike
(74) *Attorney, Agent, or Firm*—Margaret M. Dunbar

(57) ABSTRACT

The invention is directed to the regulation of glucose homeostasis by modulating the activity of Grb2-associated binder 1 (Gab1) in hepatocytes. This invention also provides for a method for identifying compounds capable of modulating the glucose homeostasis regulatory activity of Gab1. In one aspect, the invention provides a method for identifying a compound that can effectively modulate glucose homeostasis wherein Gabl mediated MapK activity indicates that the candidate compound is an effective compound that modulates glucose homeostasis. In another aspect, the invention provides a method for identifying a compound that can effectively modulate the glucose homeostasis regulating activity of Gabl wherein MAPK is activated to phosphorylate Serine residue 612 of IRS-1, indicating that the candidate compound is an effective compound that modulates glucose homeostasis. In another aspect of the invention is provided a method for diagnosing Gab1 related disorders.

16 Claims, 8 Drawing Sheets

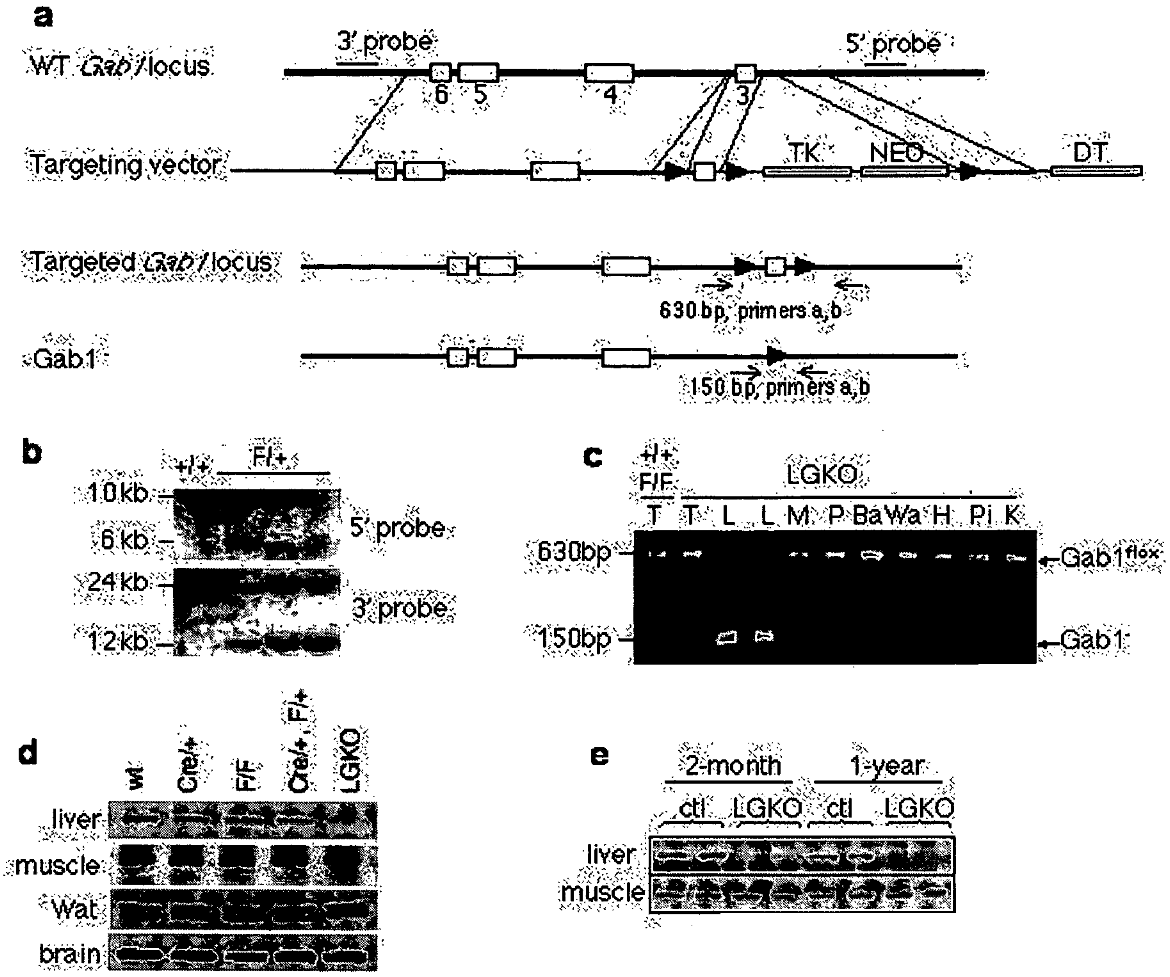
Figures 1a, 1b, 1c, 1d, and 1e.

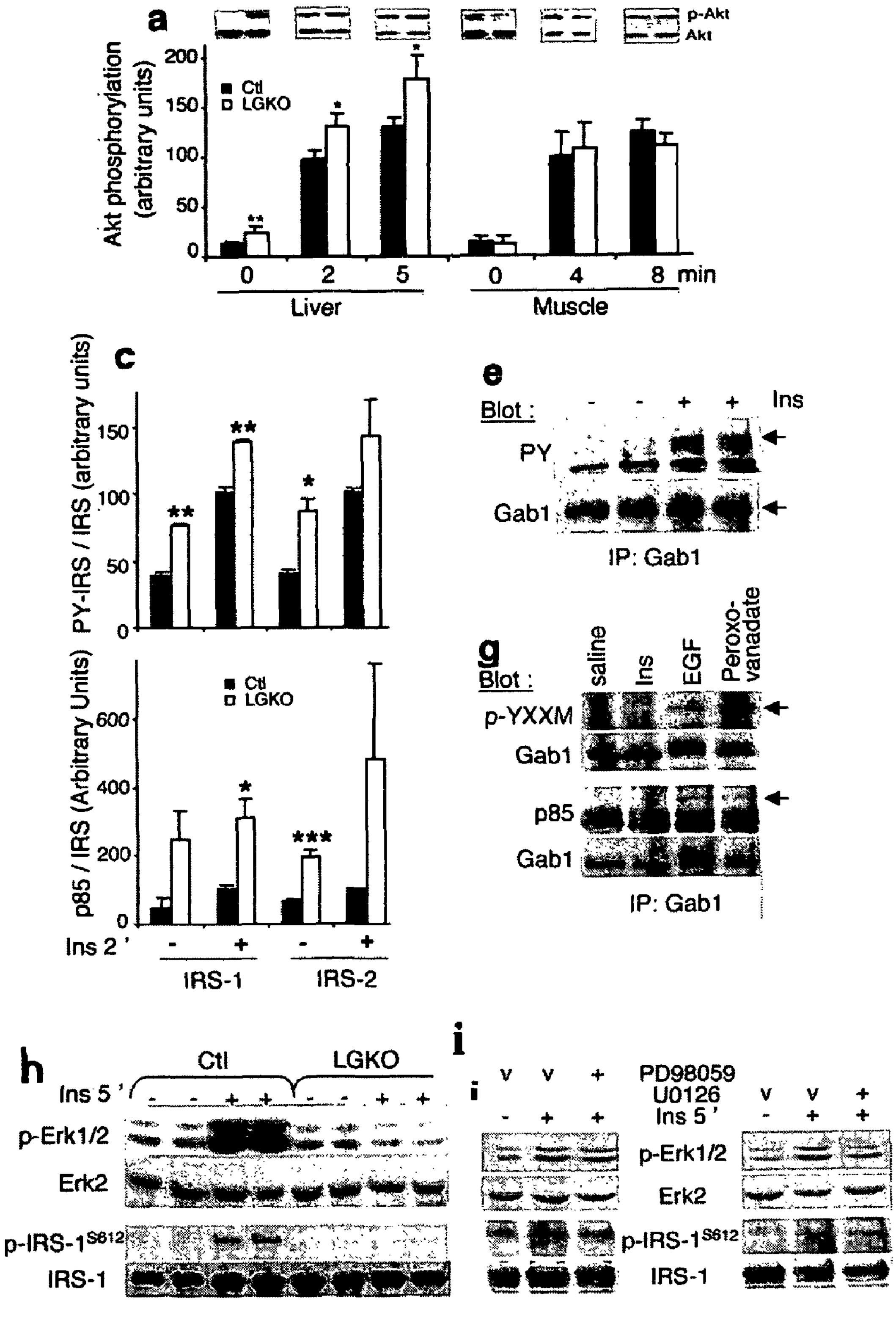
Figures 4a, 4c, 4e 4g, 4h and 4i b d f

SEQUENCE LISTING

<160> NUMBER OF SEQ ID NOS: 9

<210> SEQ ID NO 1
<211> LENGTH: 117329
<212> TYPE: DNA
<213> ORGANISM: Mouse Genome Ensemble Gene ID ENSMUSG00000031714
<220> FEATURE:
<221> NAME/KEY: misc_feature
<222> LOCATION: (4762)..(4861)
<223> OTHER INFORMATION: n is a, c, g, or t
<220> FEATURE:
<221> NAME/KEY: misc_feature
<222> LOCATION: (7022)..(7244)
<223> OTHER INFORMATION: n is a, c, g, or t
<220> FEATURE:
<221> NAME/KEY: misc_feature
<222> LOCATION: (33630)..(33729)
<223> OTHER INFORMATION: n is a, c, g, or t
<220> FEATURE:
<221> NAME/KEY: misc_feature
<222> LOCATION: (64514)..(64613)
<223> OTHER INFORMATION: n is a, c, g, or t
<220> FEATURE:
<221> NAME/KEY: misc_feature
<222> LOCATION: (74095)..(74194)
<223> OTHER INFORMATION: n is a, c, g, or t
<220> FEATURE:
<221> NAME/KEY: misc_feature
<222> LOCATION: (95358)..(95457)
<223> OTHER INFORMATION: n is a, c, g, or t
<220> FEATURE:
<221> NAME/KEY: misc_feature
<222> LOCATION: (98978)..(99077)
<223> OTHER INFORMATION: n is a, c, g, or t

<400> SEQUENCE: 1
agtggaagca gtgtgagact ttatcctgtc ttagagatac acgcagctga acgctttgtg 60
gaggctaagc ggtagcatca ctcggtagaa cagctcctgg gtcaggccct aggcacccag 120
gaggtccccc acccccttgg tctctgggtg cacagtgagg gtcctagcgc gctcctggtc 180
cgggagacgc agtccttcag tctctcgagc agccaggacc cgcttgagtg agttctcctc 240
ctggctgggt tattttttca gactgtcaag tagggaaatc cttccgaaaa ctctggatcg 300
cgaaggcaca gccgagtaca aactcctgac cctgggggtt gtcaagatgg caaactcagt 360
cggagctggc gagagtgccc ggcactcccg ctctcacact ggggtggcgc tgcgttcccg 420
gagaccgccg ccttccatag cgcgcgggcc cggggcggcg gggcggcgag gaccccagcg 480
cgcctgctga ctacagatcc cagggtgcct ctgccatctc gctccctccc agcgccggcc 540
ccgcctcccc agcccttgtt gttttggctg gaagcgctcc ggaggagttt cagagaaagt 600
ctgggctgaa gctagaggcg accgatcgtg ggaaggggag gcagaaaggc taggaggagg 660
agggccgggg cccaggccgc gcctccccga acccgccgcg cgcccccggg gtgggggagg 720
agcgcagggg acaggacaga ggggtccctc cccgaagcag agccgccctg cgcctcgtcc 780
ctgtgctgat ccccgccctc atccgaggct ggagcgcaga cccaccctcc caccgcggac 840
ccgcgacctc cccgacgccc ggcgacgccc tgaccctcgc tgctggtccg cgaactccct 900
aggctgatca ggacctgccc ctgtgccggc tgccacccgg acgccgcacg ccttcccagg 960 cgccctttc cgagcagagg gaaagagaag atcgagcccc tctcagtgtg aatgcgccaa 1020
cgggcggagc ggagcggagc ggacaccgcg cgcgggcatt gtgtgtgcgc gtgcagcgtg 1080
gggtccgcag cggggagcac ccgcgggagg tcccgtttcc aaggggcgga gcgcagggct 1140
tccagttctg ggctccctgt ccggacagag tcccagcgga gcccgaccgc tgcctaggcg 1200

-continued

```
gcgggacggc gcgcctggcg gccaggaggg cgcactgaaa gaaggtcggc gagccctggt   1260
ccccgcggtt cccgatcgag ttcctcttca gtccgcgaat ctgcgggaga ggttcgatcg   1320
ccgacacagg gcgcggggag ccgggccgcc ccgtcggggg aatctgagac gtcctctggg   1380
ctgcgtttga ctgccgtgcc cgccgtgcac ggagcgcgtc cactgtgtcc accgacccct   1440
ttggtgtctg gtcctcgagt cctcacggcg tgcaccatga gcggcggcga agtggtttgc   1500
tcgggatggc tccgcaagtc gcccccggag aagaagttga agcgttatgt aagtacaggt   1560
caggtcaccg tctgccccgc tgcagcagcc tgcgcgcccg gttggctctt ccacgaatcc   1620
cgccctcctt ttcctcgatc cgtctctcgg ccggcgggct ccggaccggg tgcggtccac   1680
tcccaccctg acgtccactc ggcggccaaa ctttctccct ccatattgca gactgcctcc   1740
cttgtaggcc tcgttgcctg ttagagaagc ccagttttcc agctcaaaac tggctgcata   1800
ctttggttgt tgttatttcc atttagcaag ggtggagtga aacagggaga aagagccttc   1860
ttttattatc tgtatcagat tctcatggag ctgttaaatc tcccctcccc gagaaaccgc   1920
ggaggtagta agtactcatg ggttctcgat tgggtccgcg cccgctctcc tttgcgcctc   1980
caggaggtgg agggaagtga actgtggacg caagaagtgg ataatatagg caaacttctc   2040
aaaatattcg ctcaagggaa aggggaaaaa agttcttatg aaccctgccg tctgcttagc   2100
attttcatgg ttttgctttg aggacactgg attttggcct gagaaccctg gcggtttgat   2160
tcggcaggag ggcgctgggg ggagcctggt ggctggtgtt tgggcgcctt agaagcgctg   2220
tcaagccccg caggagggga cagctgaagc caacagggat ttcttgatgc tggcgtttct   2280
tttcccgggc accagaacgg cttaactggt atttgcgtaa ttgattcaag atgctgattg   2340
tgagatgact gtgttcacgg ttaggaaaac tgtatcttga aggagcctat aatacttgag   2400
tggaactata tcctcatcgg gaatctaggg tcctaagtct tccttcagat tggctaattt   2460
tgcgatgtac cctgtcagta aagaaatgac actttgtacc ggcatttgaa acaagtattt   2520
ttagggtgaa atgtgtttcc caaaagcaaa acgtgtaccc acttaattag agtttactac   2580
ctgttttgat gaaacctgtt tctggtggag gggcgtctac accaagaatc atcggactac   2640
tcgcttgctt gtgtgaaacc aggcaatatt tattttcacg gagctcacca gcgagtttcg   2700
ggctcacctt ctggtataat ttaatacagc caagtaattt cattgaaaga tgtgatttga   2760
caaattgtca gaggttcccc aaagatgtct ctccatctgt cacagtttgc ttggatttct   2820
tggtaaagat ggcaacttga ttccagaaat ttgagagtgg cagtgacatc ttcagaatta   2880
gttctaaaga gacgattgtg gtgaggcgat gaggggtgag gagatagagg taaggcacta   2940
tttaggaaag acggttttag gattcttgag gaaactaaag tacaatatat ttgctgatca   3000
tgcagtccgg tgcattcttt cattacttat ggcctgccag acatactgag ttctgtacta   3060
ggcaccagcc acaaggtaag gagaaaagcc ttgcagggaa ggaaaatgac aactaataag   3120
ggacagatat ggtggtatta tatgcccaat accacccagc actccagagg cagaaatggg   3180
aggctccgtg gacaaactgg tctccatagc agattccagg ctagccagga ccgtgtctca   3240
aaaatagaaa acacaagcac aaaaaccaaa tacagctgat tatttataaa gatattaata   3300
ataatatgat tatgtttact tatatgtatc attatatgac cacagcaatg ttctcccaca   3360
aaagtcccaa tcatgccaaa cctgttagct tctgaatcag ggaagagtga ttgaattcag   3420
gggggtctgc gaaacgtgaa gctcagatta agtctaaggt cttttcagtc tagactttct   3480
gtgaattagc tgagaactca aggaagaaga accaatcgga tacacagtgc tccaaccttt   3540
```

-continued

```
gctcctaagt agtttttaaa gtttggggaa caacaaagtc ttaaagtaaa tgcagagaaa   3600
gtcagccaga atgcaaagtg gcttttatct gcatgtctac attgagtggt ggtgttttta   3660
taaatgcctt caggagaaaa ctcagtccct aaattgtgtt tcagtaagca ggaggtgggg   3720
gaagccaagg gttttcttgc ttggtagaaa actagtggtt tgtgtgtgtg tgtgtgtgtg   3780
tgtgtgtgtg tgtgtgtgtg tgtgtgtgtg tttgtgtgtg ggtatgcaca taggcatgta   3840
tgcacatgtg cgtttgtggt ggccagaggt cagcctcagg catgtcattc cagtggagct   3900
acccaccttg ctttgctcaa agggtctcac tgggatctgg ggcttatgga ttagagtcgg   3960
ctgtgggctg gttagtgaga tcaggcatcc tcctgtctct gcgtcaccag tgttggggtt   4020
ataaactgca gcagcatgct tggcttgtta caaaggagct ggggttgggc tgagtttctt   4080
gggcttctgt ggaaagcatt ttatcacgtg agccatgtct ccagctgact agtgtttctt   4140
tacagtttag tggagtaggt gaggatggcc caggatggta atagacaggt gacagccaag   4200
aggatgactg aggtctgcta agtgacactt atttgtcagg tttagtcctc agatttgaca   4260
tcctcgggat gttgaacctt tgacttgggc atccatccag tttgattttg ttaaagggat   4320
ggctacgtac gatggctatg tgtatttttc tattcttttc ctttttttctt tttttcttt   4380
ttggtgaaag gaatcctgca aagtaggcca aagaatgatt gataattttt tttgtttgtt   4440
tttgttttag tttttcgaga cagggtttct ctgtaaagcc ctggctgttc tggaactcac   4500
tttgtagacc aggctagcct cgaactcaga aatccgcctg cctctgcctt ccgagtgctg   4560
gaattaaagg cgtgcgccac cacacccggc tgataatggt ttttattttt caaattttta   4620
tgtgtgtgcc tgtgggagta gagcccaagg ccttgagccc aaggcctcac acataattcc   4680
aaatgttctg caattgagct gttttcacac ccttgacagg gcttctctct ctctctctct   4740
ctctctctct ctctctctct cnnnnnnnnn nnnnnnnnnn nnnnnnnnnn nnnnnnnnnn   4800
nnnnnnnnnn nnnnnnnnnn nnnnnnnnnn nnnnnnnnnn nnnnnnnnnn nnnnnnnnnn   4860
ntctgcttct gcctgccaag tgctgggata aaagacatgt gccaccttgc ctggcaatat   4920
ttttaaatca atatttttaa atgtcttctc ctctcctctc ctctcctctc ctctcctctc   4980
ctctcctctc ctctcctctc ctctcctctc ctctcctctc ctctcctctc ctctcctctc   5040
ctctcctctc ctctcctctc ctttcctttc ctttcctttc atgtgtgcat gtttcttatg   5100
tgtgtacatg agagtgagtg tgtgctatgg aggtcagcgg acaacttgtg ctccagagtt   5160
tgttctttcc ttcccccacg tgggtcctgc gtgagtatcc aactgtggtt gacagaagta   5220
ggggcaagtg tcttaaccct ctgggccatc tttctggcct gataatgctt tttaatgagc   5280
atattcacta tgaaaagctt atcttggatg cttgcactgt aattattaaa tgagacttca   5340
gggagtttga gtatcatcgt cctgctggga aatgctgccc gtgggacgtt gactcttgtc   5400
ttggtatttg tttgcagcat ttgtagagtg gtccaaatga ttgttaaggt ctgtaagtga   5460
caaacacaca cacacaaaca aacaaatttt tggctcaggg agatggctta atgaataaat   5520
cattttgtct catgtttgag aatgtgagaa cttgagttct gtctcccgaa ctcatgcgag   5580
taccagggca ggcatggtgg cagcctagaa tgccaactgt agggaactgt gtatactcag   5640
ggccagctgg acaattagat tagcaaactt ctatattgaa gagtgttccg gcttgctgag   5700
atggctcagt ggttaagagc attgactgct cttccaaagg tcttgagttg aaatcccagc   5760
aactacatgg tggctcacaa ccatctgtaa tggggatctg atgccctctt ctggtgtgtc   5820
taaaagacag ctacagtgta cttacatata ataatcaata aatcttaaaa aaaagaagag   5880
agtttctcca ataattgaaa tagccaatga gaaagacatc tgatgttatt gatgggcctg   5940
```

-continued

```
cgcacatatt ataaatgttc ctgcccatat gtgtgtgtcc atatacatac agacatggac   6000
atcacatgca tatgcaagaa agtattgatt tcatctttaa aactatctca agggctgggg   6060
agatggctta gcagttaaga ctgctcttcc agaggtcctg agttcaaatc ccagcaacca   6120
catgctggct cacaaccatt tgtaacaata tctgactccc tcttctagag tgtctgaaga   6180
aagctacagt gtacctagat ataagaaata aatcttaaaa agaaaaaaat ctcaaattgt   6240
ggcccctgat gagttctgta cagcccctgt tgcggtaaat ctcccaccca aataagcctg   6300
gggaatgtaa acacaatgaa tacatgctgt gcgcctagat tggcagatc tacctctacg   6360
ctatcatctt ccccatataa gagacccctt agaacttgca gtttctccag gccaggtgct   6420
ctgctccact ttccttcttt tcctcctcct ccattttgtt tgtttggttg gctggttttt   6480
tttttgtttt gttttgtttg tttgtttttg tattggtttc atctttaaaa ccagctcaaa   6540
ttgtagcccc gatgagtcct gtacagcccc aacgtctgtg tccgtatgtc cgcgtgactg   6600
ctctgtctgg tcactgtcac agcctgtttt cttccttgtc tttgtgctca tctaatagag   6660
gaactttctc tcagagaaag tgacagggga taaaggaaga gactccccag tctcagagtc   6720
acttctttgc ggacctttcc catgcaaaag ggtaagaact ttttacatgc gcagtcctgc   6780
agtctgtcct ctggcggctt tgctgagggt tatgcacagt ggggatgaac atcctcacgc   6840
tttctctcag tgttgctgag tgacctccag cgctcagtca ccagggtcat agagttgagg   6900
gaactgctat tctgtactca gctcagctcg gatttcttat taaaatttaa atttgcaggg   6960
ctggggatgg agctcagcct tgcctagtgt acaggaagtc gtgtgtgtgt gtgtgtgtgt   7020
gnnnnnnnnn nnnnnnnnnn nnnnnnnnnn nnnnnnnnnn nnnnnnnnnn nnnnnnnnnn   7080
nnnnnnnnnn nnnnnnnnnn nnnnnnnnnn nnnnnnnnnn nnnnnnnnnn nnnnnnnnnn   7140
nnnnnnnnnn nnnnnnnnnn nnnnnnnnnn nnnnnnnnnn nnnnnnnnnn nnnnnnnnnn   7200
nnnnnnnnnn nnnnnnnnnn nnnnnnnnnn nnnnnnnnnn nnnncctctg acctcaaccc   7260
aagctcctta gcacaaatac cacacacaca cacacacaca cacacaccac acaccacaca   7320
ccatacacta aaaattaaat tagtaagatc attctttttt ttgtttgttt gtttccgaga   7380
cagggtttct ctgtgtagcc ctggctgtcc tggaactctc tctgtagacc aggctggcct   7440
cgaactcaga aatccgcctg cctctggtgc tgggattaaa ggtgtgcgcc accatgcctg   7500
gctagtaaga tcattcttac tagtagagtt gaggcttgcc aaggcaacat ttttttttta   7560
aagtcttcag tgctgtctaa gcatttgggg cgacagtgtg gcgattcagt accagtacac   7620
aaaaatgtaa tggtcaggtc tgggtactta gacttctcct tacacatttt atctgtggtt   7680
tggcagccat tgaacatctc tcttgatttg taaaatacac attgtatttt cctaaggact   7740
tattttagaa agtagtggtg ggggttagca tatccagaat gcacatgaca catccatgaa   7800
aacatcaaag aacaaatgca atgaaaggtt ttgttttttt ttttaaagca atggtggact   7860
ttcccatcag gatgtgaaat tttcacagaa ataaatgtaa gtggataaat aatagcttgc   7920
ttcaatccag ctggccctca ctgctactct gcaggggtag tttccatgtg gcccgcctcc   7980
agcctgacgc ccagggaggt tcctccacag cctgctgtct gtcagctctg ggcaggtgtc   8040
ctggaggagc aggtgttcct cctcggtagg agaacctgcc tgggaagcca gggcaaggtg   8100
gcctgagagc agacagccct ggagcaaggc ctcagccagt tcttgggtgg ataatctgtc   8160
acccagcttg agctctgtct gctgcagctg tcaattatca gagcaggttt tgtctggact   8220
ttgggagcag cctctagttc aggagaggag tctctcactg ggtgggcatg cgacatctga   8280
```

-continued

```
tgtggtggag gggaacctga gcagcatctc tgtggctcaa ggatgcccta gggtgtgtgc   8340
tgatcctgaa gaccgtggtc ccactcgcct ggcctgtctc acctgtttca cattgagacc   8400
ctccagctgc cctgttgaag gacaattttc ctggttgcct tcatgttagt gaacattcac   8460
gtcagattcc tgccatctcc attccaccct ttgaagtccg gcaggaccat tgtctgttaa   8520
cacaggtctt taactagcaa tcacattaag ccttcttact tagttaatga cagttaattc   8580
ttctgttgtg cctgggcaga atggtaagtt gtataatgct ctccattaag ctcgctgaat   8640
ccctgaatac agttggtacc ttttggggat ttagaattcc tatttggaag ttaatcattt   8700
gggtggtaat ttcttaccac tttttaaccc tctaactgca ctcttctttt ctttctaaat   8760
ttgtagaacc cgaaacatgt actcactcag ctttgccaag aacagaagtt ggaagggaat   8820
ttataagctt ttcaattttt tctttctttt ctctctttgt ctctctctct ctccttcctt   8880
tctttctttc tttctttctt tctttctttc tttctttctt tctttctttc tttctttctt   8940
ccttccttcc ttccttcctt ccttccttcc ttccttcctt cctttagggt ttctctgtgt   9000
agccctggct gtcctggatg gaactcaccc tgtagaccag gctggcctcg aactcagaaa   9060
ttcacctgcc tctgcctcct gagtgctggg attaaaggcg tgaaccacca ctgcccggcc   9120
ttcaactttt ccactcttgg ggtatataca agcaaaataa ataaatgaat gaatgaatga   9180
gaggagggat aggccagtga aatggaggaa tgttcgtgcc ttttctggga ataagagatt   9240
gcttgaagaa ttcaggtgcc agttttcttt gttcgtttaa tggttctttc cagtatcgac   9300
gtggcaacta taaacggtac tgacattggg agctgtgtca tttgccgtgt agatgggatt   9360
atagaaaagc tagaggccat ctggtggtct ctctcagcca atttagatcc aaccagtttc   9420
catcttggcc agcccacctg aagaggaact gctggcattt aaaaatcctg tccttgaagg   9480
tagacaagat taggggtaga agttctagta actcaacttg gcatctgtca ggattacaga   9540
tttagaattc tgctggttta gaacaaatga ctgtcacttt cggtctgggg ctgaggctta   9600
gttgagtgag tgtctagcat gacagatgaa gctcaggctc tgtcctcaac actgggcatg   9660
gtggagaaca ccagtaatcc ctgcctttgg gaggtggagg cagaaggatc gccatattca   9720
aggtcaccag agctatacgc tttgaggtta gcattttaaa aaatatcttg tccttttaaa   9780
gaaaatagtt atgagcagga tattgtggct cagacttgta gtcttagcag ctgggaggta   9840
gaagcaggag gactgagttt gagactacat agcaagaccc ggtctcagaa tagtgaaggg   9900
tggaagtgct aaggatttca gcatgcattc tgcttgggct gtgggaggga acgcaggctg   9960
agggtcgggc tgtgcctctg gcctcccacc tgatccttga ctggtctgat cctgtttcct  10020
tatctggagg ggaggggaca gaagggcagt agagctccag ctgtggtaga gagtggggtg  10080
gggggagcat cagagggtag accgagagct actcacttgc taggctctat tgctcttctc  10140
tggtcgttgc gtgaacgtgg taggaattct gtgggctcca cagtgttact cagtgcagga  10200
gaacacagac acacagttgg cttcagtgtt cgggtgctgg gtgcacccac aagcagtacc  10260
tggctcagga tggaaggttc cacagcttat ctgctggctg agtaaataaa caggtatttc  10320
gggagctttg gtcctgggcc ttatgtggaa tgcagtgcag acacctgtcc actccctgcc  10380
tgtaaggagt ttctgatctg tgaaaaccag ctgtagcttc atgaacactt agctttcctc  10440
agagattggc tggggagctc tctgtgttta gttgccaaat gagggctcca ggttgtagtt  10500
gcctaagagt cgagactgag agagggaggg aagaggatga ccccagaaaa cttcccatca  10560
gagtctcaag ctgttccagg aaggattgag gtgcagcccc ccccctctcg gtagcaaaat  10620
cctaagggaa agatgtttta gatgaacaaa gagtccttag cagtgacacg aagggcctca  10680
```

-continued

```
ggatgctgga gctcaggcct ggggtttgca tgtcagctgt aactttctca ttggcaaagt  10740
ttttgtttct gctatgactt aataaggttc tcatgggcac ctagccacag tgtgttttcc  10800
gcaaccaaga agacagaaac acagcaaccc gtgcggtcac ctgggcttat taaaattcca  10860
agggacctgc gttagttaag atttctttat gtctgttttg agctaagtaa ttcattctgg  10920
caagccttca gtttacaaca gagagggcgc atgttcgtgt gggaaggaga ataaaggagt  10980
ctttgattca tttgcttctg agctgctagt gcctgaactt ggactttgga ggccatctta  11040
gcccagctgt gtgagggcca gccagtgttg cagggcgaga ataacgccat tggctcgctt  11100
gaaagcgttc tgactgtcga tggggtgttg gaggtcctct cattcacatt cctggcatta  11160
acatggtggc ccgtctccat ccatccctag ttctctctga agctgccatt tgaacttgaa  11220
gtcacatttc tgtgactctt tatctcagcc cgtgtgtcca ctaagtatag aaagcttagt  11280
gtctcaaggc tctttttctc tccccttgga ttagagcaca gataaaatta gtattcgtta  11340
gattactgag gagaaagtgg tccattgtga tgtggatttc cacatttgtt acattcctcc  11400
actctttgcc tactaaccca gggtggggtg gtttaggaac tttcaggggt tgtaggcaat  11460
gcctgtattg ctgggaaaag tcatttcagg agccagaggt ttctgataga tcattgcaga  11520
ctccttcaca tagtactgta aataatacaa ggactcatga actggaagaa tctttatatt  11580
ttggacaatt cttttattca tggggggggtg gggtgggaaa tctccctatt tgaaaagttc  11640
tttccaaaat catagcgatg tggtaacctg ggctttggcc gtcctgcagc ctcttgagag  11700
gagaggcagg gcctagtaat gcatatttgg gccttatctc tgttacttag ctcttgacgc  11760
ttgctgatta caacttgtag ccgccaagtc ccgtcctgca ccattatctg gaacaaaaac  11820
tttccatgtg gtttgcctca gctctgcctc ggtaggcaca gcactcggtg gaggtggcag  11880
aggtggcgga ggtggcggga gtagtggggg tggaggtgga agtttgtaaa gagcttctgg  11940
aaggggtcac gtgagtaatt taatattttc ctactgttta agttatcctt tccctgcctt  12000
ggcatgtctt ccagaaatgt ttgtcattct tctaaactga gttatctttc acttttctgc  12060
tctggataga atgccgcatt tactaacggt tcttttctca cgttctttcc ctctttgctc  12120
tcacactctt tgtcttagct tcttgctttg aattcctcct tgccctagat aggtgtctat  12180
tcttaaaaca aaaaacaaaa tccccaacat cctaaaaagg aggtgaggac caaattgcca  12240
cattgttttt tgaatttaaa acaatatact aaagtctaaa catttctttt caatttaaaa  12300
atatcccccc cccgtttttt tttatttaaa ggaagaaaaa tactaacctt agctttaact  12360
atattattgt gtttccttcc tcccttttttg tttattttct tttgctttga ctcagctcaa  12420
gtccagctcg atgcagtctt ctggtcgtct ccagagtatg gagcacatgg agactaacaa  12480
tggcggcccc actggctgtc aggagagagg cctgacctct gaagagaagg gggatgatat  12540
cacaaagcaa agaaggcttt attgtgtcct ctcgtgacac taaattgaat tatcttagca  12600
ttattagaac actacaagaa gtaagcagat aaatggaatt gtattccttt aaaaatactt  12660
tagatttatt gatgtagttt tacatggatg gatgtttgct ggagctgttt gtctgtgcca  12720
ccagtacatg tgtgcccagt gtgcagcagt ggcgtgtaga agaggcaatc gggtcatctg  12780
gtctggcgtc cttgatagct gtgaagcacc tgtcgtgcag gtgctgggaa cggaacctgg  12840
gacccctgaa gagcagtaag tggtcctaag tgttgtacca ccgctctggg taaccgtaat  12900
tttggttagg aggtctgctt tctctgatag atactgactg ttgcactagg attttttttt  12960
ttttgatagc ttgacttatt tttgttgtcg tttctgttgt atttaatgct ttggcttgcc  13020
```

-continued

```
tgttgctgtc aaatggtttt taccagagaa aagtaagtct gtccctgttg ctggagtcct  13080
cagccctctg ctcttaactt gtgctactac tgtaaggtag ccaagactgg agtagtggcg  13140
gtaactttac tcagtaggca gcttgcttca tccagtctgc tacatggcct tagttaccag  13200
tgcattggga aatgtggccg ggctacttct gactccgccc agaggtgact accacattaa  13260
agaattagca gccctagtcc ctagctcagc ctccccattg gtgctgtagc cagagtctca  13320
tagccaagat ttaacttctg ctgcttggca aaatgccact tgattcccag gccacaagca  13380
ctttagcatt tcagtttggg atgagaaata cttgggaagc tgccaccttc cataatttga  13440
gttctgatgg aggtatgggg cttagtgagg aaccatggcc tcgtttagtg aggggggtat  13500
tatttgaaag ttataatgga cctgacaaat tctccctgat aatttctggt ttaagtgtgt  13560
tgaagcattg agaaaaagtg acagggagca ctgagtactg gcgaaagcag tacaatctag  13620
tgctactgtt acctaaagcc tcctcatggg gtatgtaggc catttaccac ccagaaaagg  13680
gccagaatca actagatttt tgggagtagt atcctcattt tttgttctgt acgaacttgt  13740
caagggtcaa acttctcagc gtacagtgct ctagacaaga gcagcgagcc atgtggttcg  13800
ggcagcagca gcaagctacg tagtgtcatt ttcaagttga ttttcataat ggcccacaga  13860
aagcgcagaa aacgagagtg tgtacttatt ccatccattg tgacatttag tcgtcctttg  13920
tgtttgtggc agggtttgat gtccctgaag gtatctatgc tttgtctaaa gcatagtgtg  13980
ggaccttgtg cgatcgcttg aacagtataa ccaagtagct gtagactttt gggcccagaa  14040
ttctaaatca ccttgtccag tttctcctta gctttttgat tccttcctct tggtgtgttc  14100
aatgccctct ggcttttcat ttactgtgcc tttgatttgc acagcaaaaa catttactat  14160
tgaatattct tttttttttc agttgttaca tctctgtcct ggtggagaag agtccgaccc  14220
cccctttttt ttttacgggg aatgaaaatg agcctcaggg agactaatcg atttgtccaa  14280
ggtcacacaa cataaccagc tgtcccacca gggtcagatg tgtcatggct cagggcaaat  14340
cctttagtta cccagtgaga gctgagggta agcaaggcac tgtggaaaac tataaagaag  14400
aggccaaggg ggcattgctg tcaccttcaa gaggttatat gttcatagag gacctgggat  14460
gtgctgctca cactcagaat cctatggtga ctcatcctga gatgagtatg agatgcactc  14520
acagaattca gcaaaaaggg attgattcag aagttcagga agacttcgta agaggaacat  14580
tttttcaga gcttaattag ggacactttc agaagtagga gcagggctac agtactcagt  14640
tacatggttc ccttttctag ccacccttga attggttatg taggtgtagc tgctggctct  14700
ctcgacagtc agagccgttg ccaccaactc ctaccatgga gcctcgtctt atcagtgtgg  14760
ggataactat agttcttcca tgaaattctt gggtgtgttg agggacgtag gttgtagtct  14820
gcttaagtcc tggaatccct aagcactcca gtcctgtttt gtttttatcc attgtgagac  14880
tgtatactcc ttgaaagttt aataaaagcc ctgtgctcag gtggtctgcc acatcagctt  14940
taaagaaaga cttctgccac taagcgtgat gatccacact cgatccccag aacccacata  15000
gctgaagaag aaacggtctc tggccttctt ctcatgccca cagtgtggca tacaacatag  15060
taatgttaaa acaaaacaaa aggccctgag cgctcagttt catcagaact tttagaactt  15120
ttagaaactt acaagtgtta taacttgtag gatttctgac ctgtgaaacc tgtctgtgag  15180
tctctctgcg tagttacagg ccttccagtt ttatgctgat aatctgcggc ttctctccac  15240
ccagtcttat gggtccagct gcttagatgg tctacagaag tgccaagggc ccatgccagc  15300
attttaccct tcagacttgg tctccctgtt gcgccctcaa gtggacagtg ctgagctacc  15360
cttcttcagt ggcttgagaa tactggtttc cttattctgc acacgcagta accaaaacaa  15420
```

-continued

```
accctgtcag tttaccacct cagtggctct cgactgttgg ccctctcctg cctttgtttg  15480
gaatgctgga gctgttaact ggtctctcag tacagccttg caaagatctc tttgtgaaca  15540
gagccaggca gcttttctga actgaaaagc tctggactga cgttgttggt tctgctgtgt  15600
cgctgtgctc ttagtagcgc ctaggccttt ccccttggct cagcagggtt agtggtcatg  15660
tggcattggc acatctgtcc aggacacatg ctgccacatc cctcattcag ccactgcctc  15720
agctttgccg gacttttgtg tccccacttg tccccaagac ctgttattct gggctagccc  15780
cctccaggaa gtcttggcct tctttttcac tctacaccga gactaacttc tgctgcttct  15840
cctctctgcc agcttcccct ggtctccatc accagcacag acacagtgtg caagactgtt  15900
gtgtcgttag cataaactgg ccgctcttgg ttgtactgac ttctgcaact gctcatctca  15960
aactgtgtat ggtatggtgg gtagcaggca ctgcgacttc tgtgagtcca gctactcctc  16020
ctcgcgtggg atcgccttgt gtatgaaatt taagactagc tgtagtagca cctgttccta  16080
atctcaacac ttgggaagcc gaggcaggat gacttcacgt tggagagcag tgggggctac  16140
agaacaagtt ccaggctggc catggatgca gagtgaaagc ctttgccaac aaaccaaaaa  16200
caagcaaaca gaaaatggaa aattaggtaa aggtgtttgc ctaaaggctg aagacctcag  16260
tgtgataggt tgggagaaaa attgtatgat cgttacacaa acagatgtaa cgggagaaag  16320
caaaaatcat attttgaaat ataaatataa tctgagctca attttgttaa agtatcatgg  16380
tcaccaaaca ctgtttctta tgtgtgtggt gggtacatcg atgttgaatg aacagaaata  16440
ctttgcagat aaagtccaca gcatatgtca gctgatggat tgggacaaag gcaagacaac  16500
tactcagctc ttcagttacc tgacactttt gtaatcaccc aggtggctct caaagaataa  16560
tcctaaaatg tcattgtgta gtccctggga atagaaccag tctcaggaaa ttagacacac  16620
ttaacacaca tatactcact accttataat atatatttaa gagtaagaat cggggctggt  16680
gagatggctc agtgggtaag agcacccgac tgctcttcca aaggtccaga gttcaaatcc  16740
cagcaaccac atggtggctc acaaccatcc gtaacgagat ctgactccct cttctggagt  16800
gtctgaagac agctacaatg tacttacata taataaataa ataaatcttt aaaaaaaaaa  16860
aaaaaaaaag agtaagaatc attgagaagt ttctgatttc aaaacgattc cctgagttgg  16920
cttactaaca ggcatatttc ttgagacgtt ttgacataga tttgtgtagg gctgggatgc  16980
ctgttttgct gtgtctgaag acagatttct cttgcagcat ttagtagagt caggactgaa  17040
acgcctgggt aaaccattgc ctccctgcac ccaccccccac ccaccgcgag acgtggtgag  17100
ctgccttcta tagagaagct ctctctaggc ctcgtcctta cactcctgct ctctgttggc  17160
cttacttccc ctgtgcttca gctacaagct gcagttcaga tgcagagtcc tgttgtatgc  17220
ctggagtcaa agcattgttt ttaccctggt aaagttgaga agaacagaca tttgagaggc  17280
tgaccagaag ctctctccag tgaagaatca aaacccaata ctcattttgc ctcactctcc  17340
tagctagagc gcagcctgtt gtttgggggt ggggtgctga gtcatgcttt tattcatgag  17400
tttatccatg ctttttttatt acctctgctg gcagatcacc atccattgtt catgagccgc  17460
ccagcttgtt gacttttata agttacatgt aatcaagccc tcttgcaggt ctggctacca  17520
taactggcag tcccaccaag ccgggctgac cagtctgcat ttgtgctgac tcccatgttg  17580
ggtatctgtt ctgctcgcca agtgcccttg cctcctccac ctgtactgcc gatggaagag  17640
aagacacctg cttgggggtt gggggggggg ggagcttgca gatgtaatgg gacacctcca  17700
cagaacttgg tggagagctc attgtccttt agtttaggat aaatgaaggg tttgagggag  17760
```

-continued

```
ttcgtgatgt cacctgggtc acttctaaag gaaggcttgc tgttttcttc attccctttt  17820
cctagctgat gacttagcaa gtataggtaa agtccagaaa ctttgaaaaa caaaaggtaa  17880
gcgctgtgtt agagcgatgg ctgggcagta aggagtactt gctgcttttc tagatgaggg  17940
tttttgtttc cccacagttt gtttcggtgg ctcatggctg cctgtggctc tcagctccag  18000
gggatctgcc catcacacat gtggcatata catacacagg caaaaaaacc acatgcacat  18060
agatagaata acttttaaaa agcaaatgtt tatatatttt atgtatatct gtgctgtttg  18120
tggatataca tatttgtgta tgtacatatg tgtgtaccat ggaggagaaa ggtctatgcc  18180
aatatcttca gttgctctcc actctgtctg tctgtctgtc tgtctgtctg tctatctatc  18240
tgaggcagta tctctcacta acctggaaca cactaattgt ctagaccaga tggtcagtag  18300
gtcccaggaa tccccctgcc tctgattttt cttcattaaa gttactgatg tacactcaca  18360
tacctggctt tttaaaatgt ggctactggg gggtagctat ggattactca ggtactccag  18420
agcaaacatc ttacaactga gtccctgccc cagccctgga atcccacagc aaaaatctga  18480
acaaccctta tggtctgatg taggtgggcc tcagattata gttggggaaa taatgatctt  18540
ggtgcaaagg gaaaaagaag aaagaaaaat ctagtagaag caaatattat ttacattgta  18600
ataagaagac taaaccaatg gccagaaagt tcctctttga ttttcttttt ccttccttcc  18660
ttccttcctt ccttccttcc ttctttcttt ctttctttcc cttttttttt ttgttccttt  18720
gagatgagag cggactagag aatccttggg aatacaggtg tttagttttg cctctttagt  18780
ttcattttgt tttgctgttt tctcattgtg attgacatca gcttatcctt ccaaaaggat  18840
gtgcttaaga tgacaaaaat aagagaatat tcagaatggt tagaactaaa aagtacctaa  18900
gtattgctaa gacctcaaaa gatgtcgagt caaagaagga attaagttga cactcattag  18960
acaagaatgt gaatccattc caacgaggat gcagactttg tgaatggctt agaggtgaag  19020
agcagagagg attagttctt cttcatgagt tctggttatt ctggttatag gatctgaaag  19080
catattatta aagtcatatt tcctggaata gttcaaaatt caaatacctt tcccctgcct  19140
gttgaagaca ggacaactgg cttgtacttc tttttcgttt tcagattgat tggttcagtt  19200
aggagcacca ggcgggttgt acctaacaac agaagtcaga cctcctattt ttcaactttt  19260
aaaaaaaata tatgtgtaga ctccaaagtc cacactcaag aatgagagct gagagaccca  19320
gtctgttata ggaagtcatc taagaagtag accaggcagg aatggctgtt taagcctagc  19380
agaggagaga aagcaattcc tcctgtgtcc taatgaattc ccttttcatg tggaaagctg  19440
gcttttgttg ttgctaataa tacaggattt ccttcagaga atttttaatg tcttgttcag  19500
ataccacaca gagagatatt gaccacaaat attaatactg gtttgggaga tatgttgatg  19560
tgatgttgtc cctaccttta ttaaactgac catcttaata actccatcca tcttggcacc  19620
gacacctctg cttttctact tactgtgttc cttacaactc ctaggcctta gagcggtgct  19680
gactacatta cccgtcctct tccctctctt ctatcttcca ccccgccctg ccccccttc  19740
tccagggctt acttccacag gagcactcca tcctcccaag gaccctgccc atctgcctac  19800
aagatctgcg agcatcttcg tatctgcctt gtaagtgttg aggatcatta ctgtcattat  19860
ggggagcaga ggccacgccc gtgtgctgct cagagcccaa gtgagttggg tcagtagatc  19920
cttagctgct gaagcaaaca ggagggctag tgctgtgtgc tggtggtgac agagccagct  19980
tctctcactg acgctggcaa cccaggaagg tgctcttcat ggctgccact ccgctctaag  20040
cactgaagag caggcgcagg agtgtttctt tttccaggtg acttcctatc tttgctgttt  20100
ggtgctgcca tactcatatg cttgtaggtg cttcttactg gccttaatat tcctggttta  20160
```

-continued

```
gcttttggag cctactctat tccatatata tttaaccaag aggtggaggt ttccagtgat  20220
ccccttattt tgacaggaaa cgggtcttag tgtttttgtc aggcttgtgt gtgtgtgtgt  20280
gtgtgtggtc taatcaggaa gtcatccaag ttcaacttta aaatgcccat aaactatcaa  20340
tgcaagtgtt gcactcagag tattcttttg gggatgtagc acatttttga aaaaaaaaaa  20400
aacaaaacga ttgtaagaca ttaagttagt gcatttagtg acaatgacat gataagctac  20460
taaagggaaa taccttgacc ctcaggccta ccctatcgcc ctaagtccct ctccaaaccc  20520
tcccaccctc ccttcagaca tggtcttatg tagcccatgg gggaatgttt ctttattaga  20580
cttattgttt aactatcctg tatttattat atatttatgt gttataacta cctatttaag  20640
tagaatgtgt acataaactg atatactatg ttggtattta attttaggta atactgttat  20700
taattttgag acagagccat tatctcactg tgtagccttg gctggcctgg gactctgtgt  20760
agaccaggct ggtcttgaat tcaacaaaga tttgtttctg tctccctagt gctgggatta  20820
aaggtctgct acactgtgta tgtcttaggt cataaatctt aataatccca gtatatttaa  20880
atctttaaaa cgctatatat aacctagaaa ctttttattt tgcttcaagg gtatttcatt  20940
tggttgtttt tctatctgtc catttgcatc agagtttaag tgaaatcagt ttgttttgtt  21000
gctggaccat tttttttttt ttagagcaaa tgtactttgt tccaatttgg aaagctagtt  21060
ggtgagaacc ctgagctcct atcaagggca gcggaagctg gctctttaaa cactttgcat  21120
ctttgaagta agctcttgtc ttaacacagt cctcttttca cacatgagtt cttggttttt  21180
tttttttttt ttttttttga actgcatgct ttctaactct gagctgatta ttgattattg  21240
aagcatttaa gtaaagagat gggagaaaga tagaagtgca cggaccaggt gaacatgttg  21300
tcaggcaaag gaccgtccgc gcaagaagac atcttcagga cccgagttta taggccacct  21360
acgctggtgc atcttgtatt cccaacatgg aggtggcgga gactcatggc tccctagcca  21420
ttttgcccgc tgtctcagaa acaaaatgga ggacggcgga gggctgacac ctgcgcgcat  21480
gcgtgcatgc gcacaaatgc acagagcacg gccgtttctc ttattttaat gaacggagaa  21540
aaaatttata ttgtctttac ttacccattt ttgttctctt ttgagacagg gtctccttag  21600
gtagccctgg cgctcacgga actctcgatg tagatcaagt tgaccaatga tgttgagaga  21660
acatcttggg tctgtatgga tgtgacagct gtcagtaata tctgatggcc tatagcttag  21720
gcaggaaata ggaggtggga catctggcag gcagaaagga ttctgggata acgacaggcg  21780
ggagagtcgc cgggaccatt cgaggtggca gacgcatgac acctgagtac aggtaaccag  21840
ccacatggca gaatatagag tagaataaat gggttacttt ataagctagt gagagaagag  21900
cctagttata tgtccaaggt atttgtaatt tgtaatattg taaatgtgtt ttgagtctga  21960
gtcttactcc tgggagcatg gggctgggag gaaaaaccat caaactaata tactcagact  22020
tgcgggaaac cttctgtagg tgcttctagg tatggtggta gacatggacc actatgtccg  22080
gcaacttttt tctgagataa acgtttaaac tgttgtgaga ttgggctcca actccctgcg  22140
gcatctcatt gacacctggt agaccctcca aattgctggg gctgtagttg tgggccgcca  22200
tagccagcat tctccccaca ctctttgctg ggcctgcatt tcaggccaag cgcctttcca  22260
ctgagcccac ccggccccac cccacctccc cacccccaac cctctttcta ttcttgatga  22320
gaaaaatgaa acttattgga aacggaagcc taagaaatac tctgaaaaca agaccacttg  22380
ttcaagcagt cagagtcgga ctagaattca aatttggact agaattcgaa ttcactttcc  22440
caacaggctg cttcttggac agcctcaggc tcctcccagc gagcaaagtc ttcccgccta  22500
```

-continued

```
agaaactgga cactgctaat ctttacacac caaaagagag agcctttagg ggtccccaaa  22560
gcagtggcaa tatcatacat tcatctaagt tggctcctaa tttgttaaat gtggttagaa  22620
accattttct gttttatttt gatacagggc ctcctgtagc ccaggcctca agtctctgta  22680
gttgagatag ccttggtcta ctgagcttgc actttccccc accccacccc caccccaggc  22740
tgggcttgca agcatgagtc accattgctc ttcggccact cagtagtttg tagagttagt  22800
gctcctcgtt gttctacagc tcatccctgg tatctccaga cagtctctgg aggcagtgca  22860
cagcacatcg gaggggctca gtacccacgc ctcccacgaa ggcgtgctcc tctgtggtat  22920
tcccaccctt accgcaggaa gaaggtaatt tcatatgcga tttgctcagc tgacctacgc  22980
agatgatctt actgtctcgt atacttctgg aaatcccaca cacctttcct gcccctgagg  23040
aaaaatttct tcctgatgct gaattcagag ctgtatttaa tcctgagcat atgagagtga  23100
gtcaccttgg agtggtgagc aatcccactc ataccttcca ccttcacgtc agcgtttgaa  23160
actgaagacc ttggtgcatg aataaagtct gacatggaga ctgctttcaa acctgagaac  23220
agtagtgaaa cttctttcca tcccctccct ctcttccctt cttcccttct ttctttcttc  23280
cctccttcct tcctctcttc ctttctttct ttctttcttt ctttctttct ttctttcttt  23340
ctttttttct ttctttcttt ctttcttccc tccttccttc cttcctttct ttctttcttt  23400
ctttctttct ttctttcttc cctccttcct tccttccttt ctttctttct ttctttcttt  23460
ctttctttct ttctttcctt ccttccttcc ttccttcctt ccttccttcc ttccttcttt  23520
ccttccttcc ttccttcctc tctctctctc tctctctctc tctctctctc tctctctctc  23580
tctctctctc tttctctctc tctctctcac cagtgttttt tagttcagct gcaaatgaaa  23640
ctgcataact tcagctctga aatgcgggct atgactggaa tgtttgttca gacaagaaag  23700
caaatgtttt tctgaggagg cagggaaaag gaggattgaa aattttgggt agtctgagtt  23760
ttcaaattca gactaattga gctgaatgac taccgttttt gtgatgtcac tgtgtcccca  23820
aaaagacaga ctttcgaggt tcaggagata gtgttgaaca tgtgtgtcat tgttagggtg  23880
atatttctgt cattacctgc acagtgggta acctttacct ctatttctct tatttgtaca  23940
gtgtcactgg aagttatttt aaaagcttac agtccttgtc aggggccttg agatttctag  24000
gataatttca aagaatgtaa atcattaatg atccttttta taccaataga acaaaatatg  24060
aaagccaatg actgcttccc caaaaggccc tgcgctgtcc cctcctaaga gcttgtctta  24120
aactggcagt tctccagcta gcctcagcct tctctcttag caagtgttgg gcacgcctgt  24180
tttaacctgc gcaggttcac ttcccacaga tcgaaggagg gggccctgtg tgatgcgggc  24240
cctgggctag ccttattaac atattttgaa taactgtatt ggaatgtgtg ccagctttgc  24300
caggcttttg gaaacttgcc aggcagcagt aggagttttt gagaggactg tggagatgtg  24360
agcctgcaat ctttttttctt tttgttcttg gaagagaaag attttagaac acgccattag  24420
gcccacctca tgaaatgaga accgggcacc tgtatctcat caccccaact ttcccaacga  24480
cctctgtctg ctttagtttt gtttcgtttt aattttgtgt aaatttggat cttctctatc  24540
actttttggt tttttgagac agcgtttctc gctgtagccc tggctatcct ggcactcact  24600
ctgtagacca ggctggcctc gaactcagaa acccacctgc ctctgcctcc caagtgctgg  24660
gactaaaggc gtgcgacacc acgcctggct tctatcactt tttttttct tcgaaatatg  24720
tgctgtcact ctgtagctgg ggctggcttg gaattccttc tgtagatcag gccagacttg  24780
aacttttgag agatcgacct gctctgcctc ctcccaagtg ctgggattac aggtgtgaaa  24840
taccacaccc agatttttaa ctttaatttt ttaaaagtat cttaggagat atttggtaag  24900
```

-continued

```
ttgacctttg tccagcaggt ttgaagcttt ttctgggagg cagactttct tctgggaggt  24960
tttgtgtgtg tgtgtgttgt gcgggtgcct atgtaaaccc ataaatgctt ctaccaggac  25020
agacagggta aactatggcc cctgtagagt gatgctcaca ttataaagat gccatatctg  25080
tagcctggga tctgtgtctg tccttgacac gtgatcaaga ccaaaacttt gggttctaat  25140
attagaattg aaagagaagg cttctagatg tgttcatttg tactgttttg tttgtttgtt  25200
tttgtttgtg tgtgtgtgtg tggggggggg gtggtgatga gatacaggtg tccagttctc  25260
atttcatgag gcgggtttga ggagcactgc tcatcggagg gcctctcagt gtgaagggtg  25320
tgtgggatgg atggctctgt ggtgaggcgc ctttataatc tgtacccagt atgatgcttt  25380
cttactacgt accctctcag ttcattttgc ctccttcttc tgtccagtgc tagggattga  25440
acccagggtt tcacacatgt gagacaggcg ttgtggctgc actcccagct catgcctctt  25500
tgggatggag tgtttccggt tagagacagt agctctgacc tatcaaagac tatgaattga  25560
agctgggtgc ctgtaatcct agcccttagg cgggcgaggc aggaggatcg gtggggcttt  25620
gagggtagcc tggaatatct agacagacct tgtcaataat aataataata attattatta  25680
ttattattat tattattatt cagcaatgac ggtacattta ctaggctcac caaggggcta  25740
tagaggtgtc tcagcggtta agagcacttg ttgctcttgc agaggacctg ggttcagttc  25800
ccagcaccca catggtggtt cacaaccata tcatccagga aatccaatgc ccttttcggg  25860
gctctgtaac actgtgtgtt ccatatacac gcaggcagaa acactcacac acagaaaaca  25920
aaacacatct aaaacataat tgaaaaagta gactcaccag aaatggggtt ccccttccca  25980
gttgagggct ttactttttc ttttgtctct tcaaagcctg ttcttaatac tttcaatata  26040
gggtctcatg gtgcccagga tggttttgaa ctcctgattc tcctgcctta gccttctcat  26100
ttgctttgta tgtatcacca caagacttac ttaatttttt taaatcatgt aatatggggt  26160
atcagaaata ggaaagaaca catttgatta ttgttactaa aaaggctttt aaagttggaa  26220
tttagtttat gggactatct ggcagaaaac cctgagttcc aattctaacc ccctataggt  26280
tgaacatggt ggtacctaga tgtgatccta gcactcagga tgttgaggtg taaagaacca  26340
aaagtttggg gttatcctca gctatatcgg gagtttaaag ttagccttgg ctacatgaaa  26400
ccacatcacc tgccctccaa aaaaattcct tttagaattc agtgtctaga gaagggttct  26460
ggccttataa gcgaaactgt acctctactt atttacttta aaaatatgtg tccaaggctg  26520
acatagtact cttagtagcc aggctagcca cccactatag cgttcctcct cccacttcac  26580
tttctcaagt gctggcatga tagatgtcag ccactgtgcc cggaagccca ccgtttttaa  26640
tagatatttt aatgagccac atgcactcgc atttcaagcc ttttttttatc cagaacgctt  26700
tcaagtttct agattggaat tattgtgtcg ggttcttttg ttgaacctca gtgtctgtct  26760
gacttgtagt tttgtcaata ctgcctgtga ttcataggtt tatatggtca ccatttacaa  26820
ttaagagggg aaatataact ttgttttttt ccaaaatttt tcggagttga tatataacag  26880
actgttaaaa acaaacaaac aaacaaacaa ataaaaaaaa accattgtga gtctttatga  26940
aacaatgtgt gtttatgctg aacacctttg aatatcattt cagaaaatct ttcttctctt  27000
ggtatagagt gttattttct tcgcggtgct tcttcacctt ggcttgcaca gggtgcaagt  27060
ttatgaagcg ctgcaaattt gactgcttgg ctgtcctctc cgacacccgt gagggtggta  27120
gatatgaaat ctcactcttc aacaagtaca tgcatgagag taaaacagtt tattcaggtc  27180
ataaaacagt gctggctccc agcccaagtt taagctgata gcgtgctggg ggcgcagcgg  27240
```

-continued

```
cgatgactaa ttactgaaaa tctcttcaga atgcgttacc tttaccagac ccaaggaaga  27300
cttatttagg ggtacgtcag atatcatagg cgaagctcaa atgctttttt tgttgttgct  27360
ttcttatgtg tgtgttgtca atcacagcag ctcggttggt atttgtgggg acacatgcag  27420
ccttttttagg ggtggttggg ctctccctgt tttgggggta aaaccatttc cacacaagtg  27480
aatctgcaga ggctgccttc aggtgtatgt agtgagcttt aactctttca gcccttgtcc  27540
tgacttgtct gacccaggag cagctggctc cctggtatat tgtataatgt agactggctc  27600
gtcaattcag actagctcgt cctgtttggt gggtttgtta gaaactgcag agctaagtaa  27660
atatgcgata acagtttgaa tggtatttga agttaaagag cgcttgcaga ctgactgact  27720
ctgagggaca ctgtggccag ggaccccggg gctgcctctt gggtcagttt ccatttttat  27780
ctgagtttta ggaaggcacc gtagtaatga aggcctggtc agatgacagc accttccaca  27840
tgaggcacgc agtatgtcat gtctgatact acggatgcca ggggttaact ctgtcacctc  27900
atgagccagt gcccactcag tgcccactca gtgcccactg agaaaacagg gagggctgaa  27960
tggggcctgc tgtgtgggag agtgtttgct gatgactatt tctgtgtggc actgtgttcc  28020
ctccgctgta gggttatttc ctggtttctc agaacaacac tgtctccctg ttaacttcat  28080
gagggacgtg tcttgactga tgggcgagcc tctaagttct ctgaagggct ttgtgccttg  28140
tcagtaccgt cccccctacac acacacacac acacacacac acacacacac acacccatct  28200
ccttcataag atcacctctc taggatgcag agtggaagtc ggatgctgac acatacacac  28260
acacacacac acacacacac acacacacac acacacacac acacaggttc actttctgat  28320
cagagacaag tgaagtctta gaagatctca atttagcaac aacctgtgtc cccaccccca  28380
cccccagtga gtcactctta gtttgaaata ccctaaaaga gtctctcatt tctgtaggtc  28440
agacaggttg taacctgccc gactgctcag cggcattggt gttggatgat tggagagaga  28500
agaggccaga actgtgtggc cttgtactga caacctaact gtaggtctgc ttgcagacag  28560
agcagtcctt tgtgcaatga gtttccccat tccattctac tcgtaatagt gaggacatga  28620
tagctctatg tgtgctatat ctcttttta aaaaaaatta gttctgaaat tggaatgctt  28680
ttcaagctct ttgtttttct gattctgttt tttaaaaaca gttttctgtt ttaaatttgc  28740
ttttattgag attgagaaac tactttttct ttcttccttc cttctttcct ttcttctttc  28800
tttcctttct tcctcccttt ctttctttcc ttgagacacg gtttctctgt gtagtcctgg  28860
ctgtcttgga actctctata gaccaggctg gtctcaactc acagagatct ggaattaaag  28920
gcataaacca ctctacctgg ttactttta ttactctttg aaagtttcct atgtatatat  28980
aattttgcac ctatttttgt gtgtgtgtgt gtgtatgtgt gtgttggctg gcatgcatgt  29040
ggaggtcagg ataatttgtg ggagtcggtc ttttccttcc accatgtggg taccaaagat  29100
agaactccgt tgttcaggcc tagtggtaag cagctttatg cactgcggtg tccttcctgg  29160
ccccactgtg gtcttttct gttcatgaac tgaggattgg agaacctctg ttcattacag  29220
tggccgcttg tgtgtgggta accgtcagag gtcaggagaa gataagatga gggttagtgt  29280
aaggcgtcct ccttggacat ttataaagtg gtgtcagcat caagagtgtg aaggatagtt  29340
ggcaatggga acttcttttc ctgtaagtcc cttccccaaa ccctctccct ccctcgtgaa  29400
aaaaagtttg catgcaagtt gatgcttctc agaatcctga tgcttgcttt cagaggaatt  29460
ttttttcctg tgccaaagtt ttgtttttca tgtgacttct tgtagcaact tgggtcttcc  29520
tgaaaagact ttttaaagtg cattggtaaa tgtactggta ataaacccaa aggcaaattt  29580
actgtagacg tttgtacagt ttagttaaag ttactaggga aggcaagcac tacccacagt  29640
```

-continued

```
gattgaggtg aaagtgactg tcacttgtag gtaaggcaaa gtcgcttccc actggagagt  29700
gagtgtgagc tccagagaag cttccagttg ttcctgtgtc ccaccaggac accacggctt  29760
ctgctcctcg ctgacccagc taggtggagt agcatcatgg cgcgttaacc aggaaaagac  29820
gcttcagctt tcaggctgga cgtggaactc tgtggtaaac ttccatgtgt aaacccctgg  29880
atcaagtctt agtctgtctg tctgtctgtc tgtctctcta tctctctctt taggtgtgtg  29940
tgataaactg tcaaacacac aagaatgctt tttctttttc tttttctttt tttttttttt  30000
tttggttttt caagacaggg tttctctgta tagctctttg tagaccaggc tggcctcgaa  30060
ctcagaaatc cgcctgcctc tgcctcccga gtgctgggat taaaggcgtg cgtcaccacg  30120
cccggcttac aagaatgttt ttttaaaaca gattttttaa tgtgaatctg tatatccatg  30180
tgactatatg acacatgtat gctgaggtca agagagggca tcggtcttcc cagaacccgg  30240
gttgcaggta gatgtgggtc ctgggaactg aactcagtaa gaatagcaag cgttcaaact  30300
catactgagc cacctcttgg aagatgtttt ttttgaggaa agagtggtat tacatcttga  30360
cctgattggt aaaaacaaat cttgtttttc tagttttggg ttcttttgct acagggtctt  30420
gtctttgtag cccaggctag ctatgaattt gcagtttagt ccagtctagc ctccaactct  30480
gcatgcatcc tcctgtctca gcctgaccca tgtcatagat gatcaccatt aaaacactac  30540
aataaggccg ggcagtggtg gcacacgcct ttcatcccaa cactcaggag gcagaggtag  30600
gtgaatctct tgagttcaag gctaccttgg tctacagagc tgagctccaa gacagccagg  30660
gctacacaga gaaactgtct ccaaaaacaa aaacaacaaa caaacaaaca aacaaacaca  30720
aacccaaaat gagagcgaca gaacacgatg gtaatatact catccttcca ttaatttgaa  30780
gaaatgactc aggaatgcca ataagtgctt gctcagcaac ttacagatgc tgactaagat  30840
gattcgttgc atgtgtttgg tctgaaaact taacagtggc tttgaccaaa atagtaagct  30900
gttacctgat gtgccatatc agttaagagt tgctgttgta agcaacagaa atctctgctt  30960
taaccggaag gggaggtttt ctccctctct ccctctcttt cccaccccct ctctccttcc  31020
tccctcctcc cctcccccct caagtcctcc ctttcttgcg cgcgcggggg gggggggggg  31080
gcttgcaggt attcgggagc tcatagactt tctgggactc agcaacccat gtctggggcc  31140
tcattcttgc tccttgagat gattcaaaag ctggggtgga tttgctgagt gaagccagtg  31200
tagtgaatct tgtgcctaca ttttaggtta gagcagtggt tcacagcctg tggattgtga  31260
ccccttttggc aaacctctgt ctgcaaaaat atttacctta tgattcataa cagtagcaaa  31320
tttactgcca tgaggaagca atgaaaataa tttggggggg ggaggcagtc gctacaactt  31380
gaggagccgt aataaagagt cacagcatta ggaaggtttg agacccactg ggttagaggg  31440
aacacagaaa atgattatct aagattttca gttttgtggg gttaagggtt ttctgacaca  31500
ggaaggggag accatacatt gggtaacaga aaagaatcag ttttcacatg tgccatgttg  31560
gtggcatgtg ttggacaaca ggaaggctta tgtctccatt acatgtgaca tgtggtgaca  31620
agtggaaaaa ataaagatga gctccactct tacaaatacc ttaactagac agtggtctct  31680
gggaccaggg aggttgtcca ggaaggaaag gaacttgtga agtcaaggat ccgaagtcgg  31740
tcccttgaac tcccgtggca gcaggagagg actgcctcct ccccagcccg tacacaaccc  31800
ctcacaggca attcacagga aaaatataaa atgtctgtta accgccatga gaaaaatgta  31860
gtaagaccaa tagttttcag tattcacaca gtagcatcca caaatactaa gtagatattt  31920
ggtgtagtga agggctgttt tgtggttggc agctccagga cttgggggcg gggtggggtc  31980
```

-continued

```
tcagacaaag gttaattcaa gttggggtgg gagtgcagtg tgcctcgtgg ttttatgagg  32040
tggctctgct gtgtttctcg gtcccctcgc actttctctt ggtggaatgt ttgtcctcac  32100
acacactcct gtgcaacccc tgagctccag tggaccccta ttttgggggt gccaaagtgt  32160
atggcgccca gactgtacct gccagaactc agaaggttcg gtgatgcacc tgaacagata  32220
ctttcagcac cagctgcacc ttggcctgtt tattttctca gtcactgtgc ggctggcctt  32280
tgaggcctat agctctaggg tagtgcagag ctgtagtggc tcaatgattt ccccaccggc  32340
aagccctcca gagaggccag gtggtggtgg tggtggcggg ggcggcgggg gcggcgggga  32400
cttggctcca ctgctccctt ctttatgcag aaggaaactg atgctcagac tggctcccca  32460
acctatgcag ctggaatggg gtgacagatt caaagacaag agactgttca aaaccctttc  32520
cctggtcttt gaaccagttt cctcctcaca gacatctttt agaggagaac agagagcctc  32580
cctgacctgg agagagtttc ccagcgcttc tgcatcacgt cccttcgccc acgatttaac  32640
ttttttcctg agttgaaaga tgtccccaga aagcgacaga ggccagcacc acaggttctg  32700
gagtcacagg gtgaaagata gcctgtggtt tgggtctaga ggggcgttca cagaatgaag  32760
agagaacagg ctcggaagca ccttagagga ggagggacta tcaaaagatt gtttcggact  32820
tggcaggagg caagccagaa gagccagaat gggaacggct gccggagcca gaacacactt  32880
ttaaaaggaa aatggatccc ggccaggtgc tctggagagg gtggggtgaa ctggccaagc  32940
aggaagttac ggcgacgttg tgtaatttgc agttgtgttc tctgcctacc ttctctggct  33000
aaatcagcct agaggtgcag tgatcttaaa gagagaaagg aaaaaaaagc ctagcttgtt  33060
ctgggacagg tgcagttttg tgcttctggg ttttagttgt ttttcagtgt ggccactttg  33120
gccttggggc ccaaatatct tgactactct tggtgttttc ccgtgccgca tgctgcagct  33180
gcatcgttgc tttaggcagt cctcctgtaa gagtaactgg gctcttacat tcagaggcta  33240
ctctgccacc tcccttctga ctcgccagtg gtaacttcca tccagtctga cctctgcttc  33300
gtcccctttc ctgatgttac cctgcaggat cattgcaatc cacctcccaa aggctgagga  33360
tttaaatgtg caggcttctg ggctggagcc atgcatggtc cccagcatcc acacagcaac  33420
tcaccatcac ctgtaactcc cgacctctgc aggcttccag ggccaccagc cacgtacatg  33480
gtatacatac agacatgaag gtgaaacacc cataaataaa aaactaaaca aacaaacaaa  33540
tacaaatgtg gctagctaga ttattctgat cagccttccg gagagaacta tacagtgctt  33600
tggtgtaggt aagaatacgt gtccccatgn nnnnnnnnnn nnnnnnnnnn nnnnnnnnnn  33660
nnnnnnnnnn nnnnnnnnnn nnnnnnnnnn nnnnnnnnnn nnnnnnnnnn nnnnnnnnnn  33720
nnnnnnnnnc tgctgtattt ctcagatttt aatagtcatt ggtaaaaatc ttggaaagca  33780
ttccgtgtgt gctatatatg cacaggctct agtactttat ccagtattta cacgtcactg  33840
gttactagga tgaacacgaa gaggctttag gcaggatgag agaatgtggg taggcttttt  33900
gcaaatactc cggcacttgt ggaagggact tgaatctaga accagctccc aacccacaca  33960
tacacacacc cagggaaatg ccaaggtacg atcatagcgc agaaaagagt gagcatcttc  34020
ttgaaggcca cgggtgcggt tggatcatcc aagtgaagcg cacttggatg accggaaggt  34080
tgagtatcca gagtggcgtc tttgtcagct gagctgagga ggtgtgctac tttcttctgg  34140
ctttttggta cagcctcggc ctgtgattcc agcttctctc cattgtgcta gggtctcgaa  34200
gagcccttcc tcaaatccgg cgagcagctc cagtgtttgc ttgtccccca ccccgcccca  34260
cgtctgtgca gatgagtgtt tctccaggct ccttgttgtg gagatctgtt caaagaggtg  34320
ggagaagggg aaggactcaa aattaaacct ccccatgtct acttttggtg atctgttgct  34380
```

-continued

```
gatctccata tcccttcacc ccagtggagg gacctgttaa ctggcttttc tgagtgcctt  34440
tttctttcta ctctgcatta cccctctggt ctcacccctc tttttctaac ccttaagggt  34500
tagttggttt gtttttgttt tgattttgtt tttgtatttt tccctctgtt agaatccatg  34560
tcttggtctg gagagatagc tcagtgctta agagcactag atattcttcc agaggtcttg  34620
agttcaattc ccagcaacaa tgtggtagct tacaaccatc tgtaatgtgt tctgatgccc  34680
tcctctggca tgcagatgta catgtagata gtacactcac acattaaaca aacaaacaaa  34740
caaataagta aatctttaaa aagagaaaaa gagaaaccaa gtctagcaga ggatgtgaca  34800
tataggaggc actcagaatg tggggctcgt agctagcttt gtgatagaac ctgtgtggac  34860
catgtgaggc cctaggctcc tccttcccca acaccaccaa taaataaaca agtaaatctg  34920
cctgcctgcc tgcctatcat ctatctatct aacatctata tatctatctt gaatgaacaa  34980
gtatcagaag gagagatgga accagctctc tgtcctcgcc cttgcatccc ttaggctctg  35040
acttgaagga gtctttcatc tggagagcat ttgaggtggt tcccactctg aagctctgag  35100
tagtttctac atggaacatt tgtgtgtgtg tgtgtgtgtg tgtgtgtgtg tgtggtgttt  35160
agtgtctctc agctgcaata aaccataaca gacatcgttt ctatgggaac atgcattctg  35220
agccctgatg aatccattgc atccaagccc gtgagagaac ttgtcagtca gtggggacct  35280
taatcaatca catgtctcct gttcggcttt ttaaccactt ttcgtgtaaa tgaacaacgg  35340
gctgtttctt tgctgaagga ccagaatgag agaagccttg tcttctgaga atataaatta  35400
ttacatttta aagtgaatct ccttcatcca acacacaggg ctagtttatg ccaagtatat  35460
ttgtagtgtg cctagcacag gctgcatgat ggtataggag tgcttcacac atgtataagt  35520
aagaccgtcc cccgcagagg tcaggattag ctttcactta aagaagactg gaactcagcc  35580
tcgaaggtcg tttccagatg tgacgcggcg attctgcgcc tttggaactg ctttatccat  35640
ttgcctgtct tccttgactc acgcggtcct gttaccaaat ttatttttag acacagtgga  35700
caaaagcaca atgacatttt caagtagcca atagcagtgt caccctttca agacccgaaa  35760
atgtccctgc tatcacgacg caaaacctag aagcaaacag tatggtgctg ttttatttcc  35820
tctcactgta ttttggggca taaccgatta ttgacttcgg agtgggttag ccttcctaat  35880
ttattttatt gtattttact tactctgtgt gagtgtttgt gtgttatatg tgtgtgcgcg  35940
catgtgtgtg gtgtgtgagt gtgtgtatgt acatctgtgt gtgtgaatgt gtatgagtgt  36000
gtgcatgcat gtgagtgtgt gtatgtacat ctgtgtgtgt tttgtgtgtg tgtcagtgtg  36060
tgtgtgtgtg tgtgtgtgtg tgtgtgtgtg tgtgtacatg gatgcttgca gacacacagg  36120
tcagaagtca gttttgaggt tcagttctgt ctgcccgtgg gccctggtag tcagacgtgg  36180
ttgaggtttg ggggcttttg ctcactgagc catcttgttg acccacacag tagattttta  36240
ttctaacttt aaaaaaaaat ccttaaaaaa agaaaagaat aatggcacat caagaaaata  36300
gcataaaagt agcatgttaa agacttaaag tccagatact ttcactttaa aaatctatgt  36360
gatgccaagc agtagtggta cacaccatta atccctgggg aagcagaggc agttggatct  36420
ttgagtctga ggccatcctg gtctataaag tgagttccag tacagccagg gctactcaga  36480
caaaccatgt cttgaaaatc caaaaataaa taaaataaaa taataataat acaaataaat  36540
aagcaaaggg agaaaaagtg tatgtgatat tccataaaga tgatctatat gtgttaagaa  36600
tattcacttt tggctggtgt ctgtttgttc ggtttttga gacagggttt ctctgtataa  36660
cagctctgac tgtcctggaa ctctccttgt agaccaggct gacctctgtc ttacaaagat  36720
```

-continued

```
tctcctgcct ctgcctcctg agtgctggga ttgaaggtag ctgccacccc tccaccatgt  36780
cctttctttc tgttttcttt cagtctgtgt actttctgca acagttgtgt tcttctttcc  36840
tgtccacatc acatgcgtac actcactcat gcacacagca cacagcagag cgtctctaaa  36900
gtctttctgt ggctcagact tctcaaggtc agctccgtag tagagcaatt tcacttctct  36960
acgccagcta ctgataagta tttgtagtga tatgtatttg ttgccgtgtg gatttctcat  37020
ctaacatcag agcagattct tttaatatga aacttgatct ttggaatctg gttcccataa  37080
ttatgagaaa ttgaaacctg gctcatgaga gattagttgt gttggaggga gagaacaatc  37140
catccgttgt atgcagtaac cttccttggt gaggctgaaa gcacctgagt cactggggtt  37200
gaaggcagac actaccacag taggcttgtc tgtcacacgg gtgctggcga tggaactcag  37260
gcctgcatgc ttgtgctgca agcttgtgct ccactgctgt aaaagcattt tttcataact  37320
ggcaagtaat agctaagtaa tagtttcatg atgggaagga aaatcaacag ccggatttag  37380
aaaattaaga ttatttaaca gacactgaca tctgcaaata actggtcttt ttcctatggc  37440
aacagaggca tgtatggtgg aacaccgcct ctggtgctac tagcctggtt cttgggtggc  37500
ggggggtggg ggtggggtgt tagtcttaca ctgaaaactg cattcacatg ttgatcttcc  37560
tactaacttt gttttttttt aaagatttat ttattattat atatgagtac actgtagctg  37620
tcttcagaca catcacaaga gggcatcaga tctcattatg gatggttgtg agccaccatg  37680
tggttgctgg gatttgaact cgggaccttt ggaagagcag tcagtgctct taacccctga  37740
gccatctctc cagccctgtt tttatttttt aatatccaac atgatccaac atgatctagg  37800
gtcttaaaag acaacaaatt catttttctt tctgggtgtt ttttttaaa ctttttattg  37860
attctctttg caccccagtc ccactaatct ccccaccccc tcatatctac ccttctcctt  37920
tgcaacgtcc tcccaaaaca tacacacaca cacattgtgg aagctgtagt gtgtcacagt  37980
gtgtcccaca gtgtagccct ctgtccacac atcttcactt gcaaatgtgc attgacatga  38040
gtcactggtc tatgttcctg gtctctggct tctgggacac catcaatact ggatcctcac  38100
cagaactccc agttattctg ttgttgccct gtgccatgga gaccctgcag ctttggaaca  38160
gcaggactgg cccttccatg catccaacct ttcacagatg acacagattt gggggtaagg  38220
cagttcagag ccctgggtgt gggcctgggg gatagctgag ctagtcagcc caccggctct  38280
ctgttatcca caccaccaga gcaagctctg gctaggttac cactcccagc acccacccct  38340
tcagagccag ctctgatgct gcccagttca ggttcagggc cctctccaag tactgtaacc  38400
ttgaggggct gggccagctc tcctgttctc acacccttag ggctggctca ccagtgcccc  38460
cttaaccagg tccatctgtg ctggtgtagg gctcactcat ctgagtgttg gagctggtga  38520
tgggcagcac taactctccc aaggtcatga ccctgtgggc agctttcttg agtgctggag  38580
gtgacgagga acaggggccg tcacctctgc atcagtccca tcccaaggca gatgagtaac  38640
ggggtcagct ctcccatatt cctgccctta gggctgacac acacacacac acacactgcc  38700
aggaccagct ctactcttct gtctaggcga agcacagggc ctgctttaca gagtggtgca  38760
cccaatgaga ggcagggcat cccctggata tccgcgtgat cccctcaacc tgatccagcc  38820
ctactgcgct gcccaggcaa attgtcgagc ctgctctcct gagtgctgca actggcgagg  38880
gggcaggtac agtgactgcc ttgaccagag acatctccaa gttctctagt ggtaatacaa  38940
accacagaca ttgatagtga cccctgtact acataggcat ggactcacac gtggtcttca  39000
gtggcagctc aggctgggac ctcgccatgg ccccaagtga caggcagggc tggccactca  39060
caacaagcta ctcctctcca tcctccagtc tctcgttcca tctccttcat catgcccaag  39120
```

-continued

```
ctgctccact tctttctctc tcatctgacc accacatact tgcatatcgt ggtggctcgt  39180
gctgcacact ggacacacag ctggtgggcc cctggacaag tcctccatcc atgttgcatg  39240
gtgtcgtggc aagtgtatgt ctgtggcctg cctgtgctgt gtgctggagg gcaggtctat  39300
ggatgccatg gtggtccaca ggtctctttc tgtgctgccc ggatgtgatt tggtttggtt  39360
tggtttttat gagtcctagg cgtaagacag ctttggccac caagccaggc tccaagttag  39420
aatgaataga gaggcctgcc atctgctctg ccccttggcc gggttggggt gggcaaatca  39480
atgttaaact cttaaaggtt tctggcgttt gtattctaca ctctgtgcac gttgtagtct  39540
tcactcgtaa ttttcaagtg caagggagga gcccctgctc ctgtgccagc tgtagtttgt  39600
agttatccac agggttttgt tttgttttgg agaaaaaata agatgatttg ctctagcttt  39660
gaagaaacga aaaaaactat gggctcctat cagcatggca aaacatttgt tgtgttttat  39720
ggctaaattg ctttctgaga agagaaattg atttcaagaa gaggaacccg tgagcaggac  39780
cacacagctc atttgagaag aggggagaaa cttgactcct ggggccttag tttttgtttt  39840
ccctttagct gatgtcaagt gtcttggact ctgctgttct tggggtagat gttggttgtg  39900
gttgttcaaa gcttggacag ggaggtggct gtagaaaggg ctgctttgca ggagcgaggt  39960
ctgccaggaa ccatgcccct caccacagcc tccattctca cctccaggcc gatccatata  40020
atgggtgcct tgtcaggaag cagggcagga ctcaatgcag tgtactctgg tgggaaggtg  40080
gacactgtct agcacaaatg tcttccacgt tgacatcagg gaactctgtg ggaggatttg  40140
ttaactcaaa gatgtgtgaa gttaccctgt caagtatcct aaagttgtat ttactctgca  40200
tccaacttag tatattcagc taaggggaac aaatttctgc tccaatgggc ctacctacat  40260
cactgaacca tccctctaga aagagttgtc tctgcattga catctgtttc ctgtaacttc  40320
ttgttttcct aaacttgttg tttgcttgtt tgtttgtttt tggatgtagg ggagggtggc  40380
atgtactata gtgtgcagtc caccgcactc ctgttgagtt caaaaaatat cttgtgggag  40440
tcagttcttc cttctaccac atagcatctg ggatccaat  tcaggttgtt ggccttgtct  40500
cacctggcca cctgtttctc tctccctttt ttgaaactct acaagacaaa gctactttct  40560
tgcctttgtc ttttctatcc agacagtttc attgttattt ctttaacagt cctccattgg  40620
ctcagctcac acttactgca cagctagtgt gggcatgatt tgttcttggt gcccagtgtc  40680
agacagaggc atcttgaagg gtaacgactg atatggagcc agtgaatata aaacatgctg  40740
tctgccagcc ctaacagtgg agacaaagag cagttaaccc cggtcacgag aaaactgtgg  40800
tttcaataag gtttcaattc cttatgcctc aaccaggtga tgcagttgcc aagaagccca  40860
gccggactgc ctcatcaccc tgtggatgag tgatgagagc caagaagtcc cacgtacttt  40920
cttcctgtca agcaagcctt agagtgcttc ggacagacag cagcaaacta ggaagtgttt  40980
ataaggtctc tccattgcca ccttgaagaa agccaccatg tccctggttc tgggctcagc  41040
ctttccagtt agatcaaatt gatcacacag catgatttca gtcccttaac tgtgcgaatc  41100
tttctgtgta taattaatat cgcctcttaa actgctgctc tcagaaggca cctggtgtct  41160
ccaggtgtgg tttcttctaa tgccttttga ctttctttcc ttgagctagg ttttgttttt  41220
tgtttttgt  tttgttttgt ttttacagga tttatgtatt tattatatgt aagtacactg  41280
tagctttctt cagacacccc agaagagggc atcagatctc attacggatg gttgtgagcc  41340
accacgtggt tgctggggtt tgaacctagg accttcggaa gagcaatcag tgctcttaac  41400
cgctgagcca tctctccagc ccttgagcta ggtttttgtt tgtttgtttt gttgttttgt  41460
```

-continued

```
ttaattaggc agttgacgat tgaggtaccc gtaaaagaat aaaagtagaa gaatgctctg  41520
gttggttctc agtgtcaaag tattgctagg ccgcttccct tgttcagttt attcctgtgt  41580
acagtatagt aacttagatt tctctctctt aaaattataa gttctttgct ttccacactt  41640
tattttctgt caggatctta ttttttaat ttgtttattt ttatgtgtgc atgtttggct  41700
ttttatgtgt ttttgtgctt tgtgtgtgtg cttgggaccg gtggaggaca gaagagggtg  41760
tcacatctcc tggaactgga gtttcatgtg gttatggcag ttaaataagt taactagtta  41820
atagttaata gtgagctgtt gagtaggtgc tgggaattga accggggtcc ttggggagaa  41880
ctgtcagtgt tcttaactgc tgagccattt ttccagcctg agatcctttt gaatattgtc  41940
tctcaccctt actttgccat ttgcagaact gataagcaca tttgcagtct tcatctaggt  42000
gattaattca attgtttcct taaatgatga aatagtacca ggctgttccc agtctcttaa  42060
gtgacttttc ttttaaaatg gcattgcagg gagctggaga ggttggagag gtggctctgt  42120
ggctaagggc atttgctgcc cttgttatat ggtggcacac agaaacaatt ataacaactg  42180
cttcagggga gccaacaccc tcttctggct gctgtgggca gcaagtatac atgtggtaca  42240
cagacatata tgcatacata catgtataaa tgcatgcatg caagtatgca tgtgatacac  42300
agacatacat tcaggcaaac acacacataa aataaaaata agtaaatcca ttttagaaac  42360
cacaaacaac aactgaaatg attttttttc caagatggca tggcagttaa cagtgagcac  42420
tcttgactct gtcatccaca gtctcatttt atccaagcat tgactgcagt ggcttcttgg  42480
tccttaaaga tgagacatga ccacaattta aagtagtcac ttttagctct tctctaactc  42540
attcattatc tggaatggtt aggtagaaat ggaagctaaa tctcttgtct ttgcacgcca  42600
ccctttcttc tggtattttc ctcttgcttc tggtaaacct taaaagaaag tgggaggaga  42660
ctaggctctg ccctgtggtc cgtgctgctg tgtcgactgc tgttgggctc tgtccagttc  42720
atctggcctc cgttcgggag ccacattcct tcttgtattc agtcttagtt atctgccaaa  42780
gcactaggga atgtgtttgg cttagttttt aacttatgat ctcaggtcag ttcaatccct  42840
ggggcctaca tggtaggaag agagaactga ttcctgtgag ctgtccttgg acttctgcac  42900
gagggctaca gcatctgtgc cccccccccc acacacacac aaaaataaat aagtaaatgt  42960
gattgacatg tttgctttct ttatgttttt caagacaagg tttctctctg cagccctgtc  43020
aatcctggaa ctttgtctgt agaccaggct gacctggaac tcacagagat ccacctgcct  43080
ctgtcctctg agtgctggga ttaaaggcat gcactaccac tttgtggctt atatcacata  43140
ttaactctgc ttaaatgact gtggctgatt gtgactttct tttgtttgag agggaggccc  43200
atatagctca ggctatcctt aagctcactc agttgctaag gctggccttg aactacctca  43260
cttacagatg tgcctcacca tgagtgactg acaatgtgac tttcaaagga gaattattaa  43320
agccatttct tgcctaataa agaagtccac tgagagtggt tcttaggctg agcagagggc  43380
caggtttttg tttttgtttt tgtttttgtt taagctacat ttaaagtaaa gaagctactt  43440
aatgtttatg tgtgtgtcct gaagaaaagg caccaacagt gtgtgaagtc tgtggacttt  43500
actccagggg tcctgtgtct gtcctttact ccaggggtcc tgtgtctgtc ctttacttgt  43560
aaatgatttt cagctgacaa gaagatgtag cagtcacgct tatagttgtt cagcatggct  43620
gacacagagt acatgtgggc accattgtcc acatgggctg atggtgaaat gccaccattg  43680
gggtggtggc tttgatggac tctgctcttg ccccacctgg acagactcat tttcagaagt  43740
gtctgagttt gcagggaccc cacacaatgc agaatgtcct cggaagcagg cagatccccc  43800
cccctccctt taagcaagac ttccgcttca ggtgatttcc ttgaactaac actcagcggc  43860
```

-continued

```
cattacagta ctgttatttc tgctcatggg attttgggtc atagccttaa aaggtgactc  43920
aggaacaact ggcatgattt tgttagattg gaaacatttg aatatgacca agctttttgg  43980
ttgaatgtat ctactttaaa ttcatcaatg agcactggag agatagctta gagattaaga  44040
tcactggctg ctcttccaaa ggacctgggt tcagttccta gcacctacat ggcactgcac  44100
aattatctgt gacttctggc ctctctgggc accaggcaca ctggaacaca aatatacatg  44160
cagacaaaac tcatgcatat agaatcaatt aattaaaaag ataaaattca tcgatgaaag  44220
caccttaata atagctgaag attaaattcc atttagattc cctctaaaga tcctgtgggt  44280
ttctgtaagg ctcctgccta cttcataccc tgctgttctg gtggctttgt gtcctttgct  44340
agttggtggt ccctgcaagg caagaatcac cacttactgt cttggctccc agcactggtc  44400
accgagggat ggagattgag aggaggatct gactttgagc tctcttgcct cagaatagga  44460
gatgctggga atggccttca actcttgact gtctagtttc ccctacttta gcctgcagtg  44520
ggtcttagcc ttggcatggc tgccattttg gcctgtgaga ctgttttgat gcctgtgcta  44580
attaattgtg tatttggtct ctaatcattg aatgctgtgc tctccacccc tcaaaaaatc  44640
tgacatccaa aatgtctcca gccatagcca aattcccctg ggagcaagga gccttaagct  44700
ctctggtaaa tgctgagcag ggccatcagc aaattataga cgttcagctt tggaaaggac  44760
tgaaaactat tgccctctgg ggcactcctc cctaccccag ctctgaatta gtgaatattt  44820
gaagaagaag aagaagaaga gggagaggag gaggaggagg aagaggaagg agaaggagaa  44880
ggagaaggag aagaagagag gaggagaaga ctgtatgtgt gttaagactg ggttggaatt  44940
gtatgattat ttggttcaag tttatttaca aaaggtgaac ttgttttacg gtaaacgttt  45000
ttacacttat ttatttactg tggcatgagc ggatgcatgg gaatcctggc atgtatgtag  45060
agaggtcaga ggacaacttg caggggctga ttttctcctt ttaccatgtg ggccgcaagg  45120
gtccaagtca ggtcagcagg cttgttggta aagcatcctt acctgctggc ctgtctcacc  45180
agccctaaga aagtacagac ttatatggcc ttattaacat cccaggaaga gtagtgtcta  45240
gacccactct tctttaaatg taagatacat agtaagcatt tctccagttc aaacgaactg  45300
agcaaactct atgagtcacc ggaacctgcc ttctggcgta gccctggagt actgtgtact  45360
gtagcttctt ggagagattt aagtactcat gtcaagaaag agacaatgat ttgattcccc  45420
ttcacctgtg ccaaaaaacc aacttggttt ttcctctctt gagaattgcg acgaggctca  45480
ttgtgtgact cctactgtgg gttgttgttt tataaggggc gtttgggtct tactaggttt  45540
cctcacatga aggtaagaac accaaattaa atattagctg cttgtggtta ttttaagact  45600
catctcaata acctagagaa tttggttctc acactttgta ctttctgatt acaaacagct  45660
tttaaatggg tttatgttgt ttttccatca ggacttacag agggtgggca gcggagggac  45720
gcttttggga ccaacatgag gcaattcaga gtctctcttg cgtgtcagct ctttctgctt  45780
tgatctctat ctattattct tactctgtct tttcaaagat tctgtttgga gaacttctct  45840
ttagcgagat cacaagagaa aaatggcagg acgctgtgct ctggagtcat ccacctattt  45900
ctgaggtagg gtaaaatctc actgacatgc gctttcttgg cctttggtgt cctgtgctct  45960
gtttagatgg ctctttttc ttttatttgg tttcaggtag accctagaca gtctcaccta  46020
gatgtaacac aaatgtctct aaaagttgtg gatgcatgtt tctgtgtaac tcggaaggta  46080
gcaggaggct tcaggagctg ttttcttcat gttttcttca tgttttcctt gcttcatcgg  46140
cagatcaggc tttcaatttt ctctgttctc tctttttgta acctctttta aatattaaac  46200
```

-continued

```
ttgatataat ctctctgaaa attttttga ctatgtatgt tggtgattta cttgttcaaa  46260
attaataact gcaaagcctg cctgcctgcc tctctgcact ttgtatttga aatctcttag  46320
cagggagaca tttttctcag aacaaatctt ttggcagaca tcaagaagtt aattattcct  46380
acatgaaatg ctacttggaa ctttttgaaa catttcaata tctatgctga tttaaccaaa  46440
agaaaagaaa atgggttctg ggttgaataa ctggggagtc ctggcagaca tgaccgtgtc  46500
agatgccttg gcacggcctc agggcagagg ggactttccc acttctcatt gtaatctccc  46560
atcttcgtat gtgggagttt tgtgaaggtc ctgtgtttca ctgaaatgct cagctttccg  46620
cactatgtat actgctctgt gagcacaggc tctgtggatg tctacacatg tttaaaagaa  46680
aatgcaaagg aatggtggag aaaggcgtca ctgtggttat tattagctca tataataacg  46740
tgatccttaa ctttgcagtc ggtcggtcag aatgtaaagt ggaacgctct gtagaaacag  46800
gacatcatgt gtggtggtga gggtggcagg ctctcagcat ttatttatcc catcatctct  46860
taatagatgt tgttgtgcag gccagagatg ttttcatcca agcagggtca gtggtacctt  46920
ggcatcaact tatgttcagg agtcaaagtg aaaacacagc taaaacacta atgaagtcta  46980
tagcttggaa aaggtgtctt ttaagtctca tcgtccccag tccctgcatg ctttctccat  47040
cacccccagt ttcaggtctc acaggcccag ctctggctac cctctgatgt cagggagctt  47100
cacgtcacca gacccctggt gccaaggtgg aggtgagaag aggagttaca ggcagttgtg  47160
agccaccata tgggttgtgg gagcagaacc tgggttctct gccagggcag accactgagc  47220
tacctagaag tcgttaaggt atcagtgttt gtgtcaccat tcaaggagca ggcagagtaa  47280
cagtgttggt gattagaagg taccctttt tcatttttga gtaaaaggat ctcccacctg  47340
ccaaccttga gtcatttcag aggacatcaa cgtcttgtca cactttgtag ccactgtaag  47400
tttgtcacca actttacaga agtaggtgtt gagatcctag actagattga agccagaggt  47460
agtctcctct caccctctct tctgggcatg gggtgtttac tgagcaggac aatgaagaag  47520
tgaggtgtca ggaaggacag gttccttttc ctccgtgggt tccattagtg tggtgttagc  47580
attgcagggc ttgtgttacg atgggcccag tggttctttc actgagtctc gtaaagactt  47640
ggagaacatc atttacttaa ctcctggact tcaattccca agtccccatc tatcttgatc  47700
cctacatatt gatgtatcat actctgtcta ctgtctgtct gtctggcagt cgtttgtctg  47760
tctgtctgtc atctacctat cttgaacata cttcccctct tagccccctc tgcctctttt  47820
ctcacccctc attcttacta ttagtccctg gccttcctct ccacaacatc ggaagattac  47880
atctcgaagc cctcttacct gtgagtcaca gtctcgctat gcttctataa ttataatcat  47940
caggcttttg atgcctactc tttttaattc aagatagcct tagccaagct gttaactgca  48000
gattaattca tatgctgtca tgataggcaa tttagcaatc catagagatg cagacagaca  48060
cagaggggga ctgactgtag agtggcccat tcttctagtt taaggccaac ccacctagca  48120
agctcatgtc aaataatgtg ggcgactata tattatacct taagagatct gtgtaaaatt  48180
gactatcgct gcttctgaaa aggagtaaga aagttagatt attataaaaa gaactgtagc  48240
ctttacaaaa gaatttaatc tcaggattct tcatagtagc aggatctcca gtttggttaa  48300
actgtaaaaa tgaatcactt cttagcattt tggcagaggt ctagtgtaaa atgcaccatg  48360
acttatagag gcttggcttc cctatgccag aaatgcagtc tttgaacagc actgctcagc  48420
atgagccctc tggggacatg ctatagggct tgagaatttg tgctgtactg gagtttgcag  48480
gcatacattt tccctttcct gtgtccctgc ccacacccaa agaagtgtcc attaaaatat  48540
ggatgattga cctcagctgt tgactgaggg agccacctgt agagttaacc tttctgtggg  48600
```

-continued

```
gataggaaca tggagggttt cgatgccagc actacctctc aatgatttta aacaaggtac  48660
ccaactcccc agagtcttat atttgacccg ttacatggga agagggaacc tcaactgaga  48720
aaatgccttt attagattgg cccataggca agtctatggg gtgtttttct tgattaatga  48780
ttgatatgga agagtccatc ccactgtggg tggtgttgcc cctgagcaag tggccatggg  48840
ttgtataaat atgcaagctg agcaaactag taagcagagc tcctccatga agtcttgcct  48900
tgccttctct aggatggact gcgattagat gtgtaagcca tgcagtccca taggaggaac  48960
aacaatatga accaaccagt accccaagag ctccctggga ctaaaccacc taccaaagag  49020
tacacatggt aggacccatg gttccagctg tatatgtagc aatggcctag tcggtcatca  49080
atgggaggag aggcctttgg ccctgagaag gctcgatgcc ccagtgtagg ggggtgccag  49140
gtccaggaag tgggagtggg tagattggtg agcaggggga ggggggaggg gggtttcaga  49200
ggggaaacca aaaaagggga taacatttga aatgtaaata aagaaaatat ctagaaaagg  49260
ccaagcgtgg tggtgcatgc ctttaatccc agctctctgg aggcagagac aggtggattt  49320
ctgagttcga ggccagcctg gtctacaaaa tgagttccag gatagccagg actatacaga  49380
gaaaccctgt ctcgaacccc ccgcccccca aaaaaagaaa gaaaagaaaa gatataataa  49440
taataataat aataataata ataataataa taaaagaaaa catctaagtc agaaataaaa  49500
aataaaaagt aaaagatgtg taagccaatt aaatgttttc cttccccaaa ttgctttggg  49560
tcatggtcct tatgacagca atagaaagca gaataagaca ggatctgaca caaagtgggc  49620
gctcagcaaa ggtcagcatc ttgccctctt tctgtgtggg cagctcacct gcagtgtctc  49680
tagccccata gggttgagct gtgagcctgg agcactcaca gtatgagagt gaagtacagt  49740
ggctttaacc atagcctctg gagccagaca gcctacatgt gcatcagctc actgtgctct  49800
tgaagagtgt cttcctatca gtacctcatt tgcctgctct gcaaacggag gctaatggca  49860
aatgttcgat tggactattg aagtccagca gcctctgagt cgtgtagagt gcagagaaca  49920
cgcctacagt gttgtgcagt gaagctcttt gtgttgttag agctcagtgt ggaccaggct  49980
ttaaaatctc atgggccgac agcaggcttc ttagcagcta atagctcatt ggaggaaact  50040
cttgcttccg aacactcagg ccttggccgc ctctttaaca agaggtagct gttctcttag  50100
aagctgccct ggtctttctt ctcttccctg ctccctgcat ccactctggc tggcttttgt  50160
tattaatgtg gagcagttga agtcattgac ttgggtgaag gccaggcagc attactgaag  50220
tcatatatta ctttcctgga ctggccatga gcaggatgat aggagtcggg ggccagggaa  50280
gccgcctctc taggcagccc acatgaaagg tgtgtttgtt ttctccatca tatttgtgta  50340
agtagatctg aagcccattc actgtctcta gttttcccca cgggctgctc ttctctgctt  50400
aggctgacta ctcctgtgtg tgtcgcatct ttctttgtcc tttgtgacgt cattgcacaa  50460
actcctgtct actaattgca ggtagaattg ttgagtgagc ctggctgtat ctgtaggcac  50520
tttataatat gctaggtcag gtctgtgctt tggtgttggc ttttgttttt ctcatgttag  50580
tggaatactg ctgggagaga gtccttagtg acagtcagtg aaagtcttcc tcctcggagt  50640
gtggttgaag cacacacttg tttgttctgc tctggtattt ggggcctggg aaacggcagc  50700
ggaatgttat taggcatttt cctgaacttc ctacctgctc tttgctggaa tactccttgt  50760
ttggctctgg aaaggttcca tgctttgatg agcacagacg ctcgggggat cggaggctgt  50820
tttgatggtc tgttggcatc atgaaaggag atattgtttg ccaggggaga tacagtctgg  50880
gaaagagtgc tcaaggatcg tgtgacctca gagtgagaca gaacagtggt ctttgcctgt  50940
```

-continued

```
gccattgagc ttttaaaaaa ttgtttgtaa ctaataataa ctgaatatac tggtgtagcc  51000
tcgggttctg ttttgggttt ggtgggaatg gggaagatgg cattgtccag acttaaagtt  51060
tcttttaact gtgttcgtaa atgattaggg gtggttttcc actgtgaagt aaaaactgat  51120
tgctactggc attagccact gttaaattgt gatgcgcatt cacttcatta ttatttcaac  51180
agtttcggtg gggctttctt ctattttctc aattcaagaa cagtaattgt gaatcataat  51240
tcctaggaaa attctacatc ataatgacca cagatacatg agaactacac ccaccccctc  51300
tgtttttgct gtcagtttaa taaaatctgg acatcactca ggcgtgttgt ggtgtttaga  51360
ccctgtattt tgacgtattg tggtagctgc tgatttgtcc tgagagtacc actgttgcat  51420
cctgttgcgt ccctgagaca ctgttgcatc cctgagagat ccactgttgc gtccctggga  51480
cactgttgca tccctgagag atccactgtt gcgtccctga gacactgttg catccctgag  51540
agatccactg ttgcgtccct gagacactgt tgcatccctg agagatccac tgttgcgtcc  51600
ctgagacatt gttgcatccc tgagagatcc actgttttgc ccctgagcct tctcttgctg  51660
tttatttgtg agctttctag agtccaatga ttcagagaca agagcttgtt ctatccctca  51720
gactactttt tttttatcct ctcaatacaa tgaaaggaga agtatattct tttagtgctg  51780
tggtattttt atacctagtt ctcttacaat atatatatgg atgaatgatg gacccagtat  51840
agtggtatgt ctttaattcc agcaattgga aggctgaggc aggaaagtct agagttcaga  51900
taaaaattaa atacacagtg agacttcatc tttaaaaaaa tctgtgtgtg tgtgtgtgtg  51960
tttgtgtgtt cactcatgca tgcgcatgta tgtacatgtt tctgagtgtg tccatgtgtg  52020
cgtgtgtgta agctgggtgt gtaactcggt agacacttgc ctagcatatg tgagaccctg  52080
agttaaactc tataaacatc ctaaataaat aataaaacca tatttgtaca atgttttcta  52140
gaaattcaaa ttcttacgtt ataaagaaga aaacaattat taaaccaatc atagaaaacc  52200
tgttaaaatg ttgagatagt tactttcata tacatatatc tttttccct tgcttttaaa  52260
gatagaatct caggctagcc ctgaactctc taattctccc gtgtctcttt ctgtgggcac  52320
cactgcatcc aacagccctg atcatttgct ttggaaaaat actttaaatg gtttggaaac  52380
ctaggtttat aaagcataat atgtgagcat atttcccaca tcccagacca ttcttggcaa  52440
atattattta aatagctgca tagttctgta tctgatatgc tttttcttat aaagagttag  52500
agaaaaatat gcactaaaat taaaaagcag ggtttgaaaa cgtcgccttc tcttcctttt  52560
taaagaccat ttctgtttgt ttgtgtgccc atgtgcgtgc atttatatgt cagaggctga  52620
catgggtacc ttcctcgttg ctccccgtct tactctctga gagactctct cattgaactc  52680
acagatttcg ttaaactgat tggcaagga tcccaggtcc tgcctgtgcc tcctcagagg  52740
taggattact gctattactt ggtgctggga attaaactca gatcttcata cttgtatggt  52800
aaacatttta ctgactgtac catctcccaa acacccctgt gccttttaaa taaaaaaatt  52860
aaggcgttgt ctcatggaat acaggctgcc cttggactcc tgatctccct ccccatgctt  52920
ccctaagaaa tgggtatgcg gctgtctttg tctccttgac acaagctata gtcagtgtgg  52980
aagagggagc ctcagttgag taaatgtcct cactacattg gccattgatg tgggagggtc  53040
cagctcactg tggatggtca cagcctgggc tgatggtcct gtgtgctgta aaagaaagca  53100
gactgagcaa gccatgagtg agaagcagca gtgaacagca gtccctcatg gtctccacat  53160
actttcctac ctccaggttc ctgccctgtt tgagttcctg tcctatctct tccttcaaca  53220
atgagctatg atgtagtagt gtaagcgaag taaacccttt cctttccagg ctgcttttgg  53280
ttgaggtgtt tgagcacagc catagaaagc ctaagatgct gggattcctc acctggaaac  53340
```

-continued

```
ccacgctcac ctcgtggttc tgttctaact ttaaaagtaa ttagtttcaa agtttgagac  53400
tatgcaaact ttatgtttat atacaaaaga tttacccttt gtaaaagtga caatatataa  53460
aacgtatgaa catatataat agaagtcttt tgattggcaa caattaatta gaataattat  53520
tttaattggc tattattcat agctattgaa tcagtacaat tttcaaataa tcaactttta  53580
tccccactta aaaaaaaaaa ccaaaccaac ctctgaaaca gtcttctctt tttatttgaa  53640
gtgaggtcaa ctatttttgc aactaacttg agtttatcta cttgtgatat agattgaggg  53700
tgtacctgat tgtccttgat ctcccaggcc gcataggaca agaaaggctg tggcagtgaa  53760
ggaaacggag ccagatggcc cccatcaagg gtgccaaacc tccagcaggg atggatgcca  53820
caccagacag acagggcagg aaaatcactt cttcaagtag attttgccac tgctgcacct  53880
ggtgcgggga gtaagcgtgt agattgttaa ggtccactgg gcaagcgagg aagaggtaag  53940
gacaccggcc acgaggccag gactggggt tggcagtcct tgggctctct gatgaaatcc  54000
acttggcatt ctcatagttt ttcaaaggaa tctgggtaag gcatttaatc ttgtgttatt  54060
ggtttagttg gctcttaaag gagagtcata attaaaccag agccatctgc cagtgaatct  54120
tagaggtgct tttcagtttg aaagttgaaa cccagagtca caaagccatc tcttaagcat  54180
cggcctacag ttgactgcat gttgctgtgg tttgtttttt ccaccaaggg agttgatttg  54240
ggagaaagaa tgtggttaag aattctatgt ccccaaagac atctgtacaa ctgctcccaa  54300
acttcgtttc taaaagtgac aatagtaaca cttattttaa aggtaagagg gaggttgcgt  54360
gttaaagcat agcactgact tggcctctcc gagatattag agactttgct attaataaat  54420
catggcgagt cacgagattc cacggtgtgg aactgtgctt ggatcactgg ggttcgttaa  54480
ataaagttac ttttcctttc tgagtcaatt acagtctcct gcccagaact acgcacggaa  54540
atgcaagtct ttatgaaaga tctccaaagc ccattgaact aaacaacaaa cccactttgg  54600
tttatttgct ctccccctcc ctctctccat ccttccctac gtctctctgt ccctcctgct  54660
ccttcctcca gcccaggtga ttccttccag cttgtttctc ttgtcattct gaaagctggc  54720
ctgaccttcg cagtcagata attctaattt cagctcaaga aaagggagac ggtcttgatt  54780
tgtgtggccg tctgcattca tgcccaatta tacacaacag tcatttgtcc atggctgcag  54840
gggaggctgg gagatacaca cgtgttctgt tagcgtagag tagggatgag ggatcggtgg  54900
tgccaatcgt gtcacctgta cttgcaaata aatcatgttg agacatagcc atgcccttgg  54960
cctgtggagg gtctgtgtct cctttcatat agcacagtga atgagctcag ttccctgaga  55020
ccatatagac ttcaaagcac accacattta ctgtctcgcc cttttcagac gcttgctgac  55080
atttgctagg gaaaatggag aaatgaaatt ataagagtca ccaagagttt gtgccacact  55140
ttgcagctta gtaaactgtg agccattgcc atagctggga ctttgtgctt ctgaagagtg  55200
gtagccaaca gaaagcacgg ttgatttgaa gtaacgcttg aagaagcact gttcagagat  55260
ggatttttgg agcaaagcag gaagttattg gtgagggtga agagagtata aaacgttgtt  55320
tagaggagct agagaaatga acacttgcca ctcttccaga ggatctgagt tcagttccca  55380
gcacccacat caggcagctt acaactgatt ggactttatc tcctagggat ccaatgcctt  55440
tctgtagcca ctgtgggtaa acacacacac acacacagga ttttttaaaa gctttcatgt  55500
gaatttctgc ttttaaggcg acaggccata tttcaagcgt atcctcatct cctgcatccc  55560
acagattgtt ctgtgttttt tctttgcttt cttcatgact ggggcagaag agggatacat  55620
ccataggagg gcatagacgg tatctccact ctgcagctgg gttcatttcc ccaacttcag  55680
```

-continued

```
ggtgtgccag ggagcagagc ggcataagga ggatcataaa agctgagctc cctgtgagtg  55740
acagagtgct gcccaggcca cttggaagga caggaccttg cccacagctg gtgtcttgtg  55800
tgtccacagc cacagtcaag ggaagggggg ttttgatttg gagagacatg attggccctg  55860
tgagctgcct cttctttcct tagtctgtat aaccacgcat acaatgagga gactaataga  55920
taatgagaga cttgctcctg ctgtcaaaga cctcccgtcc ttcactcagc tcatattgat  55980
taaaacctgg tgagcttggc cacagcattg gaaagacagg tggacgacca ggaacttcta  56040
aaaggatcag caggagagag agaccccgag atggggtgct ggggtttccg ctgagtccac  56100
tgtgctgctt gaagcataaa tacaaggggg cttccagacc cctgtgacag agggacacct  56160
gtctgataac ggaggaaagc agaggtctgg ttccttatgc tttggtgact ggagctgttg  56220
aagaacaaaa gcagattaat gtagaatttt tctcaagctt gacttaggat aacaacaaga  56280
tggacttttg ctaatgtgca tccagcccct ggcagaacac tctggagaca gtcagtgctc  56340
agtacatgtt tgttgagtga ataaattagg tggattttgg cacttaatta tcagagcttt  56400
ctagaagatg aaaggattcc ctagcagaat gatgttttta cagagaaaaa ggcaaaaggc  56460
tcttatcctc caggagcccc tccttcactc tctcatcttc cacatgttca tgtctcactg  56520
gcccctcctg ctttcaggac tttgggagag taatggcgtg tagccgcctt ttatcaggag  56580
agcctgtgtt atttaaccac gcttcatggc ccctttgtag ccgacacaga tggcagaatg  56640
agttcgtttt taataatcta ggttttatag gaatgaactg tggtgtgaac tgcttggcct  56700
tccatgagac gaagtagaat cttgtctgtc tgactatcta ttgtttttgt gtgtgtgtgt  56760
ggtttttcga gacagggttt ctctgtgtag ctctggctgt cctgggaatc gctctgtaca  56820
ccaggctggc ctcgaactca gatatctacc tgcctctgtc tcctgagtgc tgggatcaaa  56880
ggcgtgcgcc accaccactc agcaacctcc acagaatttc tgaacagtaa aaaacgtttc  56940
cttctgaagc tgcttccttc agagtttttg agttttacat aaatctgctg taatagttag  57000
attacggaac tggtgaaatg gcttagcagg taaaggtgct taccagtgcg tgcagcaagg  57060
cgtgcgtgca gcaaggcgtg cgtgcacgtg cacaggagtg gacacacata gccttataat  57120
gtaataaaaa gtaagcagta cattaagtgt atttgtgaac aagtcaaata taaatccctt  57180
aattctaagc taatgtttct ggcccagatc catgagagag tccacagagg aaaaatgtca  57240
gagagaaact ctgtgtaaca aggaactttc cctgaggaca cagcatctgc agtcactggc  57300
tgtttgtgct ctgcaccacg caggcctgca gttgatcatt gtaccagact gcactactat  57360
tgaggggaca ataagacatc cagcccatca tgtccctgtc tttatttcaa agcagggaac  57420
aatagcagct cttgtgccca aaactcacgc atgagatagt ccatgggaca cacctgggac  57480
agcctcacat gtagtaaggt actgctccca gccacgacgg ctgaacagag acttcaaaat  57540
ctgacccaaa gcagctaaga ctgctttgcc tgctgcccca atggggagga tcttgctggc  57600
atgcactgta gcgtgccgct tgcaggcatt ctagttcctc ccacccgttg ctccagctcc  57660
cagcctctgg tagagccatc ttcatggtag gagctagggt gtgctatgcc tgtgtctcag  57720
ctggaggcag agggtggcct gggaagtcaa actgctgaca gtgttcatgg cacaacttgt  57780
gtatttttag gaatttgtgt gtctctgatg aggcaagctg tttacttcct acttaatgtc  57840
taacctgaat tctaggcctg aatctagaaa aggtacattt ttgccatgct gtgtctgttg  57900
agagactcgg gttatcggtc cacaattgac tgccagagag actgggaagt atccctgcca  57960
cctggatttt tgtatgtcca gttactgcac attctcagtg taggaaatat ttattaaaac  58020
agcatttcgg gtaaggattt agatgtcagg acaaggaatc gcagagctgt gccacaggcc  58080
```

-continued

```
ctgtatctcc catgagataa taaatccttc gaatattgaa tttaaacttg gggaaatttt  58140
tggattacag tgactctcag catgtctata atcctgggaa ttggaggtga gatgcaaaat  58200
ttgagggcac cctcaactgc ataggggata caaggctagc ttgggctaca tgagaccctg  58260
cttccgaaag gatagcccaa aaggactaag gatggctgtg agcacttgag tctttctaaa  58320
gtcatgtcta aaatattgct taggtggtat agcctgtatc tcctccattg tgctgttgag  58380
ttttagaatg attttattct tcctgactgt gattggacta ctagttgttc cccaatgccc  58440
ttagcctctt aacgattact ggtgtatgtg gctgtatgtg ttgtgaactc tttggcatcc  58500
ccatgtaaga gaggacatgc gacacttacc ttcccatgct agactaacta gacataacat  58560
taactaatta gttaacttaa ttaacttcca gctccatcag tttcagtgcc tatcataggc  58620
tatcatttta gtaactgaat aatattccat tgcatacatc ctgaaattga tatgtcattt  58680
ttccatatcc atcacaccaa tggtcatcta aattgattac acatcttgtg aattgtgctg  58740
ccacatacac aaagtaacaa caaggatgga gacattgatg accctgactg tgtcagtaca  58800
catcgtatac atcgtatgca tgcgtcgaaa cattgcgctg taccctacaa acacatagga  58860
ttattacatt ttttttcttt tttttcagga ttattacatt aattgaaaga aatgtaatgc  58920
ttaaggagta catattttac tactatgatt tgatcattat tggctgtctc cagctatcaa  58980
actgtagctc tgaacatgta caattaacgt aataactagg agagtggaaa caccttggaa  59040
ggcctgctct ggaataagcc taacccagta tctgacctgg caagggcaaa gtacatagaa  59100
gcagggtagt ttacttcaga gtactggagg ggaggcgggg accgggcaag gcatggggct  59160
ttcgagactt gacttttctt gttcagatca ctgctgtgta tgtgaaggag acaatcacac  59220
gtgcatttac tgtagttttt cttccccatg tcactgtccc ccaggagaca aggggttgaa  59280
gacacaggtt tctgcatcta gaagaaagga attcaggtta gacattaggt aggaagtaaa  59340
cagcctgcct catcagagac acacaaattc ttaaaaagca gacaccttgt gccgtgagcg  59400
ctgtcaacag atactgtcac gtggcagtaa aagcctcagg ttcctgcctc gtccatgctt  59460
agaaactgct gaaaacggaa ggactgggaa agatgactct tgacctgctg tgtagggttt  59520
tagaaccgtc tggaatagtg ggtagtaaca ccctgggagc tttgtgtgaa cgtgaagccc  59580
tgcactggct aagaagagaa gaggtgactg tttctggttt ttataagtac cctcttgtct  59640
aactgctaaa aataactgct gttactttaa acagatggcc tcaatttaat atgaaagaaa  59700
gtaaaagtga gacagtttct tagcatctaa gaactaccac ccccactggc taaaatagcc  59760
aaattttata taaatactta tttacaggga aaacttctga gggtggggtt tgtagatgga  59820
gctatgtatc ttggtagatt gagagccagt ataaatgact taattcaaaa cagaacggtg  59880
gatccttgcg tttaaaacaa ttattatcat tatgaggtgg tgcacaggtg tggagatcag  59940
aggacactct gacatgggtc cctggatcaa gatgagatca ccagccttgt gtggcaagtg  60000
tgtttcttta cccaatgagc cctctcccca gtctaggact ttggattttt aaaagacatt  60060
taagttgtta taaaatatat gtaacctaag aaagttaatg tcagggatcg taacacactg  60120
agagggtgag agagcacgcc gaggttattg ttttaggtcc tctccaatgg ccaaagagaa  60180
catgagctga tagggttcaa ttccaggagc acggagatag tagttaatgt acgactttac  60240
gtcatttctg acatcataga taatattttg ataaggaaac agtgagccag catttatgag  60300
actttgacta aagactgatt cttaagttca cagacactgt ctatgtcatc gagtaatgcc  60360
aaaatactat taagttcaac aggtagagaa gttttattgt gaaactcggt cattgatttt  60420
```

-continued

```
ttttaaaaga tttatttatt catttaatgt atatgagtac actgttgctg tcttcagaca  60480
caccagaaga ggccatcaga tcccattaca gatgtttgtg agcctccatg tggctgctgg  60540
gaattgaact caggacctct ggacgactag tcagtcagtg ctcttaaccg ctgagccatc  60600
tctccagccc agtcattgat ttttattcct acttttgctg ttcatttgtg attattgcac  60660
ctggttcttg tgcggggagg ggtgctgtct gtcctgtgtg catccatgga ccacagaccg  60720
tgcttggatt tagatgtttg catttcctca cctggcctgt acctgcacag ttgtttgtgt  60780
tgggtcctgg gttgcgcctg gaatcttact tgtttccttc tgaacttgtc tctgtaaaag  60840
aagtagactg gctcatagga aatatgaggc tggggaggcg gcactctgta agatgtcagg  60900
ggcacaagtg tgaggacctg aatttgcatc cctagaatgc ttgtaaaaag accaggcttt  60960
gctgagggag ccagggaccc tggggaggaa ggtgggtagg gtatggagtt aggtcggatc  61020
cctgtaccta gttggccagc tcttaccttt ccaacttcat gggcctcagt tttagtgact  61080
gatacaccct gtctcaaaac caaagaagaa cactggagga aagcccccgg cttctggtct  61140
ctgtgtgcac tggcatgtgt gtgcacatgc accgacatgt tcacattaac aagtgcctcc  61200
cctaccacac cactaccctt acacacgact accacacacg tacatgtata tacaaacaca  61260
cacatgtaga ccagagatca gcaaagtgta ctgctgggct atataaaaaa ataacatgag  61320
acagatattt gcagtagtta gcctttacaa aatgtttgct acctcttgaa gacaagatgc  61380
tcgtgggccg acgctggttc agatcttggt tttaccattt ccagttcgac ttgggcaaat  61440
tacttaatct ctctgtgact agttttccaa tctgtaattg taattatagc ctgcctcatt  61500
gggttgtggt gaggactaac ttaatgtaca aaatgctcag aacaatgtct gggattaatg  61560
ggtgctcaat gaatgttagt cagtgctcct gtgcgggaga gagccccgaa ggagcttctg  61620
aaccattctt ggtttcagct ggtacacacc caaattatcc agcccactcg ctctgtggtt  61680
cctgtattga gaagggaagg ctgtcttgtt gttgttttgt tttgtttttt atttttaaat  61740
agtgaatgcg ttcctgaaaa acaaagtcaa gttgaatcta cactgaaatg tgaaaaataa  61800
tcttgaaaaa aaaaaaggag acataagcag aaagcagaga tgctttgtaa gttaagggaa  61860
gtcaaaggtc gcttgtgctg ggtgtgttgg cacacaggtg gcttatcatc tcaggactct  61920
gaggctgagg agagagatga atgcattcca ggcctgcctt gcctatgcag taaagacctt  61980
gcctcagaaa gagcaaacac aaaagtcctt tgctgtactt tggtaaagca acttgtgatc  62040
gtgagagatg gagaggagac agtggcgggg gcgaggggga gtatctcagg ggaagctggg  62100
gccttctcaa gggtgtccag tgtcagcatc cacgaggcta tgcagagtgc cgtgtgacca  62160
ctctgcttct tttctatgga agtgatacat tttcagcatc aaatcaacca taggtggtaa  62220
aggtcacctc agacccccat gtatacataa ttgtcatagt ttgcatcttt agtttttaag  62280
acacctggct agtcactcag ttgctgtcgt catcaaacat ttgatcagcg tctcaatgcc  62340
tttgtcctct ctgatacctg tctcctcgct tgggctttcc agtagggaaa ggacaagtaa  62400
ttacttagaa ttttttaaat ttaataaagt aatattccct ccctctcact ctccttcttt  62460
ccactctagc tgaacacgct gttgatggat attggagtgg aatgatgggt ggccagagat  62520
gggtgtttga cgatgtcaga ggactggagt aatggccttg cgtgaggagt acagtgaatg  62580
acctcatctt cttagctgat ggaggcattc aagaggacga ggttgcagag cttttaagcc  62640
tatgcagctc ccaggctctg agcctaagag ctagctaact gtcatctccc agagggacca  62700
tggcaagggt tggggctgtt gaaatacgtt cagggaccct gttagggcct ttctctttga  62760
cattaggatg atttagggaa ggttgggact tacagaccag cttgagtttt cttttgtggc  62820
```

-continued

```
aattatagac ttaacttaaa agatcagttg tttttgtta gtgtcctctg agtttgggtt  62880
tgctgacgca gatacacact gcttcattag agcacctccc tcccaaccat gacaacagtg  62940
gcactcgtca gtactcaata tgttatttct ggagtgagtg agcggatgaa tggagtaaac  63000
aaatataacc cattattccc aataaaatac ctctcccaca tggaggtaag ttgtcagttg  63060
gcattatttt agatcaattt ttgctattaa aaaaaaaaga gtgttgtaaa ttttgagtat  63120
gccagaggga agctcaactc gggctttcat ggtttcccag ggcaaatggt gacttgatga  63180
gatagttaaa acacagcaac ccaggcagca aaggctttgg tcagaactct taacctctaa  63240
gactatctga gagcacttgg aaaagcttgc tgttctcttt gttctaagat gatagtgcag  63300
caagaactaa aacaactttg agacatttct ctttcagaca aagcaaatta taaaacatga  63360
ttaaccatta catcatcata cgtcctttaa ggcctgactt ccacaccctt cataggccct  63420
ggacagaaca agatgaacat ccaaggtgga aggcatgctg tagggatctg ctggctcatg  63480
ggtcaggctt cctgagtgga caagaggaca aagggtagat tccagcagaa cctacctgca  63540
tagaattgct aagtatgtgc atgcattaga ggggatgcat attagtttag tcttgctgtt  63600
ataaaatacc ctgaccaatg aaacagctta caggaaaaca agtttattta ggtttataat  63660
tctgaagggt cagagtccat catggtggaa aagagatggt tcctggggtc aacaacaaga  63720
aactggtgat cacacagcat ctgcacttag gaggtgtgga gagagaggac aggaagtgag  63780
gccagactat aacattgcaa agctcaactc ctgtgaccca cttcctccaa caaggctttg  63840
cctcctgggt tccatagcct caccaaacag tgccaccagc tggggaccaa gtgttaagcc  63900
acagaagcct gtggaggacc cttcgtattc aaaccctagc agcctgtctc tgagagcatt  63960
cacccttgat tgacatgggg aacacgacaa ggacactagg ctagcagaaa agcaaatata  64020
attctagacc ttcttggggc ctagggaaag tgcaccctgt gactgcactg ttgattgaaa  64080
actgatgcaa actttagaaa taaaagggaa aatgtcgggg gctggagaga tggccagtgg  64140
ttaagagcac tgactgctct tctgggggtc ctgagttcaa atcccagcaa ccacatggtg  64200
gctcacaacc atctgtaatg agatctgaag ataactacag tgtacttaca tataattaat  64260
aaataaaatc tttaaaagtt ggggggagga aatgtccagc tagtgctaca caagtttttt  64320
tttttggggg ggggggcca aggggttgac ttaaataaag ctaatggtgc cagagaaata  64380
aagagcaggt taagagtggc tccactccac cttgccactt ttagaagaag ggcaaggcgg  64440
gttacaaagc ctcaaaacaa gtctggcatg attgactgca ggtgagtgag catgttgttc  64500
aacttgtaaa tacnnnnnnn nnnnnnnnnn nnnnnnnnnn nnnnnnnnnn nnnnnnnnnn  64560
nnnnnnnnnn nnnnnnnnnn nnnnnnnnnn nnnnnnnnnn nnnnnnnnnn nnntttttttt  64620
ctccctccct cccttctttc ttttctccct ccctcccttc tttccttcct agcgtattca  64680
ccataaaccg aattaactcc agatatttca actactcctt tggtttaggt gacttgagag  64740
acacaggaaa gaaaaataca aacattaaat ggcattttga aaacctgttc ttaagtccag  64800
tgggcatcag agcagttgaa cagcaggtac ctgggagcac tctggtgaca caggttgaca  64860
cctttggaag gaaaggaatt agtctgccca ctcctcccca caaacagatg ggcagagatt  64920
ggcaggtgag gtggagagaa gaggggtaaa cccaggctaa ccgaaagggg agatggctat  64980
ccacaaagag aaatcaaagc ctaggcacac ttgtgtagaa ctgggaacca ggatgcctgc  65040
gacagagatt acggtattgc cccagaagcc cttttatact acttgatgtt gtgtgtatgt  65100
atagatttta tagaacaact taaggtaaac atttacattc ggtacatgtt atttaatatt  65160
```

-continued

```
aatatttaat agtttgtgcc ctcagtttgc ttgcaaatta tgattgataa aagaagttta  65220
attcagaatc tataaaaata ctaacactct atgttaaaaa aattaattcc tggaggtcag  65280
agaaatgatg acctaggttt aattcctgga actcatataa aaaagctaga cgtgttagtg  65340
aatatttata attccagccc tcctggtgtg aggtaggaga ggcaggagac tctctaggct  65400
ctggagccag cgatcctgga ctacagcatc ttggcagaag caaaacaaag accaaggtga  65460
gaagggactc cacacatgtg cacaaacaca tttataaaaa tgggttcttg aatgaatgat  65520
ttgcatggtt attttttgc agtataacta cctaggaata agaatggctt tcccgcgtag  65580
cccagtttgc tgtttaacta taaatacacc acttgtggca aatcggacgt ccaaaagcaa  65640
cagctgctgc ttctgtgttt tgttctttgt tattcatttt aatgaataat ttgaaccgac  65700
tccagaacat gaagttagac atagaagcat gctctaagac ttatatcatg tgtttcaaac  65760
cgtgtggtga catcattctc taaatatagt gaattttaag aaagaattat ttgagctgtt  65820
cccccccccc cccataaata atttggctgg aagacagaga gagagagaga caagggataa  65880
aaatcaactt gggagcttta tccaagaata gagagctggg gaaattctcc cacatccttc  65940
tcctgacacg tgaacctctt ttactaaaac aaatgggggg gatgtgtctc cgctgagatt  66000
tgcttttcta gtgaagatcc caagtgatgt taggcgtatc ccccctgcc ttccgtagtg  66060
tgtcctgtag ctgaaggatt taggttcagg tggaatagag aggaagatgg attcagagct  66120
tcgtgattgt gattcctgtc tgtctctcgt ggcattctca acagttgaaa agcaagaaaa  66180
tgcagccttt atcttcctat gtcctgggca tttgcttggc gtatatatgg gctttgtgtg  66240
ctccatctgc accgatttca gcccttcctt caggaaagct ggtaggactc attcaggtta  66300
acactgcatc ggtgcaaggt gtggtcgcag atcagcaagg ctgatttcct ttaaaacctg  66360
ctaaactgat tggtccagta tacttcagta gaaggtgata caactgttaa ttaagtaagc  66420
agttttgtac tttgattaga atattgttgt atgccttttc tcactggact gctgtacagt  66480
gttgagaagt ggaattccta ctaatgcaga aggagtttta tgtgccctta tatatgggga  66540
gaaatttaga attgcctctg gagagtggtt gcttaggaac gaagaaattg aaccacccat  66600
cacttaaggc cagaaactct atcctgtact tgtgtcctac cttaggcatc atttttctgt  66660
gtttcgttct gttcaagcct cttatatagc tgtggctggc tgtcttggat ggaaacccat  66720
gtcgcagtcc tcaggggtgg agtctccaga tgggctgtgt acgccggccg gccagcagcc  66780
ctgtctgtca tcctgtctgt caggaactga gtgtgtattc gtgaggaacg ctaatataaa  66840
aggcagctgt gtttaaggat gaggtcatag gcaaaccatg caccccctct ccacagaaca  66900
cagaaggatc ccaacggaga taaatatgcg tctggaggag ccacaccacc ttgcctgctg  66960
ccatgcctgg cttcattcac tttgcctgca cctgcggaaa gcaaacccga gagccctcta  67020
tgcaaatgtt attttaatta ttcatgttta ggacatatga aaaacaaacc tagaagggcc  67080
atgtctagat gctggcatgc cagtgacttg ttatcttatc tgtagagaaa tccacatcgt  67140
atctagatac aatctagaga tgaggggttt tccttacaag gtaatgatca ctgtccaaag  67200
gtgcgagagt aagtggcttg cccaaggtgt agacatgtta agtctctggg tcaaagtgct  67260
taccacagtc acctcccttt tcttggatgg tggatctgta gaagatggaa gcttcccctg  67320
gttttatgtc tccttttctg ccactgtcct gtatgttttt cagattcgtt ttgttgttgt  67380
cgtcgttgtt gttttgtttt gtttttgttt tttgtttttt tccagtgcaa gcctattgta  67440
agcagtccct gtttatgggc agtccactag ggggcagaca tgtcctcatt cactatgtcc  67500
cagacacttg gggcaagtct tcttacatag ttatgcttca tataatggtt tccagtttgc  67560
```

-continued

```
ttttcctgta tttgaggtat attcctatct aaaagttcag tggtaattcc tcagttcgtt  67620
gacagtgtct cttgtttttc tgttctacgc atcaccctaa aggtcattta tttattggtg  67680
actgtcttca tgcttagcat tcttctgtgc ctggggatat taaattctct ccttcacact  67740
ccattttgtt gggttattgt gtgttgggct gaataaaatt aatctgggag tagactgggc  67800
tgtgagtgag gaccagaacc tgagtcacac acagtaggta cagtggcctg gaggccatct  67860
gctgagagga ccaagctgtg agggggtgaa aaggggaatt catgataagg acagtgctgt  67920
ggacttttag ctctggttat tctttataag atgcttagaa gaacgggcct tgctgagaca  67980
ggggggttgg aggttcaact ccagcctaca ctgcttagta gaacccagtc tccaaagact  68040
gagggctggg gggtgtggct cactgtgggg gacccaccta acatctgtga agctctgtct  68100
ctagtagctc agtgtaggtg accctcctag catcacaaaa ctccgtctgc agccgaaaac  68160
tccagcagtt aggtacttga aagcatgtgt gtgtgcatga ataaaaacca gatcagaata  68220
tggaaaatgt tatttattgt aatattatct atattcacct cataacttat cagttttact  68280
attaatttct tcaaagtaaa cttgataaag aaaacaatac tccctgcaga acagtaactc  68340
agaatgtttt cccaaagccc tggcaactt tcagaaagga aaagtacacc acagtaattt  68400
aagagttgca ggtatttgca gtttatcatt tggaagtata cagctgagct gtgacaaaag  68460
attctctctc tctctctctc tctctctctc tctcactcac acacacacac acacacacac  68520
acacgttaaa attttaaggt ttcttgaaat gacagaggga tacaatataa gtcaacagtg  68580
tctgagcggg tatctcgcag tagctcactc actgatgaaa tgctgagttg gctctgcctt  68640
agccaggctc cctttgagat cccgctgaga acagtgttgg gcttttattg ggaatacttg  68700
ccctgattca cctgagaaca ccctgctcct caggaacaga gctagaagct tgatgtggtg  68760
gtgcacgcct ttaatcccag cacttaggag gcagaggcaa gcagatctct gagtttgagg  68820
ccagcctggt ctacataggg aattccaggc caaccagggc tatgtagtga gaccctgtat  68880
agaaaaacaa aaggaaacaa acaaaattac aggattaaga gttcaaatta ctgtctttca  68940
catgtgtcag atggtgtgtg gggacttgca tatgtccatt ctccatggct tatctgtgtg  69000
tctctctgaa gcttctgtgt ggggaacgaa gacagggcag ggggcaggga gcacagggat  69060
agagagtgga aaactacaag caggacactc cacagaggtc gggtcctcca tcaagtacgg  69120
ggcctgagat ttatgtaatg ttagttaaag ggaggcaaag tggcattctt cctatttgct  69180
gccccccttcc cttgtcccaa gtccactcct ccttcattct agttaaacat caacgatgac  69240
atatttaaag taaaacagca aaatgtgaga atctctcgtg tcctgtggga tgtctggaga  69300
catgtcacaa acccaaagcc agccgctgca gtctgaactc aggggctata tttagatgac  69360
tgtgtggatc ctgtattttt tcagtgctgt aaacatgttg atgtggttat ttttagcttt  69420
cacagacctt agtgaacttc tgagttggcc agcagacaga ggcagttgtg gctgttgccc  69480
gcacctctgt caatggctct gattgtctct cagggtttcc agtgcattca gagcttgtca  69540
gtgttcaggc tgtctagcat taactgccca gtgtggttgt gtgtaggtga ctctactaca  69600
gtctggtggg cttcatttg ttttgatgtg tgtctctggc catagttttg attccagttg  69660
aagatatatc aagcccactg gtcctctcat gccctgaccc tccagcattg atgacagatt  69720
cttgctgttg tcattacctt cagtctgttg tactcttttc ctgctgggca aaggttataa  69780
ggcggcagtg tggtaaaggg ggcaatggaa agctgacagg aaatgggaag gcagggctca  69840
gtttggtccc cagcatagat tggaccagct agtgtgaaaa gaagtaatta agtagtcaac  69900
```

-continued

```
agcttttctt gatgaccaaa tcatgctgtc tctgctgctt acatgagtgg aacattttcc  69960
tcgaagagcc atgcctggat ccctgacatc gattagtcac ttgagctggg ccttccaagt  70020
ttgtgttaga gaattcactt ccttctttgt gaagaggctg ctgttctgag ctctgctttg  70080
tacctggtgg ctggctttgg ttggataagg tcaattactt tgtatggtgc aggaagcagt  70140
tcctgagcgg gtgactcgag agagcatgat ttatctcttt ggaactactt ttcccaagga  70200
aactcataac tgcctcatac cttttgcctg gaagccttaa actgagttgt acattcagaa  70260
gagagtggta ttgagcgtca tccagactta gttcatatta ataccattat ggcaatttgt  70320
tttgaaatgt tttcagtgat tcatatgaaa gtgatgtttt tgaactgtgt cccaattttt  70380
aaaattattt gtttttgttt gtttgtttgt ttctatgggt atgtttgtgt gcccagtgca  70440
tgcatgccca ccacatgtgc aggacccctc agagtttaga agatggcttt cccctggagc  70500
tggagttaca ggcgattatg agctaccatc tgggtgctaa gaactgaccc caggtcctct  70560
gctagaacgg tgtgtgccct tgactgacga ctcacatctc tggcacccat gacctctggt  70620
tcttactgta gcctttacac attgtaaaca cgccacaaaa caaaacaaaa caaaacactt  70680
gacaggaagc atgctttttg tattttgctg aaaactcaga aacaaacata cacattttac  70740
cacagaaata tatattttgg atttggtagg tgaacaagaa atggaattga gaaatccaag  70800
ggttttagca aaagataggg ttttttcaaa tgtttttatt atgtgtaatt aatttgtatg  70860
tgtgtttttt ttttttaaag atttatttat ttattatatg taagtacact gtagctgtcc  70920
tcagatactc cagaagaggg catcagatct cattacggat ggttgtgagc caccatgtgg  70980
ttgctgggat ttgaactagg gaccttcgga agagcagtcg gcactcttaa ccactgagcc  71040
atctcgccag cccctgtatg tgtgttttta tgtggagcct tgtgcacgtg tgtgcaggtc  71100
cctatggagg ctgggagaga atgttgtgac gtctgaagca ggaattacat gtgagcggtc  71160
tgacctgggt gctgagaact cagctctggt cctctggaag atcaatactc actcttgact  71220
cctcaacatc tttccagcca gaagttgaaa ttaaaacaaa acaaaacaaa aagaatcaag  71280
attgctgtta atgttttgat gagctttttg ttgttgttgt tcattttggg cttggtttag  71340
ttttgagaca gggccctgta tagcccacgc tggtcttaga tttactctgt agctttgtgt  71400
gaacttttct ggggggaaaa ggggtctatt caccccagaa aagtaccaac catgaactga  71460
agatgtgacc ctcccaagtc taacagggtg aaccagtgtg cttaattagg gttacttaaa  71520
ggcgtacaga cactttgcaa gcaggcaagt gattatacca ttgaagaaaa cgtctctttc  71580
tttccagcag ttttagctgt cagtcagtct ttgatgatga ctgggtcctc aggagccctt  71640
gccgtcctct gtggctccat gttataggct caggcctgtg tagaagccta tagacagtca  71700
cagctgccaa gaattataga gggtaatggc catgccacag ctaggagaca gccttgtaag  71760
catagagttt gaccttgaat gagatgcttc tatttccatt tcccaaatgc tgagatctca  71820
tgcgtgagcc aacatcccag gtgctgggtt catgctttct aggcatccac cctgacaact  71880
aagttacagc ccagcccagg acagacaggg gttgggatat attgctactg gtcactatgt  71940
agaccgggct gaccttgaat tcagagatct gtctgcctct gtttccaatt ctattggcat  72000
taaatgtgtg tgccaccaca tcagcaccat ttttttaaaa tccccgttta tatagacaag  72060
tccattgttt tcccaatagc agtggcagta acccaggtgg catgcatttg tggtgcatag  72120
taggcacccc agtttacagt cgagcatagt ttaaacctcg atcattgtag gtctcatcct  72180
ttggagccgg gctttgtaac aagatgctgt ctcgaacatg agttacagaa ttgtcatttc  72240
aagctgtaat gtccacatga cagcttcagg ccacagcagc caaatctaag tgaagtcaga  72300
```

-continued

```
aaatcagctc tctgtttgtg acagtcacta atgttctggt tctgtcgctc agtgcctcct  72360
ctggcctgtt tgggactcat gatgatgctt gtaccctgtg gctctgttca gccagattgc  72420
ctgggtctct acctgggcgt tcaacccacc tctgcctttg aagccgtttg actttgtggt  72480
agttggtggt ctttggtggc catcgttaga atccctcacc ttccccacac ttggctagcc  72540
tgcttccatc caggccgagc atgtatgtaa actctgatac ttcagaagtt caccggacag  72600
ttgggagcca ggagcctgga gccaggcatt ggtctgcagt tttttccagt gtattcgtct  72660
gtttgtatta ctaagctaaa gttagcacaa atgggacaag gctagaaaat ggtgcgcctg  72720
gtttgaaaac aggaagtttt aggcttctgt gtgtgtggaa cagacggctg taatgataga  72780
gctggagcgt ggaaattccc acgaagcctg ctttttcctg attttgctcg aggagagagg  72840
gtaatactgc ttcctggaaa acagtcgagc acacgtttta aagcacacgg ctcgcttttg  72900
tccttgttca cggataattt gtttttgtcc atttcattta cacttggagc agtattttgg  72960
aaatgtagta gttttaatgg agaaagcaaa tccctaggca cgtacttgat gttttcagac  73020
atttagacat ctgagtgtat gccctttaac tggcatagcc tttgaagaca atgagagcat  73080
tatggatgtt ggatgggga ggggagcgat aggcttgtct attttaagtg tccccagctt  73140
tgctggcttg tttgttttta acccctgtat ccagtcttca aaaccaagtc tctgtctaag  73200
ccatttcctg actatgctgc atccagatgt atcctggaat tctatatctg agagaaacat  73260
taaattcatt cactaattgc agaggaacaa aatggcattt ccaggcggag gcagcacaaa  73320
gttctcactt tatgtacacc atgcctagat attttttaa aaatgtattt tctttttcaa  73380
agccttttta gacataaact caaaatatat aacattttcc attataaagg caataaatgg  73440
aagatctatg ggagaaaaaa tgaaaggcct gtataccttg tctgaatatc tcatcccagt  73500
tacagactcg tcatggttag cattgggttt tacatgcttt cagatctttt ctctaaactt  73560
gttgacgtgc acacaaacat aattatttca gacaaatgga gccatacctt ctatacaact  73620
ctgaaacttt ggttttatcg ttctgtagtt gagacaaggt ctcagcagtc taggctggcc  73680
tataattcat ttgataacag cccaatctaa ctgaattcct gcaatcctcc tgcctcagct  73740
tctcaggtaa tgggatcaca gatagacaag aaccatgttc ccccctcccc ctttttttcat  73800
ttaacagtta tcttgcaggg attatcatat atattttcca tgtttttaaa atggtttgca  73860
tagtacacgt attgcataat ttaaccattt tcctgtcctt gaacgttagt ctaactcctg  73920
tcattaaaaa atccagtgtt caggttggag agcactgact gctcttccag aggtcctgag  73980
ttcaactccc agcaaccaca tggtggctta caaccatctg taatagtatc tgatgtcctc  74040
ttctggtgtg tctgaagaca gctacagtat actcatatac ataaaataaa taaannnnnn  74100
nnnnnnnnnn nnnnnnnnnn nnnnnnnnnn nnnnnnnnnn nnnnnnnnnn nnnnnnnnnn  74160
nnnnnnnnnn nnnnnnnnnn nnnnnnnnnn nnnnaaataa ataaataaat ctttaaaaaa  74220
aatccagtgt tcttagtcag acatggatac acattaatca tagcactcag aaggtagagg  74280
ctggcaggat tacacaaaga aacactcttg aaaaaacaaa taaacaaaca aagataattc  74340
agtgttctca ctagccttgg tggccaacac tgcagtccta tcacttggga ggcagatact  74400
attagaggct agcctgagct acatgaaact gcctcaaaag gctaacccaa acaacaaaca  74460
ccctatcatc tttatgacag tttacagact tctgagatga tatgtaaagt ttgcattgaa  74520
tccatcagag aactctcagt tcattgtttt tccctacaga atatcaggtg tgtagtacct  74580
tttagtagac ttcaaaacaa aacaagcctt cctgcactct gtcctcaaca ccttctcagg  74640
```

-continued

```
gtgcagacta atgagagatc tatcaccatt tgcatcttgt cccctgaaac ttggttaggc  74700
tctggcaacc agtgagggtc ccagagaatt ctccctagct tctgtaagca agtggagccg  74760
tggacaggtt ctggagttgc tgtctaccaa gacacaaacg agcaggaaac agcaagtgcc  74820
tttacaagga cgggacttgg gggcttgctt tattttgttt tgtttgttgt ttgtttgttt  74880
ttgagacagg gtttctctat gttcccttga ctgttctgga acttcctctg tagaccagac  74940
tcgtctccag ttcacagaga tccacctgtc tctgcccccc ccccccacca gggccgccac  75000
ctcagggctg agttgggggc ttaagtgaag gtcttgacct ggaatttgaa ggaagttgat  75060
cattggaaga ggaatgaagt gtgagagtgt ggaggggaat gctcagaaga caacctggtt  75120
tggaagatgc aaggtcatgt gccgtcctgg aactgacact tggactgcac taacttccta  75180
tctctgattt ctttcccaga gatcttctaa tcaagttcac tggctctctg tggtgatttt  75240
gatgggcaga aaacactaga ttgtctatat caaggctttc aagaccttag taatttgtta  75300
attgttgttg ctgattcaaa ataattggaa aggaaaggaa aggaaaggaa aggaaaggaa  75360
aggaaaggaa aggaaagggg aaaggaaaga ggaaaggaaa gaggaaagga aaggaaagaa  75420
aggcccctcg tgcttcgagt tggagaagca gttccgaggc gtttggaccc agtgcagagt  75480
ttggaggtca gctaccccac gtccaccgag cacagcacat gtatacagca tgatgcagtt  75540
gctgctctga aggaatcact tccctcctgt aaaacagaat cctctggtta tttgtaacca  75600
cagaaggctc ctagaacaag tgtatggcag agacagtggt tttctttaaa gctgaacata  75660
gcatcacttg gggtaattgg gcacgttcta taaacttgct aattgcatat agcaagtgat  75720
ggtgaggggc tagtccaggt gggaattctt atgacagggc tccatctgtc ctttgtgaca  75780
gtgtgttcca gactgctacc ctagtagctg agaagcctgt tttcagatct tgccaaagtg  75840
tgataggcct gccttgagct tagcatagcc taatttgctt aagtgtagat gtgcttatac  75900
ggaattcttt tcaactgaag ttcatagaca cctcccaagt gtgtagaggt tgaaagcaag  75960
ttagttgaaa atttatggag cgctatcttc tgacagttct tgagtaggcc aggcaggtta  76020
tgctcagacc agtgtccctg tgatgtgtag gtcatatgag gatgtccata ttgtcctaac  76080
ttcaatgggc atacctgctt cttcatcaat gggtgataca agctccctgg ggagcagggg  76140
gatgggagcg gaggaaaggt acagagacaa ggcttcccaa aacccccaag taatttggat  76200
taagagtacc aaacagcatg cgactgggaa ggacgtgagg atggagggtc ccaagctagc  76260
ttggggcaag ctagttaggg gatggttcag agaggaggac tgagctgagt tcggggtggc  76320
ttatgtgctc agaatagcat ctgttacagg gccaaaggcg gaaaagaaga cacaccgaag  76380
aggatggcaa acctttgagg agatacaggt tgggttatta tgaatttgag ctctctccca  76440
tgtagacagc agacagataa ccagtaagca gagggcaccg atatcagagg atggtacatc  76500
taaagattca ctaaagttgg tactacattg attattgggc ttgaaactcg agtcattgtt  76560
gtaagacatg atggccacac cgtaagttgt tatgtaattt tctcagctaa ccttatggat  76620
actgtttcat tatcatggaa gtctaatagt taaaatggtt tttcatgaga tttttattta  76680
aagttgattt gagcatttgc tttgaaggtt tcaagaaaac tcatctgctt tgactgttac  76740
tcaagcaaga ctgggaggca gtgtacagct gtctctgggg ctcccgagac agcagggtaa  76800
aaataggaca aactttaaga atcccagata ttctcagata acaaagactg gtttattggg  76860
gcctttttttg tgcttggaca aaacagagaa gcctttgtgc tgtgattagc aagggtgctg  76920
atgacagatc tcctgtcaag catcaggctt tattctatga ctaaatggtg ctttgtcccg  76980
ccatccagag aacctttgta tgtgccttgt taaagtgtga gtttatgtaa ttgcttttgt  77040
```

-continued

```
ttttcccgtt tcattggtgc cagattcaat gagagtgact cattttgtga ccgagacaaa  77100
cattcacatt tagaccatgt taaaaataaa caaacaagag gcaggtgctg cctgcctcgg  77160
ttctgcatct ccgggctgct gtttcctgtc tcaggagttc aggtctcagg tagtggctac  77220
tactcagctc ccgtggtcac tggtccactg tgccccaggg cagtttctaa aggccttttg  77280
gatgttggtg acaggaaggt ccaaattagg aaatctggtt agatgggaag tagaaagtga  77340
tgtgtacagt gtctcaaagg cacacaggaa gacgacagtc ccagtctctt ctggctctgt  77400
agttttccca ccacacagca gtggtttgga gcagttactt tacatgtgtt tttcacacat  77460
atgcctcatt caggggctct ttttctcaca gagaagacgt ttggaaagca ctgatcaaat  77520
tttaatgaga ccatggagtg catttaatag tccccaaact gtacaacttt atttcccttg  77580
ggaactctga aggtggccca ggaaggaaag gcctagaagg ttgggaaaga aaacaatggg  77640
tttttggaaa gagaacatac gaagagtttg gcctcccaag acagacgtga tagttgatga  77700
aaatgtaagg gaggacgggt agaaagttcg cttaaaggat tgtaggcaga gtgggagaga  77760
tgttcgcttg agaaagtact tagcagccaa gtgtcgggcc ttgagttaga ttccccagag  77820
cacatgcaaa agagctgggc atagaggggt gtgcttataa acccagtcct ggaaagaaag  77880
gttagcagag gtagatcatt ggggctcaca gaccagacag cctaccctcc ttagtaagcg  77940
ccaggccagt gagggaccaa actaaaaagc aaaacaagat caaggttgag catgtatgtg  78000
tgcatgggtg cgcacactct ctcacacaca cacacaccca cacacacaca cacacctata  78060
atggttaggt gaactgggca cacccagcag tgggctggtt cggtatgggg ctgatgaccc  78120
tacacagctc agcagccttg gtggccctcg atgacttgca gtctagagat tgacacctgc  78180
accactgacc cgagccactg gggaatggat gaattatgtt caatgaatta tgtagtaagg  78240
catttcagaa agatttcctt gcgaggcatt aaagttttag aaatcatttc tgtatttaaa  78300
gacagaacct cttcaatctg gggggtggag ggcactaacc agagaaaggc tcctctgcat  78360
aaataatact gttttctgac tttctgcttc tccgttgctg tatcaggctt aatacttatg  78420
gatgccttta taggtctcag ggcagagtct tatgtgtgct accacacctt gcaaaaggtg  78480
ataaattttc tacaatggct gttgttcatt tgagttagat gaatggactt ttgtcatgca  78540
gtatcatgtg tatctataat cttgtgactt cccagtacat ggaacatcca cagagctcca  78600
tgcctttctt cttggccacc ttcgttactt cctttgagca ggactaggac agaggttgct  78660
ggagcctccg ttgccacccc agaccctttg gcacatccct agcaccacca tccaaatcta  78720
cataaaaaat gcagttagtg tggaggctaa acccaaagta cgtgctagag aaatggcaag  78780
tctgtggtgc tcggcagctc tggggcactg ccatgttgcc tctgctggct ttaaacagta  78840
ggtgctttct gatgagcaca caactatcta tgggtgctga tgaagacaca ggaggtcttg  78900
agttagggtc ggctcaggct tgaagcacaa gcatgaagtt cactcttggt ctgatgagac  78960
catagaagac caaactccta ttggatgatg gacagactct gaaaacactg taaacccaag  79020
ctgactctat ccccactcgt tactgaggga caagcacttt gtataggtac agttttctaa  79080
accaaatcat tgatgcaatt tagtgtggcg ctaggtgaca tgaactgtgg ccatgaataa  79140
tgcccccgag agctacggaa actcgtatct ctgtcctccc agctcacagg gcgccttctt  79200
tgcatcacct catctctggt gttcattctg gagcgtcagt gtgtcttaga aggtgaccaa  79260
gacttactgc ctcttaatat ttagctgtct atgccagaaa aaatcactca aagagcagtg  79320
acgcttttgg gggatccagg gccatatttg gggtataaa aggtgactag actgtcagcc  79380
```

-continued

```
acctagacct gctttaccta atgaatatag ggtttaggaa aggtggctgt aagcaatgtt  79440
acagcctcct ctaaaacatt ctttttaggt ttaggtattt aagtttatgt gttacatgtt  79500
ttgccagcat gtatgtatgt atgtatgtgc atcatatata tacactggtg cccttggagg  79560
caacaagagc ggttggatca cctggaagtg gagttacggg tggttgtgag ctatcatgtg  79620
ggtgctggga actgaacctg ggtcctctgt aagagcagcc agtattgtta actactgagt  79680
tacctttagg ataactcagt cctcagccct ctttaggaat ggtattaaag atctagatga  79740
aggaactatt gagtatagat cccgattgca tgcatgcgtg tgtgtgtgtg tgtgtgtgtg  79800
tgtgtgtgtg tgtgtgtgtg tgtgtgcaca tgctaggaag agacgcatga caattcagga  79860
atacagatct ctgtgatttc acaacagcag actggccatt agagtgatag ctcattgcta  79920
gcatctcagg gaagcaacca ggaaaacatc caagcccgtc tctccctccc ccatcgtgtc  79980
actcctgaga aaacagaatt ctacgtttta atgtctgtca gtcttatgaa gaagcaccat  80040
aagtgtattc ttttgtacct aggggtgggg gacagtgtgt gcgtgtatgt gtgtgtgcgt  80100
gtgtgtgcac tcacacacgc tcatggaggc tcaaagagga catcaggtga cctgctctat  80160
cttatccctt taatacagag gactgaacac agagctacac tggtggccag aaagcctcag  80220
cagcccttct tgtctctgct ctgtgtggca ggagaaagag aagcacatat agccatgttc  80280
agctttttta tgtgggtgtt ggggaccgga tggagctcaa gtcctcgtgc tctcatggca  80340
gcctcttcct actgagccac ccctccagcc cttctttgac atgttaaact atggaaaacc  80400
attttttaaa gtgaaaaata acctgcagct taaaatttc cactaatttt cagtagccag  80460
ttaagtgctc atacattcac attgttatat actttgaccc cttctctaga actagtccac  80520
agtctgtctc tggatttagc tactgtaaac ggttcatata acaagacggc agtatctgcc  80580
ctttgtggat ggcttctttg tcttagcatg atatctgtcc ttgtcctttg gctgataccg  80640
tttccccaac gttactcatt aaaatgattt tatatttggt tccatttgct gtgtcataag  80700
agaactgaga caagatacta caactttttt tttcagacag tacattcata aagttagctt  80760
aacaattgtg ctccaccaca gaatgttttg acctgacagc cagtggctat ttcacttgtt  80820
tctaggcgtg gaagagaagg tggtttgtgt tgcgcagtgg ccgtttgact ggagacccgg  80880
atgtcctgga gtattacaaa aacgatcatg ccaagaagcc tattcggatt attgatttaa  80940
atttatgtca gcaagttgat gctgggttga cattcaacaa aaaggagttt gaaaacagct  81000
atatctttga tatcaacacc atcgaccgga ttttctactt ggtggcagat agtgaggaag  81060
acatgaacaa gtgggtccgt tgtatctgtg acatctgtgg attcaatccc acagaagaag  81120
gtacgtccaa ggttttgttt tgtttacatt tttaaaaatt tattatatgt gtgtgggtat  81180
tttgcctgtg tgtatgtcta tgcaccacaa gcattgcagt ggctgtgaag actagaggtg  81240
gccaatgaat cccctgggac tgaagttaca gatgttctga gtggtcatgt gggagctggg  81300
aattgaacca gggtcctaga ccttttcagc actaatccat ctctccagac ccagagttta  81360
aggttttgtt atccagttag tgcaatcatt tttctctttt tttgggggggg ggggcggggc  81420
gggaggttgt agttttagaa atggtacaaa attgttattt cagttatatg catcaatatt  81480
tttcttttac aatcggaatt tgacattttg agcaggcact gaatgcttca ggcagtttag  81540
agagaaatgc tacaggtttt gagagactta actgatatgg accagtctaa ataactgtct  81600
tcgtgaagaa tttggggagg ggagtggcgt gtgtgtgtca caatgtgagt gtgggggtct  81660
gtctgggtgg caggtgcttt acctgcagag caccttgtgc cataggctgt gacatacaca  81720
ggctgtgctc tcactgctcc ccacagccca cccctcccca gcttgaaagc agcaggaaca  81780
```

-continued

```
tttttaatag cagaactcca tagtccttaa aaatgggtga ccaatatatt tgggtacttt  81840
gtgttttcgt aatcaagtat gaagggtaga agacagtgag ctcatttata aaccattatt  81900
caaatatgga attgtggttt gtgagctgga caccagaaca ttgctaatca caaacccttt  81960
gtatttggtc cctaaacaac aaaatccctc gtaatttcaa tctccccata cttcctacag  82020
cttataaact atatcaaagt aactatatct aagaactata tgtaagtaat ggctttaaaa  82080
tcagccattc ctcatgcatt tgcagtacat accttcactg tatctcaaga cagatgtgga  82140
ctctaaacag cagagcagag ctttgtagca gtaatcccca ccattccatg tgctagagtg  82200
aaaaccggga tgtttgtgca ctatgtgggt gcagtgccag cagtggtcag aagagggcat  82260
cagatcccgt ggaactggtt tacagacagg atttttgttg gttttttaa tgtgtggggg  82320
tattttgcct gcatgtatta gtgtgtgtca catgtatgcc tggtgcccga ggaggccaga  82380
ataggatgct gggatcccta ggactagagt tacagacagt tgtgagctag gtcttctgga  82440
agaacaacca gttctcttga ccgctgggcc atctctccag cccctctatc agcaattttc  82500
tattctcttg tctccaacca tccctcataa ctactcccga aagagcaatg gcttccttgg  82560
cctttgttag gtctgtctct caggcatgtg ctctcccttt ccaagactga atatgcagtg  82620
ttcttgtttc aacagttggc tgataccttg tgacactttt tttactattt gaatttcaag  82680
ccagatgtgg gaagaaatag actctgcttg gacagcactg tctgagaaaa tcagtctccc  82740
gatccctctg agaataacta attttccctc aaaacaaaag gaaaggggaa aattctgacc  82800
tgtgttttga ttccaggaac ctctcaaaat atcattacca tgttatttcc gctgccccag  82860
gtgaccactg ctattattga atactcggaa cgctggcagg ccctcctgtt tttaaattct  82920
agctcactga actgtgtgcg gttcctgcta aggtttttct ttagtggatt tgggggtaga  82980
aactggggtt cttttgtttt tcttggaaat gtgcagattg actttttatt ttggttcggg  83040
ctcaccaagg tggaagctgt taaatttgct aaacaagcac taggaagccc agccagggct  83100
gcaggaagct cactgacatc tagcaaaacc tctgggctaa gtttagggta tgagcttaaa  83160
ttgcttttct cagagtgtcc agatcatggt agtttaaatt aaaagaaaat gcaattcccg  83220
atttgaggtt cttgccttta gtaagataaa ctgatactta aggaaaaaat atatagactg  83280
agaatatctc agcagtgtgt ttgtctagcg tgtacaaagc tctgcgtttg atcctcagaa  83340
cagcatagat gtgacataat ggtatatgcc tgtaaatgtc agcacctaag aggtggaggc  83400
aggaggatca gaagttcaag gtcttacaaa catagaagac cgtttctcag aggtggaaag  83460
aaagtgtagg gggttgggtg ggtacaagga tttcatcttt tctataacac agtagtcacc  83520
aagggcttct aaatttcctt tgactgagtc tggagagatg gctcagacat taagatcact  83580
ggctgctctt ccagaggacc ccgggttcca ttcccagcaa tcacgtaaca acttaaaact  83640
gtctgtaact ccagttctgg ggactcaata cctccttctg acttctgcag gcaccaggca  83700
ggtacacaga cacacataca aacaaggaaa aagacaaaac ggaaaccaaa taaacaagca  83760
gaaacccgcc cttcacataa actaataagt aaaatttact ttgagatttt tttttttact  83820
ttttttttt tttaatgaga caggattcaa acagaggttc tcttgcctct gcctcctggg  83880
tgctggaact taaactgtgc gtcgccacgc ccaactcttt ttacgttttt attaagacat  83940
ccactattac tattgtgtag gcatagatga ccagtgcatt gcttagaggt tttctatgtc  84000
tacatttgta catggatata cgtgagtgtg ctttaaaggc caagctcaga tcaagaattt  84060
caggattcac attccagcaa agaatccttt tcctagagaa atcctagaga aatttcctag  84120
```

-continued

```
agtagatttg ggataatttt gttttgtttc attttaagat gtatgtatgt atgtatatga  84180
gtacaccgtc tcgctctctt cttgcacacc agaagaaggt atcagatccc cttacagatg  84240
attgtgagcc accaggttgc tggaaattga actcaggagc agtcagtact cttaacatct  84300
gagccatctc tccagcggga tagttttaac ttctgtcccc agtcatgaat tttgcctgtt  84360
ttaaatcctc taaaaaaaaa aaaaaaaaaa aagaaccatg gagtctggct tacctcttcc  84420
ataaaagtca ccatgttgaa gtatgtggtg ggtttttttc cccatacagc actccctcac  84480
tcctattact ctcatacaat atgggtctat ttgaatatcg gtaaatggac atttcagttg  84540
ttctacaaag gtctgaccat tcttacgtgt ctttttacaa caaacaaaca aacaaacaaa  84600
caaacaaaaa gatccttttt tagtgtgtgt gtgtgtgtgt gtgtgtgtgt gtgtgtgtgt  84660
gtatacaaag gtgctaggga ggccttgaat ctaggattcc tactaggtag ttggaagctg  84720
cctagtgtgg atgtcaggaa ttgaactcag ctcctcccaa gagccgtctc tctagtctgt  84780
tttgtctttg gatagacatt agctcttagt tcttttggat acatgccaat gagtagaact  84840
gccacgtcat agcgtatatg cattttagca tttgtaaaac ataaatgtct tcaaagccat  84900
tgtaccagct gctgtcctaa cagtgtatgg caaatagagt tagcccatat tgttagtgac  84960
atttggcatt agtcagtggt tcatcttggc tttcccagta gctgtgtact ggcaagttca  85020
tgatttattt tgtgtgggtt tttttttttt tttttttttt tttgaaaagc agttcaacta  85080
gaaagattat ctcttctgtt tggctttctt gcaaagtttt agttgcgatt cagtgggacc  85140
cctgtggtgg ggtccaagct catagaaccc caggatttcc atgccataga gctctggata  85200
aaaacagtgc tgtttgtcag catccccgaa ggattagaaa ggtatttgaa atgtgtgagg  85260
gacaagaagc ttggaaaatt gagacgtttg tacttgaaac ccagtaaaca agttgggaag  85320
tgcaggcatt cagggtcttg cctggctgat taacagtgga ggcggcggca gggtgcctca  85380
ctgacagcag ctactactgc agtgtctatt tattatccat tcattagact gattgacctt  85440
ttaaatttca tatatgtatg gagagagaca gacagagaca gagagacaga gagagagaga  85500
gggagaaagg gagagagaga cagagaatgc gcgcgcaaga gagtgcccac ttgtgtgggg  85560
gtcccaggat accctgcaga agttatttct ctccttccac caggtagctc ctggggactg  85620
atctaagata gccaagctgg caacaaatat ctttacccgc tgagccatct cactggctca  85680
ttaaaggttt cttatcataa gttataggtt tgacatgacg tttccattca cgtacgtaat  85740
gtattttgaa cgtgttcacc accacacaag acacctctct tctcttgccc cctattcttg  85800
tggagccctt atacatacct ttgtatatca cacgaagcgt gacataccta agtaggagaa  85860
gccaatagta gggcgagggc tcctgtgagc cagttcactt gtggatgtgc tcatcacctc  85920
cccctgcact gaaggcttgc ctgctggaag gcctcgcatt agcttattag ctttctaagt  85980
aagtttcaat taggagtttg ctccagtggc ttattaggcc tttaatggat gctaattata  86040
ctctcggtgc attctgagtt aagaattggg aaatgatttt acatgtgtaa gcaaaccttg  86100
agccagtgtt tgtttcttag aagaaactta gagagagcag taagtcagaa atcaaaacag  86160
gactgagacc agaatgatct ataccactgg gcttgtcgcc cagaattggc tgaagtccca  86220
tgcctgtaag gccaagcagg agtctacttt gggccagtat tgactctcgc aggaatctta  86280
aatttgagat tatttagaca caattcaaca aatttttaaa tttacattat ccacgtgtgt  86340
gagcgtccgt gcttgtgttc atgtgtgcca cggggcatgt cagaacgata tatacttctc  86400
tccaccctgt ggttccaggg aatgaactca ggtcactggg gctgtggcat gtacccttac  86460
ctgcggagcc atctcactag ctctgcacca tccaattttt atatccacat actcagtacc  86520
```

-continued

```
aggtagatgg tcggctcaag acagaatgct gaagatggtg cattttccag gttaacacgc  86580
tagcatgatc tctgtactct taaagctact gcctgccact gtcacttggg tgtttggggg  86640
tacctaccgc ttatgtctcc acctttatga acttgcttgg ggttgtggtg gaattttaat  86700
ttcagctctt gcctcttgaa gacataggtg agtcctgaca tgctgttaag cacagcattt  86760
ttttttttt tttgaaacag gcccttctga gtcccaggcc tgttttcagg agattccact  86820
gtctttctca ctcctgggta ggaaatctga aaggtcagag gtgaagctgc tctatctgtg  86880
acagtagaac aagaccgggg agtgcgagtc tctgccagga caattttctt tttcccacga  86940
gagttcctca atttattatt ttatggctgt cagatgtaac aaaagaaaca aattaaaaaa  87000
aaaaaaaaaa acaaacccta caaaacaaaa cccgccactg aaggaaagtg tatctgtgca  87060
aaccgtcatc actaggcgag tcagaaggag gtcctgggtg ggctgcagtt cacggacctt  87120
cactgaggga actgtgcgtc tgcagcgttt ggttttcttt ccaactgagc gctgagcttg  87180
gttggtggta ccatgcatgt agctgaagag ctaacagaaa gcaggggcca cgcactgggg  87240
agagagcttg gagatgtggt agctgcttcc ccatttccct gctagtgctg gctggggctc  87300
ttgagctcat ctttgaatag taaatatttt ttcatggttc tcttaaggcc agaaggatat  87360
agtctgaatc attatttaat ctgcagcatt tgaaatcctc tgatgctaaa tccctgtatt  87420
agcaactgga tctcgagttg aacgcgttgt gggggcagct tacctcactt tataatcaac  87480
ctctcctaga cacagcaaca ggaacttaag aggacccact gaaattcgga caggatgtag  87540
taggagtggt cccaactgta ttttctgctt ctgtcttcct cctggcaaag ggtgttaaat  87600
catattagag aaatcgattt tttaatagcc atttcatgaa aattcataaa ttaaaagtta  87660
gaactcctct tggtctaaac caaggagatt cacagacctc attagcatag agcaggactc  87720
caagagatct caagcaacca gtccaaggct acacatgtag gcaaatgggc gtcgaggatt  87780
ttcaggtgcc tcctgctctt taaaaccctc ttccagtctg acaaagtgag cctggatgtg  87840
ctgcccagta gttgaaatgt ctccctgccc gtcccccaac ctcagctaca cgtaagagag  87900
acagttatga acacagcttc ctgatcatcc ctgaggcctg tgggcagcac gatactgttc  87960
tcctcagaca tcacaattaa gatgtgccct ggatactcct atctgagggg aagcattgta  88020
aagttggccg ttgtgaacat atgaatgagg taaacacaca aaaccatcaa aagtgtgcag  88080
attgctctag gaatccagag gagggtcagt tagaaggcca aatggctggt gttcagtcag  88140
agttgatgga ccatccaccc catcatacct tttagcatgt tttacgtatt ttattgttta  88200
aaatctgctg ttcaccagcc ttctctgttc actcttatga ccttatattt ctaaccagaa  88260
taacagatca tagtctatca gggccgttaa aattattctt tgtcatgtca gaaactacag  88320
agggacttta tttctagctg tacaacttat tttctagctg taagctgcac agtttatttg  88380
ttttccttca tctttggaac atgctcaagg gatttgtggg atttttggac aggtgtagtt  88440
acaagctcgg ggaagggtct gacgctacag atgagcaccg gattcccctt ggctcagagt  88500
tagagaggtt ttcccaataa cccggtaggc aaacctgaag agcagatcca ggcactctta  88560
gcagcattgt ggccatcaag tctgtcggtg taagtgtgtc tccttgctag gttggcgtaa  88620
cctagggaaa tgggggaggg gggaatccaa aacaacaaaa caactgtctc ttaggactgg  88680
agagatggca tagtggttca gagtactagc tgttcttgca gaagacccag gctccactcc  88740
cagcccctac ataataacgc atgaccatag taactccaat tccaggggac tctaatgccc  88800
ccttctggcc tccaagagca ccaagtacac atatagtgag cagacttatg tgcaggcgaa  88860
```

-continued

```
gtacctatgc acattaaatt acgttaacat taaaaatggt gcctactaag atcgtaggac  88920
agtcttattt taatttaagt agtttcaaaa ctcagtattt ttcagggttg cattagtgtg  88980
gcctcactgg gtgtagatct gggtctgggt gtttgcacat gagtgtgtat gcttgtggag  89040
gctggaggtt ggggtcaggt gtgattctct atctctgtcc atgtgagtca aagtcattgt  89100
atttggagct tgttaagagg gttagagtag gtggccagtg agctttcggg gtctgcttgg  89160
gtttcatgta agtttgggga tcttagctcg agtcttcctg cttatgtgac aggcgcttat  89220
ctcctcaggc cccatcttga tttctctcag gcctctggac taaaggaaag gctgaccttc  89280
ttcagatgtc tttggcaaga gttaattaac atataaccat tgcgatttag gtagtatttc  89340
tttcttagtt caaagctatc atctcgttct ttttgcccag attggccttg aactggtaag  89400
gcgagcattt cagtcttcag aatagctggc agagcaggtg aataccactg cccatggcct  89460
caggtagtgt ttgtttcagc taacactgcc atcattgatt ctggttatgt gcattaaaac  89520
aatctatctc cagactttca aagtagctta gtctaagaac aacagaatct tcaactgtga  89580
tagactaaaa cttaacttga ttacagatcc tgtgaagccg ctgactggct cctcacaagc  89640
acccgtcgat tcacctttcg ctataagtac agcaccagcc tccagtcaga tggaagcttc  89700
ttcagtcgcg ctacctcctc cttaccaggt catcagcctt ccgccacacc cagacaccct  89760
cggcctccag gacgatccac aagactacct cttgctgatc aactgtcaaa gcaagaagcc  89820
tgaacctaac aggtacatgg tacatgctag cgcatgtgcg cacactcaca cttgtgtgtg  89880
tgtgtgtgtg tgtgtgtgtg tgtgtgtgtg tgtgtgtgtg tgtttgtgtg tgtgtgtgtg  89940
agtgagtgtg tgtgtgtatg tatgtgtgtg tgtgtttgtg tatgtgtgtg tgtgtgagtg  90000
agtgtgtgtg tgtgtgtgtg tgtgattcag atttgtgttg caggtttata atcctctgtt  90060
aatgatttct gttatgtggg aggtattttg ttgttggcac tttctcccat catggctgat  90120
catagttgtg cctacagggc tgacttggaa agagtctcga agtctttgtt agggactcac  90180
agcgttactt gcttgacaga tgtcactgat ttgtaaatgg tgaccttgct ccatttctta  90240
tgtgattgta aagcagccaa gggtcatctt ttgtttctga agaaggagag gagtacctac  90300
tactagaaga ttttgaaagc aaagcgattc cattgcagtg agtgtgctgt agttgtggaa  90360
ctgtgtgaga aactaatcat acaggtaaaa tcccattatg gcaaatccta gaggctaggc  90420
agaccaggag gcaatgacat ttcatgaaat caaatagact gctacaagct gtgaaccttt  90480
caaaccttcc tccccagcca tggagcagtg ctgactccaa gctgtgactt acaactttta  90540
aaatagatat atgtggggtg tatgcctgac ccagagggtc caaagagcct tttccagatg  90600
cttggtagag ggtcatcacc acacacacac acattcctgt gctaagcttg aagctatttt  90660
aacttggcca tctttggcat ttgatagtga aaagtgaaaa ggcataagta agtggcagag  90720
gatattgaag gacagttact ttatcatttg aagaagcaac aggaaagtga agatcaatat  90780
acaagctagt gtctgctgct tacaactcgt gaccattggt gacagcacca acaactggaa  90840
tatttttcac tgtgcaaaaa tggcaatgac tcccaaggaa gatttataaa atatggtgtt  90900
aaggagttaa gctttatttt taataacaaa agtgtttctt ttctttggtt aaaaaatgat  90960
tattagttag aataagatta tagagtagtt gtttaaaaaa tgtatgtaga acttaaaact  91020
cccagaaatg gtttctatga ccccttccaa ggggcagtga gtgaaaggag agagacgaca  91080
ttccatggat ggttttgtct gtttgttata atggtatttt acctgtaaga gcaagaaaat  91140
tgtgtaagtc aacactagtt aatactatca aattctaact caactgtgcc tgtttgctgt  91200
gagcattgag gcagcacact tgtgggcttg cgccctgtgt gactaactga ttctttcctc  91260
```

-continued

```
tgtggaaact cactgttact tgctggtgtg gttgtttttg ttttgtttta ttttgtcttt  91320
tagaatccaa ctgatcagtg acaatgtttg gtgtattttc ttcttatgac agtgcctttc  91380
attgattttg ctggtacaac accattactg ccacaggaga aattgttctc caagttactg  91440
agtagatact ctgctgcagt gacagttaaa taacaaatat ttgtaaagtc cctaccacat  91500
gcccactagt atgttaggtg ctatgaagat acaaatggat tacagtcccc tgagattcag  91560
tcaccctggg agctctcaaa gtaaacctgc tcaagaagcc agataaacta accatttata  91620
tatgttatat ttatatatga gagcacaggg gacggttgct cacacatcct tctccaccat  91680
gactcagctc atatacatgc cccttcagga agcctgtcta caggcttaca ttgaaatgtc  91740
cctctgggtt gatgaggttt tgtttttgtt ttagtgtgtg tgtgtgtgtg tgtgtgtgtg  91800
tgtgtgtgcg cgcgcgaatg tgtgtgtctg tgtctctgtg tgtgtctgtg tgtgtctgtg  91860
tgtgtgtgtg tgtgtttcct tggaggaact cggcatgggc aaatacagga caggagttac  91920
tgagaacgct ctggcagttt ggtggtggta gttctgctgg tttataatta taaacagcta  91980
aagaacattt gtgctttttg aatcttaatg gaccacaaac aaacaatctt aacaaagcaa  92040
gttttgattg ctgagctgca gtgtatatgt tgccaaaact gactcgactg tggtttggtt  92100
tttgattttg gtttttgtc attcagaacc ctctttgact ctgccaagcc caccttttct  92160
gagacagact gcaatgacaa cgtcccttcc caccagactc ctgcttcctc ccagagcaaa  92220
cacggaatga atggcttttt ccagcaacaa atgatgtatg actgcccacc gtcccggctg  92280
acatctgtct cgggagagtc cagcctctat aacctgccca ggagctattc ccatgacgtg  92340
ttgccaaagg aatccccatc aagcacggag gccgacgggg agctgtacac ctttaacacc  92400
ccatctggga ctgcaggtgt agaaacgcag atgagacatg tatccatcag ttacgacatt  92460
ccgccaacac ctggcaacac ttaccagatc ccacggacat ttccagaaag cacactggga  92520
cagtcatcaa agctggacac cattcctgat atcccccac ctcggccacc aaagccacat  92580
ccaactcatg accggtctcc tgtggaaacg tgtggagtcc cacgcacggc ctcggacact  92640
gacagcagtt actgtatccc tcctccagca ggcatgacgc cctcccggag taataccatt  92700
tccaccgtgg atttgaacaa gttgcggaaa ggtaaagctc tggccggttc tgctctttag  92760
ggggtcagtg atagaaagtc tgtttccaca aggcttaatg agtaagagcc ttttctgccc  92820
aagtatagca cctacactta gatcctagca tcctctcagg tttctgatcc tagtgaaatg  92880
tatgggacgg agacaggggg gttattggta cttgtgtgcc agcctacctc tcggttcaga  92940
gaaagatcct gtctcaggag aataaggcaa agtgtgatat aggaggacac ccaatattct  93000
cccctggtgt ccactcactg tgaaggcaca caagcaagta aacccacata catcacgcac  93060
atacatacac atgcaagaaa agcaattttc tcagtaattg ctctcttcag catagaatgg  93120
tggtgaagtg tatttatcct ttcttcacct ctgcagcccc cacacgtgta gccatgatac  93180
cagaatcagt agatccctgt agggtgtgtg tgtgtgatca ggggggctgg tgggtgtctg  93240
tgtgtgtgtc tgtctctgtc catttgtctg tgtttctgtg tgtatgtctg tatatctgtc  93300
tatgtccatt tgtctgggtt tctatgtgta tgtctgtata tctgtctgta tctgtgtgtg  93360
tctttgtgtg ggagtctggg tctatgtgtc tgtgtctgtg tgtgtgtgtc tgcctgtgtc  93420
catgtccgtc tgtctgcctg cctgcctgtg agcatacacg tctgtgtgtc tgctctgtta  93480
gaagaaaaag ctggatcctc tcatgcctga aaacgtgtgg tcttacggct tcctacctcg  93540
gttctctccc atttcctaga cttctgtaga ggtgggctgt ctgaacactc ctagtgatgt  93600
```

-continued

```
ccttgcctgt gtctgtgtgc caccatgact atttctatgt catatctcca gggttttccc  93660
cttccttcct tgaccagcag cttttacatt tttgtcttca taggcagcga tgctgttcaa  93720
gtcgagccat tgtactttga ctttttcaat ttttagagca ctgcgtctct cctctctctc  93780
tcttcagctt agctgacagt gggtatgcct gtcttgtccc ataaagcctg caaacacacg  93840
ctaaagacct cgggagtgtg ggcttggtct agcttaatcc tcccaagatt ctggaatttt  93900
tgtgcagtat aaatactgtg tgttcagcat attgtcccat ctcctctgcc ttctgtttcc  93960
tccatgctcc ctgttcctct tagttccctt catctcctag agagttttgt gtctactttc  94020
atattaaata tgattttatg tatcaatata aaatctagtt accataaaat atctttgtct  94080
ctatgagatt agcttaatta tcttaattat ctcatgttct accttctagc aagtggtatg  94140
acttcattct tcgttttgtt ttgcttttca tctttattta ttagtttatt atgtgtagga  94200
ggtcagagga caacattcaa gagttgcttc tccccttcca ccatgtgggt cccagagaac  94260
aaagtcaggc catcagactt agcagcaact gcctttattt gctgagccat caggccagcc  94320
caaattcatt gttctttaag ggtgaaagaa tccactgcta taggtgggac cacactttcc  94380
ttaccctgtc ttctgctgct ggaccctctg ttggccgctg tctagtttag ctgttgtgag  94440
ttgtgctgaa gcaaagactg ctgggcacgt ctctgtgatc tgtcgctctc aagtactcag  94500
ggtggtagct gggttgtatg gtagatgtgg tttcacttat ttaattttta ggaaacttcc  94560
ataatgattt tcctaatagt ttgtctagtt tatgttccca cctgcgatgt ctgaaggtcc  94620
tcgttctctt ttatccttcg cccttgccag cacttgttag gtttttgctg ctgttttatg  94680
tgagcgaatg tttgtgaggg gcagatttgg tgtggttttg gttttctggt tttttgtttg  94740
tttgtttgtt tgtttgtttt gtttaatgac caacattatg actgggataa ggagaaatct  94800
cagtgtggtt ttggtttgca tttctctgac agctattgag gttattaaac tgtgtgtgtg  94860
tgtgtctgtg tgtgtgtgtg tctgtgtgtg tgtgtgtctg tgtgtgtgtg tgtctgtgtg  94920
ttaatggcca tttgtattcc tttctttggg tgctatatac tcctttagtt agcccattta  94980
ctggctaggt agttttctta tttagttttt aagttcattc ttgctatgag cgccatgttg  95040
ggtgtacagc tggcaaaggc tctctcccac tctgtaggct gcttttactt ggtcactgct  95100
ccctgcactg tcatttgtaa tttcatgagg tcttgtttgt cagctgttgg ttccatgtgc  95160
tggatggccg aggtcaactg agcgtgtgca ttgcctggcc tgtgcttctt tcttccccag  95220
ccacttctga gtttcaggtc acatccctct gtaaggtctt tgagccactg gagttggttt  95280
ttggaggatg aactgctggg atctagtatc attgttacac agatggctat ccagattctc  95340
actactacct gttggagnnn nnnnnnnnnn nnnnnnnnnn nnnnnnnnnn nnnnnnnnnn  95400
nnnnnnnnnn nnnnnnnnnn nnnnnnnnnn nnnnnnnnnn nnnnnnnnnn nnnnnnnttc  95460
cttccttctt tccttcctgt ctttcccctc cctccctgtc cttctcccct ccccactccc  95520
ttcctttcac cttgccacag gatctcatgt agccctgtct cactgtgtcc ctgagggtga  95580
ccttgaactt cacacacaca cacacacaca cacacacaca cactgctcgt tgctgcgatt  95640
tcaaagaggc taaataacct agttataagt tagtggctca aaatggatat catttctttt  95700
ttccatcttt agataatcct tttcctgcca ggcttggaca ttcggttgct gtcatagtca  95760
gatgatgaca ttggtaaaca cgtaggtgtg tgcttaacat gccagttaga gaccctgctt  95820
gatgagtgtg ctttcagtgt taacagatat gtgttcatgg acaagtgtga agagagagta  95880
ccttcgagct ggtaacacgg gaacaaaagc tgactttttt tttcttaatt ccagatgcta  95940
gttctcaaga ttgctatgat attccacgga cctttccgag cgatagatct agttccctgg  96000
```

-continued

```
aaggcttcca tagccagtat gtaagtacaa ctgaccactg gccctgccac gttctgactc  96060
tttagactta gtgccccgta ctctatatgc gaccatgaaa tgaaagtaac tacgggttct  96120
gtagatacag gcgtgatact tgtgtgtgac agtggctttg cttattaaga gaaatgtatg  96180
tgtgttttag aaaatcaaaa gcgtgttgac agcgggaggt gtctcgggtg aagagctgga  96240
tgagaactac gttcccatga accccaactc gccacctcga caacattccg gcagctttac  96300
cgagccaatc caggagccaa actatgtgcc aatgacccca gggacctttg acttttcttc  96360
ctttggaatg caagtccctc ctcctgctca tatgggcttc aggtccagcc caaagacccc  96420
tcccaggagg ccagttcctg ttgctgactg tgaaccaccc ccggtggata ggaacctcaa  96480
gccagacaga aaaggtaagg gggtgtggcc agtaaaggat aaggtgggga catgcagtta  96540
gggctctatt aaccatacca aaacatgaaa ctgtttaggc tggcatggga ctatgctgaa  96600
gcactttata tagcctgggt ccttaactta agttcagaag tcctactatt cgtaaatgaa  96660
tatgttgatg tccaggtggg atttccaggt ctcctcagac ctacagtaga gcttacagac  96720
taagaatgcc cagagcaatg gcagcagcag gcaagcacta ggagaatctg gaatgttctt  96780
cccagaggat ataggtagag ctcccgaccc ctgcctgact gtcccctccc ctgatgtatg  96840
acactcacac atgtcaagag agacctgaaa tctcaggttg tatgtgtgtc agtgtcttga  96900
ttgttttgtt gttgttaatt tctgccaact gttttgcttt tgtaaagcat agcaaaccaa  96960
gcttaacact agatatgacc ttgctttgct actttgtata ttatcaaatt agattccaga  97020
taataatgca cttgatgtgg ttatttaaga atagtgaaga tgtctattat agcctttctc  97080
tttccccaca tcatgacttt aaaaacacct gccttggctc caggctaagt ggaagcttct  97140
atggctctaa ttctggatga tgtaaggaaa gttgacttct gaagcagggg agctagtgag  97200
gcctggttct ctttgtcaaa ggaagccttc agccactttg ggtaatgtct cctcaagttt  97260
taaaaactta ggttcaagcc aggcatggtg gccttagctt ttcattctgg gatctgggat  97320
acagaggcag gtaaatttct gtggttcaag gccagcctgg tctacacagt tctgggtcag  97380
ccagagctgc acccatctcc aaaacaaaac aaatttaggc ttaagtcttt taaatgcaac  97440
acactgtgct cagcacacca ctagtgtgtg gcttagtctt gataaccaac taaagttaga  97500
gttgtatgat agaatgatgg atttctggct tcttgcagag aaattaaggt catttgaaaa  97560
gccacgtgtc atttatagct tttttcaggc catgtaatgc ttatgcaaac ttattaacct  97620
gggcttaagt cattaacact aattatgttg tagttgtggg agactcaggt ttggttttat  97680
tcttacgtaa gaaagggtgt atttctgctg tactcaatgg taatttgtgg tctttgccct  97740
gtgcacttgt cttgtgggac gtctctgcat cttctctgtc cgctcccttt cttttctcct  97800
tccctccctg agttctctcc cttgactggg ttctgccccc tttggcctgc agcacttctc  97860
tgtggcctca gtcctcccgc ctggatccct ccttggccct tgcccgtcaa catctgcctc  97920
taatgcctcc tccgtcattt tcaggcttca gattcttaga gatcacttga gtggtccagg  97980
ttatcccttc acacagatgc ctggctcctg ttgggacaga cgcccacctt tggtctcaca  98040
cagttgagaa tgaccccatg tggtagccgt agactcccag acacccatgc ttcatggcca  98100
ccatctggaa ttgtgttaga aagggtgtga gtgccacagg ctttttgtcc cttttgtttg  98160
tctttgtctc taactcaatt agaaatctca ctaattgttt tcttcttgac ataaaatgta  98220
agtgaacatg aagagatctg taattggtcc aagggtctct ggaagatcaa tacacatctt  98280
gtagacacaa agtattgaaa tctttttat tattttttt ttattttatt tgtttctctg  98340
```

-continued

```
tgtagctctg gctgacctgg aacttgtctg tcagaccagg ctggcctcca tctcagaaat  98400
ccacctgcct ctacctccca agtgctggtc ccactacctg gctttgagat ccccttttca  98460
aaagttaaag cggcatgtta tttccataga atagaacaaa gtaagcttgg atcgcgtttg  98520
gagacagtta ttcttccaag aactaggcaa acttgaaatg ggcaggacat ccatccccag  98580
caccacactg tgatttcatc ggccagacac tttatttggc ctatctgctt agatacatga  98640
tgaacggaca aagagcaccc aggggactac atccagggac agttttagcc aaaggttaaa  98700
gaggccattg agatttagcg ttagtaaagg ggttttactt ttctttcgta cctttaattt  98760
aaatcaatag gattcatggg aagaagcctg tgaaggtgtt tgctgcatcc agaatactgt  98820
gcctgggaaa gtataactgt taagaaaagc agtttagggc tggagagatg gctcagcggt  98880
taggagcact gactggtctt ctagaggtcc tgggttcaaa tcccagcaac cacatggtgg  98940
ctcacaacca tctgtaatgg gatctgatgc cttcttcnnn nnnnnnnnnn nnnnnnnnnn  99000
nnnnnnnnnn nnnnnnnnnn nnnnnnnnnn nnnnnnnnnn nnnnnnnnnn nnnnnnnnnn  99060
nnnnnnnnnn nnnnnnnagg gaagaaggga gggaggaggg aggggaggga gggagggagg  99120
aaggaaggaa ggaaggaagg aaaggaagga aagggaagga aggaaggaag gaaagcagtt  99180
taaaacccag attccagctg gacagggtta gcactccaga aggcagaggc agaggcaggc  99240
agatctctgt gagttctaag ccagctaggg ctatgcagtg agaccttgtc tcaaagcact  99300
aaaaagaaaa tctaaaagct gagattaaag tctcacaact aaacttatcc ttgagtctgt  99360
gtgagctggg agcatgtgtc ccattcgggc cacgagattg ttttccctcg gtgtggcaag  99420
agatgagagt tgtacctgca aattcagtga gtctgggtaa attacttgag ccgtcctttc  99480
agtgtcttat taactaattc ataaggaaat gcgattgtgc caggtgtgcc tggctcctct  99540
cagagcctca gccagctggg tgttggtttg tttgagctgc tctctttgag agagtccatg  99600
acaaatagtt ggcagcctcc tctcggttct cccgcagttt tatgtgccct gccacagtat  99660
acatgtggtg ctggccagtt ttcagacgct tcccacatac tgaggccaca gaagtacaga  99720
ggtgctgtgt gtgcagacgc ctggcgtgtc cctgctgtcg gctgtcacag cttgatcgct  99780
agctcagagt tcacgatgct aaccctgtag tgtttgtttc aaacaagatt atgtgtgcat  99840
ttaataagga gagctttaag cgtattgtaa gagataccag aagagtagag cagtcgctct  99900
ctagagccag agtggaacag tttgtagctg cttgtgtttc taatggaaaa ggaattttgg  99960
aagagttgga gatttttata aaatatctgt tgggtttcag taaaagtaag ccgtgacaca 100020
gagggccctg cttaaccact gggctcatct ggattctgct gcttccatct tccaggtcat 100080
gccagaggca gaagccacca acgatggtgt tgttttcctc tgtttgaaga gatattatca 100140
ttcttctttt aaagtttgtt tttgttttgt tttgtttttt gttttttttt tgagacaggg 100200
tttctctgta tagctctggc tgtcctggaa ctcattctgt agaccaggct ggccttgaac 100260
taagaaatcc acctgcctct gcctcgcaag tgctgggatt aaaggtgtgc tccaccactg 100320
cctggctcat tctaactttt taaaaatcga gaccttgaag tttttgaata tcattaaaaa 100380
tgaccgtgct ttctttaaaa ttatgcttat aagataataa atatgtaaag accagatgag 100440
tgatactagt accttaacta attttttaaa agttttttc taaattttta tattcaccaa 100500
gtagatgcct agcggctgag gaaacccaaa aagggtatca gatccagtgt gcaactggag 100560
ttacagacag ttgtgaacca ccatgtcggt gctgagactc accccaatcc tctacaagag 100620
cagcccgtgc actgacccac gtctctacct tccttcacta aatttccata aacaggagtt 100680
aatgtttaat tcctaaatca gactgtggat acacttgtta gagcttaaag gaaggaagta 100740
```

-continued tggaatgtgt tcctacagca tagccttacc agcctgagac agtttcccca tgtaatactt 100800
accattaggt actacagtgt gtattatatt cctcctctca tagttaaaac aaggacaaat 100860
ggtttttctt tcacaaccct gcctcaaatc acctgcttta cttttcttcc accttggttt 100920
tggggtgccc actggaaaaa gtcctgcaac tttagaagag tatgcctgca tgatttgaag 100980
ccaattcaga aagttctagt gtagcactga gtttatgtag gcattacatg acacgtagga 101040
gaccattcat atgcagcgct ttccaaaaag gcttgcccct gtgtatttga ggtgggactt 101100
tcatgtgatg attttgactg tactcaagct gaacacttct gaaaggactt cagtataaat 101160
gaggtttgct tatcagagag ctaagggctt accctcagta aatccccttt gctaggcatg 101220
gcgtctgtga acccaaggaa agatagagtc acttccctaa gacactcacc atctaggttt 101280
gacagaggag gtggacgggt gagcacacac acacactgtg tgtgtgtgtg tgtgtgtgtg 101340
tgtgtgtgtg tgtgtgaatg cccagggaca ttcacaatgc tggttagctt tgtcactcta 101400
agggcagctc ttctaacgca agcctgataa agggggaggg gcaatgaggg ctggagcaag 101460
ggagaggagg cagagctggg gagctgtgag tggcaggaag acctttccca acatgggagg 101520
ggattgctca gtcattgatg ggtgagcacc gccaagacag tagggagagc aagtagggag 101580
agcacgggaa agaaagaaga atctcacatc ccgaggagac accctcatcc aagctaacgt 101640
gctaatgagt gctttattct gagcactctg ggtgaagagc tttatgcaga cagtgacaat 101700
cacttggcac taaacgtttc attctgattt aaaataaaat aattatcctt tgctataaat 101760
gatacaaaaa tcacatttgt ttattatctc ccctagtgag aacttttccc agtttcccaa 101820
acccttcttg gtcgttggtt gggatgatgg agctatactg aggtcctttt tgcttggaga 101880
tcattgttga gaaggttgtt ttcttcatga cacatgagga ttggaataaa actaacaaga 101940
gttatcctaa ttgtgaaggc gatatctatg gaacacttta agtacacttg ggaagacttg 102000
ctatgcaaag catgaccttg atggggattc caggcaggag caaacacatg gagataagaa 102060
agtcacacct cctcctagac tcaaaggttc caattctatt agtaccttag tcattgccct 102120
tgggactctc tgcagcttca ctaatcagtg accacttgag tatttgttct ggtcatactt 102180
tcttccgaaa gcttggggag gagggttgga tgagttgaga caatacctgg ccatcagaag 102240
ttaagggcca cagtgtctat agagccagtc ttacaaaaca taacttagca agcttcgtgt 102300
agagaggatg gccctggatt caagaagcca tggtgggctg ataattctga gaaagagcag 102360
ggagcagtct ggccaatgca gagcgtgtat acttcctgat aagaatagaa ggagaaaggc 102420
cggtgttgtg aaaggcaaca ccgtccacac caccaaggtc tcccatattg tctgccaaaa 102480
ccaactcatg tttggagtaa ttcattgaaa gtgactggat gctctgttgt gctgtctttc 102540
ttatttattt atagatttat ttatttatgt atgtgagtgc actgtagctg tacagatggt 102600
tgtgagcctt tatatggttg ttgagaactg aatttttttt tagatctggt cgcctcccct 102660
ccttcagtcc tgctcgttct ggcccaaaga ttcatttatt attataaata agtacactgt 102720
aactgacttc agatgcacca gaagagggcg tcagatccta ttacaggtgg ttgtgagcca 102780
ccatgtggtt gctgggattt gaactcagga ctttctgaag agcagtcggt gctcttcccc 102840
gctgagccat ctcaccagcc cgagttgtgc tgtcttacac ggcaggcccc tgatgcctct 102900
tgggttcttc tgtctttcag tttgaagttt ctcctagtta gagaagacga aaacaacatt 102960
gaccttcgag gtcccaacag tccctgccaa gattacttcc tcaggcaagg actgacaccc 103020
aaaggatgtt gtctgaccgc cacacttaac acacacttac accttcacac aaacagacac 103080

-continued actcacatta cacactctct cgcgcgcgca cgcgcacaca cacacagagc ttcctccaca 103140
aatagtaaat ttgctcttac ttttcttcta agcatagata gattttgttt tgttttacta 103200
cattaagatt tagtaaaaga aacttaaaga aacatggata ggaactaatt tgaaacagtc 103260
ccaccgctga aaaaaaaaaa tacaacaaaa caaaatcatt tcctagatag ctaagcattt 103320
aacaagtcta gtacaatgag accccagaga gttaggactg tgaactctgt tatcagattc 103380
ttgatgatcc tgatttgtct gtggacactc cagccccttt aggttttaaa agagcttact 103440
ggttttaaga acctcactat tttttgtttg tttttctttg tttgtttttt gagacagggt 103500
tcctcgatgt agccctggct gtcctggaac tcgatctgta gagagtccgg cttcacactc 103560
agagatccac ctgcctctgc ctcccaagtg ctgagatcaa aagctgtgcc cctcctaccc 103620
agcaagcttc acggtttctc gtagatgagg tcattgtgca cgggagttgt cagggctgtg 103680
ctcaaaggct ctcgtctccc cagataacct gctccttcta ttttactctc agttaaaagt 103740
tctttcttca ttgacatgtt cagactagat gcaactgcgc agaggagccg ggctcttcct 103800
ataccaccct gaggattgaa cctcaggccc cctgggctga ccctgctagt agtgcagctg 103860
gtttggacat gtggttcatt aagcactgga cagcaattgc aggcaggaat atgaagctaa 103920
agaaatgtga gaaaccacac caagagagca gccattactt aacaccaaac ataaagataa 103980
aatttggtga ctacagcccg acatagtggc tcactgcttt aattaactct ggcactgagg 104040
aggcagaggc aggaagatct ttgagtctca ggccagccag gcctgtgtag ggagaccctg 104100
tctcaacaaa caaacaaaca aacaaacaaa agatttggag aatactaagg agaaaaaatc 104160
aggagggatg tgaagccatt gtgggccctt ctgaaaaagt ttgtgggaga ggcaatttgc 104220
aaactgataa ccccaggaac agtttgtgat ggttgtgtac tagacactcc atgtgccagt 104280
gctctgtggt gttcccacgg gtcacgtccc agccacagcc gtgtccacag agcagcagca 104340
gcagcagcag cagcagcttc acatctaaga acagacgcgc taagaagcct ctttctgctc 104400
gccctggttt gactgactca gtgtgtgacc actgaggtct aaggtcagag gctgacctgg 104460
agaactcgga actgagctcc ggaggacaag ccacctggct tccctgcagg accatgttag 104520
agccagggga cgcctcacct gcccctccca ttctgccttt cccattgtct tgttgtctga 104580
catgttagaa gacacactaa catggcccat gtgcttcctt cctttcctca aggaaggaaa 104640
agcaagcagc tgcttgtccc tttagccagc cctctctcgt cccctgtgcc tgtgacgctg 104700
tagcatgcca ttccctgcat tctggtgcac tgagcatgaa ttgtgtctag cgagactgga 104760
tgtctttcgc taacaagttt ttgtttatgc ttttaatatg tcacatttct gcacacgact 104820
ctgtttcttt tattgtttgt ttgtgtaaca gaatccattt tccaatttaa aaataacatt 104880
tttaataaga gagtcttctt tttaccaatt aggtcagagt cctaaaattt taagacccaa 104940
accccatggt ttagagcgaa ctgattcaca aaccataggt gactttgcta caagaagaaa 105000
gggtatgtac ctatgtgggg cactgggatt ttatttattt ttatggtttt ttttttttctt 105060 cagataaaaa gaaggagagc ttatgtaggg ctgctattgc cagccgtccc tgtgtgatag 105120
ttataagaga gcacatctgg agatggaggt gcgcagcagg cctgcgtcct cactgcacgg 105180
ggattatctg atagtgtgtg ccctcagtca ggcttggctc cctccctcca tcctccttac 105240
ctttccaggc agtaactcat tgtttccctt ctgcttctgg gctgctgtga gcccaggttg 105300
tctcctgtct ttgtatatgt atatgttgtt ttctgttgtg aaatagaata agaaataatt 105360
tcagtgtttt tactatggca tggcttagaa aatgacagct aaactcttat tcacctttttt 105420 aagtttttgt tttgtttgtt tgtttgtttg tttttaaaaa gggaacatga agaaaagtcc 105480

-continued cctttcttca gcccaggatg ctgtatgtgt ctgttttaag gatacagatg ggaaagctct 105540
taactcaaga tttctaactc tatctttact ctgcttgagc tgtgagccta tgtgatctgc 105600
agctttgaaa cgagaacttt gtgcccctgt gctgttgata agatagttga ttatgattac 105660
atatttttga acccaaagta agaaaaccta ggaggttttg ttttgttgtt ttttatgatt 105720
cttttggttt ggggtgtagc aacgatttta gtgctttcta cacatcattt tacatatgaa 105780
aaactatact gaggcttcaa tagtggggac catgtctgac acagatgaag atgagattca 105840
taaaacaatt cattaatgcg agcagtgccc agaggagctt taaaggggca tactttacgt 105900
tgtcgtttaa tttatattta caggtagagg ttagaccttg agctgagtca agcagtatcg 105960
ttgtgttgaa gccatatata gtaggagcag tagtagaggt tagacctttc gttgctgagc 106020
gttagactct gtgtaagacg atgtctgcct accaagtgtg aattgcagca ttgagggggc 106080
cttgtttatt ttgtgaagtt ctgtccactc acaccgtccc tccctttctt tgcagtcaag 106140
ccggcacctt tagacataaa acctctgtca gaatgggaag agctgcaagc cccagtcaga 106200
tctcccatca ccaggagctt cgctcgggag taagtgttct actgaaaacg cacagttgga 106260
gtggcaagac aatgaaaatt gtttatttca agagagatgg gttgaaaaag aatctagaga 106320
aagcccaaag tcaagagtat cttcatttgt cataataaaa atgcccgata tgtaactgta 106380
aactaatgac cattgcagaa agagcatgtt ggagattgct tttatatggg tgggtatgtg 106440
gggtgatttg acacctgttc cgttaggttc atgatgtcac tttctctagc tcctctaggt 106500
ttcccatgtc ccctcggcct gattctgtgc acagtacgac atcgagcagc gactctcatg 106560
acagtgaaga gaactatgtc cccatgaatc caaatctgtc tggcgaagac ccggtatgtg 106620
caggcctcgt gttcatttct ctacctgagc tgccctttga agcgagttca gcttaaagtg 106680
ttctatctgt acacatttac cctcccgtct ttcttcctat ccttgaaaaa acaatgaaat 106740
aatttttaag tgatgctttc ttacgtactg tcaaagtctc agaccagctg ggatcaaact 106800
gttctgtttg tacagttgga aatcagtgaa aacatgaagg ttttcattac agctttctgt 106860
agcttgtagc aagttcccga ggcaatcaac ttataaagac agagaaggtg tccgtgactt 106920
ggagtgttag gagtgtctgt gattgctcag tgttgtcact ttgggccagt ggtgacacat 106980
ggttgtggct agtggcacag caaagctatt ggccttatga cctatagtga agtgagacaa 107040
ggagcttgct tgatatgata tgttcaaaga aatatgaggt gataaatttt caaaattcca 107100
cataagcaaa ctggccgaca ctggggccag agagcacgtg ctgctcttac tggagttcag 107160
cttccagtac actgcagatg gttcactgca gcacctctac ccagggcatc gggtaacgtc 107220
tgctgtgtgc caggtacagc tgaaaagtca actgtcccct ctgcagcttc ccgtgccacc 107280
acgactctga ccctcccagc cctgcattag attgtcaagc aagcttcatc agagctcttc 107340
actcttggaa cacggtgtgt tgatggaatg ccatggaagt tcacagggct aacatgctct 107400
tggacttatt aaatcagtgt aaacaaaatt aatagtctta gaaaagctag gacagactca 107460
ttaccacatc tgatttgtgt gtaaaggtca agtcacacgt ccaccaagtg aactctaact 107520
agatggccta aattttagcc atggtccagc acttctgcca taactgtccc tagggaataa 107580
cagaagcatc actcagtttt ctatatgtaa gaattttaga aaacctagca ctattgtttg 107640 ttttttttcct tgatatacag aatatctaga acagtctctg aatcttaaaa gtttctctaa 107700
aaactgtgtg gaaaacactg ggtgacaggc tactgtagag tctaacagct gggtttcagc 107760
cctactttaa gatgaaaaag aagtccagtt ctgctgataa ttagacagag ttcagtgaga 107820

-continued aatgctgaca gattctcttg gggaacagct ggctgcagtt gactgtgcca ggtcctaggg 107880
atttatgcct tgcttttatg actttataat attgtaaaaa ttgtcccagc cagcgcaagg 107940
tagggcatgg gtgtgtttgc agttgtcacc tttagacaca aagtgttacc ctcaccccaa 108000
gctgagagtg aaagatggtg tccttcagag gacaaaaaga ttgttattgc acatttcagg 108060
gttcctttct cataacctag gaaaggggcg aggggtgcca gccattttaa ctgggcatcc 108120
agatgttcct gaattcttgt gagctgcgcc attggtctga aagttcttgc caaagtctgt 108180
ttctgtttct ctacatcaag cttgtttgtt cttacttgtt agtgctgccc tctatcttcc 108240
tggttgtgct acatgattct agagagtttt atcatatgct tcttagagga agaatggcat 108300
cagactaaga gaaaacagaa aagttactgg aaggaccgca gtcatgatcc acatccttta 108360
gttaatgtac tccaaattca ttcttctcta aatacctaaa agttaaatgt ggatctttaa 108420
ttctttatta attttttaa gatttattta ttattgtatg taagtacact gtagctggta 108480
tcagatttca ttatggatgg ttgtgagcca ccatgtggtt gctgggattt gaactcagga 108540
ccttcagaaa aacagtcagt gctcttaacc actgagccat ctctccagac cctttattaa 108600
atttttaatg caatatgttt tggccgggca gtggtggcac acatgtttga acccaaaact 108660
tgggaggcag aggcaggtgg atttctgagt tcgaggccag cctggtctac agagtgagtt 108720
ccaggacagc cagggctaca cagagaaacc ctgtctcgaa aaaaccaaag aaatacatac 108780
atacatatat atatatatat atatatatat atatatatat atatatatat atatatgtca 108840
tattctttcc cctcccctcc ctttgaaagc aagaaatatg aggatccttc actataataa 108900
tgtaactggg tacatacata tatggttttc ttttgttttg ctttgttttg agatatgaag 108960
ttgcagttgt taacctagga cagtcctttt tcactgttca aggtttattt ggtgttttca 109020
ttggcatgac atttaagtgg ttggttccat cacccatatg cagatcttac atttcacata 109080
atattgcagt gcacactaca gacacatata atacataaaa tatcctgtag aatatttatg 109140
caaagttata cataatggac gtacacactg gagccaggtt atgactaact gggaactcgt 109200
tggcctaggc atgcttggtg agggtgcaca gggcagcaat gcagaaggct cgcagggtaa 109260
tcaaagcctg cacagttggc agtgtgtctc ggagacagtg ggactgtcac actaaccagg 109320
ttaccactac acaagtacca cttggcagca gggcagagct gtgggaactg agatgtttcc 109380
ccacaccacc tcaacatcat tgtactaacc acagctcaga tgagaagggt gtggtctcca 109440
tagaatccct gctgcagcct ggacagtgaa gtgcgaggac actgggaaga ctttagaact 109500
gcagctcctt ctcgattccc cagagggtgt ctgcactctt cttcaggcgg gtctcttcct 109560
caggagtcaa tgtcaccttc acaacatctg agattccatt ttgtcccaag atacttggga 109620
cactgaggaa aacgtcatca ttgattccat agagaccttt aatcatggtg gaaatgggat 109680
gcacccgcct aaggttcttc gttatgctct tggccaagtc tgccacagag aggccaatgg 109740
tccaggatgt gtaacctctc agcttgatcg tcgtatatgc actgtccacc acctgctttt 109800
gagcctcctt ccactgctcc ttaaaacagt ctgtatcagt gcccagttct gggttcagag 109860
acttcaggga gacgccagca acgttcacac cactccacac agggacactg gagttgccat 109920
gttctcccag gacccagctg tgacagctca gagggtgaac cccccagcctt tctcccatca 109980
ggtaacggaa ccgaactgaa cccagatggc aaccacttcc aataactcga cttttgagac 110040
agccactgat tttccgagcc acttaggtca aaatatccaa aggatttgag acaatcagca 110100
gcgtgcagtg tggactgtac ttgacaatgt tgggaaggat gaacttgaag atgttcacgt 110160
ttcgctggac cagattaagt cagctctctc cttcttgctg acggcccctg ctgtgatgac 110220

-continued

```
cagcttggag tttgcagtca cacagttgtc tttgctggag accgtttttg gtgttttaag 110280
gaagaggttg ccacgctgga gatccatcat ctctcccttt agcttgtctt ccatgacatc 110340
cgccaagtcc ttcattaaga tacggatggc acaagccatg ccaacagcac caaccccaac 110400
aactctaatc ttgttctggg ggacctgttc ttccttaaga tccacagtca gctggtcttt 110460
gagggttgcc atcttggact ttgaatcttt tgagaccgct agagcacgat ggggggtgat 110520
gggcaagcag cagcgtggcc tgggctcagc gacagtggct ccagcaccag cctaggacag 110580
tcttgaactt gtaattctcc ttcatcatcg gcttccggat atcggaatta caagtgcgct 110640
ttcacaccca gacctgcatg gttttaagaa tgagagcttt tgcagctgtc tgtgacttga 110700
tgtctaagac ttttttttat tattactctt tacataattc tgagtgtgtg tgtgtgtgtg 110760
tgtgtgtgtg tgtgtgtgtg tgtgtgtgca tcttggttag ggtttctatt gctctgaaga 110820
gacaccatga ccacggcaac tcatataaag gaaaacattc cattggggct ggtttatagt 110880
tcagaggttc aatccattat caccttggtg ggaagcatgg cagcatccag gaaggcctgg 110940
tgcctgagaa ggagctgagc attctgcttc tgagagggca ggcaacagaa gtgaatgtct 111000
gagccggagg cagacttgag cttctgagac ctgaaagaga cctcaagtga cacacccatt 111060
ccaacaaggc ctcacctcct aatggcgcca ctctcaatgt gccaatgggg ggaccatttt 111120
ctttcagagc ctcgcagttt gtttctgcga agggttactt acctgtgcaa acatgagtaa 111180
agttatttac ttgagtaagg gacagttacc agtggctaca gcactcaggc tgagtattag 111240
tttaactaaa tttaacttca gagcccagga gttcaagacc atttttgaac aaggtagtga 111300
ccctccccat cccccagggg gaacaagaga gggtgggaga agagggcatc tcctgagtgt 111360
ctgcccactg ttcgctgttc tgttttcaga atctctttgc cagcaacagc cttgatgggg 111420
gaagcagccc gatgaataaa cccaaaggag acaaacaagt cgaatacctg gatttagacc 111480
tagattctgg gaagtccacg ccaccacgga aggtaagtga gcccgtgttc tctagatagg 111540
tcaagcacac tttgagggac catgttcttt ggggaaagtt gggggcctga ttatttaaat 111600
ttagtgactg ttgtttccta agtcacaagc aacagaatca tgaagtctga tagatttgtt 111660
tctccctttg tagaggtcgg tcagttgtgc agtttctact cgtcatggtc agtgcttttg 111720
ctgtctttag aatgaagaaa atgtggcttg gatgagtggg gtagccacat ctttaatccc 111780
agcacaggga agacagaatt tatctgtaaa aaggaagaaa aggagaacat ggctcatggc 111840
tcaagtcata tgctgttttg tcttaaattt taatttctat taaacctacc aattacacag 111900
tttctttata attctttggt tttggtgggt tttttaaata tttaacatat atgtgggtat 111960
atgcacatgg gtgcagtgtc cctcagagac tggaagaggg cattagctcc caggagctag 112020
agtgacaacg ggttcagttc ctccgaaaga gcagtgtaca gcctccccca cccccagccc 112080
tccttccagc ccgtgcatca ctggacttac tttgttattt aagtcctatt ttcttacatt 112140
gtttttggct tatcattctc tcttagactc agattttcaa cagtgtcctg ttgaagtccc 112200
tgtaatctga aggtcttttg gtagtgaatt cttctcaggt tgtgtataac tgaagtctct 112260
ttattttaga aacaagtttt gttgagatca cagttcttgt ttttttccct gtgacataat 112320
tacataattt tcaataattt gaattctgaa aataaggttg aaaaaaattg aaagatttgc 112380
ttacagaaga tgccattatt tgcacagaga aaagctcacg gcagtcatgt taatgtgtgt 112440
tggaaaaggc cgctgtcata ctgtcagggt aactgagcta ctgagtcagt tcttaactga 112500
gcctctttac tgcatggggg ccctctgttg ctgtccagtc tcttgttctg tcaaatgtgc 112560
```

-continued

```
cctttggaca cttcctatct gtttttctgg ctgcttttca gatgtttcct gctgaattta 112620
cagttttatg acgtagatgt cttttcacta atctgcttgg aagttgtgct attcacacac 112680
gtgtacgcat atacacatac tcatacgcac caacacatac acatacttac acatataaac 112740
atatatacac acatacacac agacacacca cacagataca tacacacaca tacacacata 112800
cttatacaca catgcacaca tatgcacaca tatgcataca catgtacgtg tacacgccaa 112860
cacacatgcc atggctgtac acatgacttt tctgcttctt ttgattacct ttttgtcacc 112920
tgccaggaac acatacagta tacctactat ttctatatct ttgtagtttt ctgttctatg 112980
atctatgtat ctctgttcta tgtatctgtt taattttgga tagtttttag ctctatcacc 113040
agatttccta attctccttt ctttttgttg aggtgttttg gtttggttgt tttgttttgt 113100
cttttgttgt tgttgttatt ttgtatttat ctctggggtg aaatgctgtt tgatttactt 113160
taactgacat taatctcttt gtgttacttg tatgtttaag gccttttctg gcttatcttt 113220
taacactgtt cacacacttc ataagtcctt ggaggccgga atttgcatgt actgtttctg 113280
ttagcccaca ctctttatgg ctgtctcctt gtgtgtttat acatttttat tacaaattca 113340
tggttgaact tggaggacct gaacttcctc cacagagcat ctctaattcc ccctggaggc 113400
ccactgagat tcctgctctg ggctcacgtc agcttccttc aagcttgtca ggagccttgt 113460
tatcagcatc ccaccttccc tgcctccttc cccacccacc gagctgagtc cctccccatc 113520
ctccctgaag atcttagaat gtccttgcta tctaggagcc ctacagagca ttgcccaccc 113580
agctggctca gctactgcat atctagctgc accttaagaa aagagggcct ggttgtggtg 113640
gcacaggcca gtacaatttg ctgaaggagg cagaggcagg aggatcacaa gttcaaggcc 113700
agtctgggct acacattttg ggctagaaag atggctcagt gtttaagagc acagactgct 113760
cttccagaga tccagagttc aattcccaga aaccacatgg tggctcacaa ccatctttaa 113820
tgggatccaa tgccctcttc tggtgtgtat gaagatgagc tacagtgtat taatatacat 113880
aaaataaata aatcttaaaa aaatagagaa gaggaggcag ctttcagtta ctgtgtatct 113940
agttgcacgt taagacaaga ggggacatct ttgtagttta ctttcctgca aatataactt 114000
tgccttcaga cacaccagaa aaggacatca tatcccatta tagatggttg tgagccagta 114060
tggttgctgg gaattgaact taggacatca ggaagagtaa ccagtgctct taaactctga 114120
gctatctctc cagcccccaa aagtactttt cttgcacaaa gagtaaagag ctgtttggtg 114180
ctgatccggg cgagaggaaa aaacactcaa acataagcta aagagagtct agttctgtgt 114240
gttagatgag ctagattttc tatgaatgcc atctgtgata gcagtattat tagtttgaat 114300
agttctatat aattttaaaa ttaagagaaa tcggtgtcaa gttagagagt ggacagacaa 114360
taccattaat ctgaggaaat gccagtttgt gtgtgtaatt ccaagattac atatgtctat 114420
ctatctacgt ttgtttgttt gtttgtttgt ttgctttgag acaagatttc attatgcaac 114480
ccttgctgat tcggaactct ccatagagca ggctggcctt gaactctaat atagagatcc 114540
accagcctac ctatgcctcc caagtgctgg catgatacca ccataccctg catatgtatc 114600
aatatcaaat cttgggtttc actcagaacc accctcacaa atggcccctt gggggtattt 114660
ccttgtgttt tttagcaaaa gagcagtggt tctggcagca gcatggcaga cgagagggtg 114720
gattacgttg tggtggacca acagaagact ctggccctga agagtaccag agaagcttgg 114780
acggatggga ggcagtccac agagtccgag acacccacca agaatgtgaa gtgaagacat 114840
gccgtcgcct ctgccggcag acgagatctg agtggaaaga gagatgccaa gtgaagatgt 114900
tcccactctc agtggagcct cgagccagca ggggcagaga gaaggatctc tcacacatgt 114960
```

-continued

```
tcaagcaaat taggttgtga atggtgctgt gtggtattgg atttataacg tgtaaataac 115020
ccggggaaat agtgttttta gttcacagag aagcttctgt ccctaattaa cacacctgta 115080
gtattactat actgatgcac ttttcattta aaaccttggt ttgggtcttc ccgatctacc 115140
ttaacagact ttccttggga ggtcttttgg cctcctcaca ctactctata taacaatact 115200
aagtgaactg agctacttgt aattctggaa attccagttg aagctacagg gctaacacca 115260
ttaaaacaag aagtaagttg acacattcgc ttttctcttg aaggtggtag ccattagctt 115320
aagctgtaga acatagttgg acttgtcctt cgttgttttc caaaaattcc ggggatattg 115380
tatatagcag gtcaagacct agctctctga ctcatgtaca cttaggtttt aactgtagga 115440
ctttgttatt attatttttt ttgttaatga cagtgttggg ttcatcgtgt gaaggttctg 115500
ctgggtagga tcttgcacct ttcaaagact gcctcttagt tacactagta agcccccaaa 115560
tcatccacag catggactgc tggcctgctc ttactcctgt ttatgtgtta aacattatct 115620
gcaaaaggca gattatacga ctgaccaatc aggtacgtac aaggcactga tgtgctaata 115680
cagtgattgg gtcagacaaa gtgcttcagt tagtgtgcgt tcgtcctaat cttggtttag 115740
aattaatgaa acagttggcg ttcactgtca gcagcatagt gtgattttga atgaattagg 115800
caggaattca agattactac tcttagctcg ctcgctctct ctctctctcc accgtagtgc 115860
tcttcctagg gttttctttc ttctacttaa tatcttcttg gccttatatt taaatcccta 115920
tgcaattaat gttttatatc tgcgttttta aaaaagaaat gtcattttaa gtgattcttg 115980
tatgtagcaa gcacctattg cttttgtgag taaatgaatt aagactttttg tactgtgatt 116040
tgtactcact gccccagttc cccaactgtt ggagccttgc tgctgtgaaa cgctgtagtc 116100
accatagttg tgtccaccac ccagccgggt ctgtgagtct cacctgtcac gtgacatcgt 116160
ctggtgtgga tgttggctct gaattagtgt cactgcagtt acacgtgtct gtctaggctt 116220
tgcaagatgc tgtagtcacc atagtcgtga ccaccaccta gccaggtctg tgagtctcac 116280
ctgtcacgtg ccatcatctg gtgtcactgc agttacacgt gtctgtctag gctttgccgc 116340
aaccttgaga agcagctagc attttccgtt gttcacacag taaggacaat gtctctgcat 116400
tgatctgagg ctcactggtg gcctggggaa gggacacaga gaacagaatg tctgcagctg 116460
aggcttgtct ctcttcgttc agacctctta cctgttgcct gagtacacaa tgcaccccgc 116520
tttctggccc actggccacg gtgctgtgcc taatctgagt tctcccctgg cttttccagt 116580
cagtttgaaa gctgtgttca taactagatg aagtgtagaa tagtaatatt agatgctttt 116640
aaatgttcgc ttctttttaa acaaaaacta aaacccagaa ctgaattttg aggtggattt 116700
ttaaataaaa aaagattgag tttgctgtgt gagctgtgtt acttttttct tacttttaat 116760
atactttcta tttttttgag caagcaacaa gtgtcaagaa aacacatact ggggttggag 116820
agatgattca gtgattaaaa gcactggctg ctcgtaagaa aagactggat ttcagttcga 116880
gcttgacata gcctctcaca ggcaatcata attctggttc cgggagtctg gctcctctcc 116940
tggcctctgg acactcactg cagacgcgtg cacagacatg catgcaggtg aaacacccac 117000
acacatacta aaaatgttgt tatgtatgta ttctcttggg aacatgacac gtagagagcc 117060
agagagaggg cccagtgctt acagcacgtg ttgcttctgc tgagaccagg gattcatggt 117120
agatctcagc catccatttc tccaggtcta gggacccaga tgccttcttc tgacttcctt 117180
tggcactagg catgcatggt gatgcaaaag aagttaggag acacagggcc catcctattt 117240
ctgggtatct gaatataatt atacatatta ctggtagccc agagacaatc acagccttga 117300
```

-continued atgttctgta ataaaactac caaagaaag 117329

<210> SEQ ID NO 2
<211> LENGTH: 4859
<212> TYPE: DNA
<213> ORGANISM: Mouse

<400> SEQUENCE: 2
ctgggctgaa gctagaggcg accgatcgtg ggaaggggag gcagaaaggc taggaggagg 60
agggccgggg cccaggccgc gcctccccga acccgccgcg cgcccccggg gtgggggagg 120
agcgcagggg acaggacaga ggggtccctc cccgaagcag agccgccctg cgcctcgtcc 180
ctgtgctgat ccccgccctc atccgaggct ggagcgcaga cccaccctcc caccgcggac 240
ccgcgacctc cccgacgccc ggcgacgccc tgaccctcgc tgctggtccg cgaactccct 300
aggctgatca ggacctgccc ctgtgccggc tgccacccgg acgccgcacg ccttcccagg 360 cgccctttc cgagcagagg gaaagagaag atcgagcccc tctcagtgtg aatgcgccaa 420
cgggcggagc ggagcggagc ggacaccgcg cgcgggcatt gtgtgtgcgc gtgcagcgtg 480
gggtccgcag cggggagcac ccgcgggagg tcccgtttcc aaggggcgga gcgcagggct 540
tccagttctg ggctccctgt ccggacagag tcccagcgga gcccgaccgc tgcctaggcg 600
gcgggacggc gcgcctggcg gccaggaggg cgcactgaaa gaaggtcggc gagccctggt 660
ccccgcggtt cccgatcgag ttcctcttca gtccgcgaat ctgcgggaga ggttcgatcg 720
ccgacacagg gcgcggggag ccgggccgcc ccgtcggggg aatctgagac gtcctctggg 780
ctgcgtttga ctgccgtgcc cgccgtgcac ggagcgcgtc cactgtgtcc accgacccct 840
ttggtgtctg gtcctcgagt cctcacggcg tgcaccatga gcggcggcga agtggtttgc 900
tcgggatggc tccgcaagtc gcccccggag aagaagttga agcgttatgc gtggaagaga 960
aggtggtttg tgttgcgcag tggccgtttg actggagacc cggatgtcct ggagtattac 1020
aaaaacgatc atgccaagaa gcctattcgg attattgatt taaatttatg tcagcaagtt 1080
gatgctgggt tgacattcaa caaaaaggag tttgaaaaca gctatatctt tgatatcaac 1140
accatcgacc ggattttcta cttggtggca gatagtgagg aagacatgaa caagtgggtc 1200
cgttgtatct gtgacatctg tggattcaat cccacagaag aagatcctgt gaagccgctg 1260
actggctcct cacaagcacc cgtcgattca cctttcgcta taagtacagc accagcctcc 1320
agtcagatgg aagcttcttc agtcgcgcta cctcctcctt accaggtcat cagccttccg 1380
ccacacccag acaccctcgg cctccaggac gatccacaag actacctctt gctgatcaac 1440
tgtcaaagca agaagcctga acctaacaga accctctttg actctgccaa gcccaccttt 1500
tctgagacag actgcaatga caacgtccct tcccaccaga ctcctgcttc ctcccagagc 1560
aaacacggaa tgaatggctt tttccagcaa caaatgatgt atgactgccc accgtcccgg 1620
ctgacatctg tctcgggaga gtccagcctc tataacctgc ccaggagcta ttcccatgac 1680
gtgttgccaa aggaatcccc atcaagcacg gaggccgacg gggagctgta cacctttaac 1740
accccatctg ggactgcagg tgtagaaacg cagatgagac atgtatccat cagttacgac 1800
attccgccaa cacctggcaa cacttaccag atcccacgga catttccaga aagcacactg 1860
ggacagtcat caaagctgga caccattcct gatatccccc cacctcggcc accaaagcca 1920
catccaactc atgaccggtc tcctgtggaa acgtgtggag tcccacgcac ggcctcggac 1980
actgacagca gttactgtat ccctcctcca gcaggcatga cgccctcccg gagtaatacc 2040
atttccaccg tggatttgaa caagttgcgg aaaagatgcta gttctcaaga ttgctatgat 2100

-continued

```
attccacgga cctttccgag cgatagatct agttccctgg aaggcttcca tagccagtat   2160
aaaatcaaaa gcgtgttgac agcgggaggt gtctcgggtg aagagctgga tgagaactac   2220
gttcccatga accccaactc gccacctcga caacattccg gcagctttac cgagccaatc   2280
caggagccaa actatgtgcc aatgacccca gggacctttg acttttcttc ctttggaatg   2340
caagtccctc ctcctgctca tatgggcttc aggtccagcc caaagacccc tcccaggagg   2400
ccagttcctg ttgctgactg tgaaccaccc ccggtggata ggaacctcaa gccagacaga   2460
aaagtcaagc cggcaccttt agacataaaa cctctgtcag aatgggaaga gctgcaagcc   2520
ccagtcagat ctcccatcac caggagcttc gctcgggact cctctaggtt tcccatgtcc   2580
cctcggcctg attctgtgca cagtacgaca tcgagcagcg actctcatga cagtgaagag   2640
aactatgtcc ccatgaatcc aaatctgtct ggcgaagacc cgaatctctt tgccagcaac   2700
agccttgatg gggaagcag cccgatgaat aaacccaaag gagacaaaca agtcgaatac   2760
ctggatttag acctagattc tgggaagtcc acgccaccac ggaagcaaaa gagcagtggt   2820
tctggcagca gcatggcaga cgagagggtg gattacgttg tggtggacca acagaagact   2880
ctggccctga agagtaccag agaagcttgg acggatggga ggcagtccac agagtccgag   2940
acacccacca agaatgtgaa gtgaagacat gccgtcgcct ctgccggcag acgagatctg   3000
agtggaaaga gagatgccaa gtgaagatgt tcccactctc agtggagcct cgagccagca   3060
ggggcagaga gaaggatctc tcacacatgt tcaagcaaat taggttgtga atggtgctgt   3120
gtggtattgg atttataacg tgtaaataac ccggggaaat agtgttttta gttcacagag   3180
aagcttctgt ccctaattaa cacacctgta gtattactat actgatgcac ttttcattta   3240
aaaccttggt ttgggtcttc ccgatctacc ttaacagact ttccttggga ggtcttttgg   3300
cctcctcaca ctactctata taacaatact aagtgaactg agctacttgt aattctggaa   3360
attccagttg aagctacagg gctaacacca ttaaaacaag aagtaagttg acacattcgc   3420
ttttctcttg aaggtggtag ccattagctt aagctgtaga acatagttgg acttgtcctt   3480
cgttgttttc caaaaattcc ggggatattg tatatagcag gtcaagacct agctctctga   3540
ctcatgtaca cttaggtttt aactgtagga ctttgttatt attatttttt ttgttaatga   3600
cagtgttggg ttcatcgtgt gaaggttctg ctgggtagga tcttgcacct ttcaaagact   3660
gcctcttagt tacactagta agcccccaaa tcatccacag catggactgc tggcctgctc   3720
ttactcctgt ttatgtgtta aacattatct gcaaaaggca gattatacga ctgaccaatc   3780
aggtacgtac aaggcactga tgtgctaata cagtgattgg gtcagacaaa gtgcttcagt   3840
tagtgtgcgt tcgtcctaat cttggtttag aattaatgaa acagttggcg ttcactgtca   3900
gcagcatagt gtgattttga atgaattagg caggaattca agattactac tcttagctcg   3960
ctcgctctct ctctctctcc accgtagtgc tcttcctagg gttttctttc ttctacttaa   4020
tatcttcttg gccttatatt taaatcccta tgcaattaat gttttatatc tgcgttttta   4080
aaaaagaaat gtcattttaa gtgattcttg tatgtagcaa gcacctattg cttttgtgag   4140
taaatgaatt aagactttg tactgtgatt tgtactcact gccccagttc cccaactgtt   4200
ggagccttgc tgctgtgaaa cgctgtagtc accatagttg tgtccaccac ccagccgggt   4260
ctgtgagtct cacctgtcac gtgacatcgt ctggtgtgga tgttggctct gaattagtgt   4320
cactgcagtt acacgtgtct gtctaggctt tgcaagatgc tgtagtcacc atagtcgtga   4380
ccaccaccta gccaggtctg tgagtctcac ctgtcacgtg ccatcatctg gtgtcactgc   4440
```

-continued

```
agttacacgt gtctgtctag gctttgccgc aaccttgaga agcagctagc attttccgtt   4500

gttcacacag taaggacaat gtctctgcat tgatctgagg ctcactggtg gcctggggaa   4560

gggacacaga gaacagaatg tctgcagctg aggcttgtct ctcttcgttc agacctctta   4620

cctgttgcct gagtacacaa tgcaccccgc tttctggccc actggccacg gtgctgtgcc   4680

taatctgagt tctcccctgg cttttccagt cagtttgaaa gctgtgttca taactagatg   4740

aagtgtagaa tagtaatatt agatgctttt aaatgttcgc ttctttttaa acaaaaacta   4800

aaacccagaa ctgaattttg aggtggattt ttaaataaaa aaagattgag tttgctgtg    4859
```

<210> SEQ ID NO 3
<211> LENGTH: 226
<212> TYPE: DNA
<213> ORGANISM: Mouse

<400> SEQUENCE: 3

```
atcctgtgaa gccgctgact ggctcctcac aagcacccgt cgattcacct ttcgctataa     60

gtacagcacc agcctccagt cagatggaag cttcttcagt cgcgctacct cctccttacc    120

aggtcatcag ccttccgcca cacccagaca ccctcggcct ccaggacgat ccacaagact    180

acctcttgct gatcaactgt caaagcaaga agcctgaacc taacag                   226
```

<210> SEQ ID NO 4
<211> LENGTH: 23
<212> TYPE: DNA
<213> ORGANISM: Mouse

<400> SEQUENCE: 4

```
acaagtgtga gtgtgcgcac atg                                              23
```

<210> SEQ ID NO 5
<211> LENGTH: 23
<212> TYPE: DNA
<213> ORGANISM: Mouse

<400> SEQUENCE: 5

```
cagattggcc ttgaactggt aag                                              23
```

<210> SEQ ID NO 6
<211> LENGTH: 26
<212> TYPE: DNA
<213> ORGANISM: Mouse

<400> SEQUENCE: 6

```
gcctgcatta ccggtcgatg caacga                                           26
```

<210> SEQ ID NO 7
<211> LENGTH: 26
<212> TYPE: DNA
<213> ORGANISM: Mouse

<400> SEQUENCE: 7

```
gtggcagatg gcgcggcaac accatt                                           26
```

<210> SEQ ID NO 8
<211> LENGTH: 23
<212> TYPE: DNA
<213> ORGANISM: Mouse

<400> SEQUENCE: 8

```
ggtgaatcga cgggtgcttg tga                                              23
```

-continued

```
<210> SEQ ID NO 9
<211> LENGTH: 23
<212> TYPE: DNA
<213> ORGANISM: Mouse

<400> SEQUENCE: 9

cagattggcc ttgaactggt aag                                    23
```

GAB1 INVOLVEMENT IN GLUCOSE HOMEOSTASIS REGULATION BY HEPATOCYTES

RELATED APPLICATIONS

Benefit of priority under 35 U.S.C. 119(e) is claimed herein to U.S. Provisional Application No.: 60/519,358, filed Nov. 12, 2003. The disclosure of the above referenced application is incorporated by reference in its entirety herein.

GOVERNMENTAL INTEREST

This work was supported by grants GM53660 and HL66208 from the National Institutes of Health. The government may have certain rights in this invention.

STATEMENT REFERENCING A SEQUENCE LISTING SUBMITTED ON COMPACT DISC

The Sequence Listing for this current application is being submitted via compact disc. The content of that submission is incorporated herein by reference. In accordance with 37 CFR §1.52, the relevant information is as follows: The Sequence Listing was created on a PC compatible computer running Windows XP Professional v. 2002. The first document on that disc is titled "Seq.ID.prj" and is a PatentIn project document created with PatentIn 3.3. The PatentIn project document is 150 KB and was created Oct. 28, 2004. The second document on that disc is titled "Seq,ID.ST25.txt" and is a sequence listing document created using the PatentIn 3.3 Generate Sequence Listing function. The sequence listing document is 154 KB; and was created on Oct. 28, 2004. There are included two copies of the Sequence Listing on CD-R.

FIELD OF THE INVENTION

This invention relates to the field of molecular biology and molecular medicine, and more specifically to proteins involved in blood glucose homeostasis and diabetes.

BACKGROUND

In humans, free glucose is present in the plasma and interstitial fluid at a concentration of approximately 80 mg per 100 ml. Blood glucose levels; however, are in a dynamic flux. Organs of the body remove the glucose from the blood for metabolic energy, while food intake loads glucose into the blood system. Under normal conditions, the body maintains a balance of blood glucose by absorbing excess glucose into many tissues.

A rise in blood glucose is normally followed by a rise in blood insulin. Insulin secretion is stimulated by many events associated with glucose intake. Primarily, insulin is secreted by the pancreas. High glucose concentration in the vicinity of the .beta.cells of the pancreas is sensed by the glucose transporter GLUT-2 and is carried into the cells. The glucose is modified and begins a signal transduction cascade that results in insulin exocytosis.

Rising concentrations of insulin in the blood have an effect on three main tissues—liver, muscle and adipose tissue. Liver tissues play a central role in glucose homeostasis primarily orchestrated by insulin (Saltiel, A. R. & Kahn, C. R. Nature 414: 799-806 (2001), Michael, M. D. et al. Mol Cell 6: 87-97 (2000)), although it is not well understood how the insulin-elicited signals are tightly controlled in hepatocytes.

In general, insulin activates a four-subunit transmembrane receptor (insulin receptor) expressed on the surface of these tissue types. The activated insulin receptor phosphorylates and recruits different substrate adaptors such as the Insulin Receptor Substrate (IRS) family of proteins. IRS-1 and IRS-2 proteins are known to be positively required for relay of signals emanating from insulin receptor (Araki, E. et al. Nature 372: 186-90 (1994), Tamemoto, H. et al. Nature 372: 182-6 (1994), Withers, D. J. et al. Nature 391: 900-4 (1998)).

Tyrosine phosphorylated IRS displays binding sites for numerous signaling partners. Among them, PI3K has a role in insulin function mainly characterized by the activation of the Akt/PKB and the PKC.zeta. cascades. These cascades are associated with glucagon synthesis and with glucose uptake. Glucose uptake is mediated by the translocation of glucose transport vesicles to the plasma membrane, which is regulated by numerous signal cascades including those discussed.

Grb2-associated binder 1 (Gab1) is part of a family of adaptor proteins recruited by a wide variety of receptor tyrosine Kinases, such as the insulin receptor. Upon stimulation of the receptor by its cognate ligand, Gab is recruited to the plasma membrane, undergoes phosphorylation and functions as a multi protein assembly center. Gab1 shares structural and functional homology with the IRS family of proteins, possessing a PH domain at the N-terminus, multiple tyrosine phosphorylation sites and proline-rich motifs for entertaining SH2- and SH3-containing proteins (Holgado-Madruga, M., et al. Nature 379: 560-4 (1996), Gu, H. & Neel, B. G Trends Cell Biol 13: 122-30 (2003)). Homozygous Gab1 mutant mice are embryonic-lethal, with the phenotype revealing an essential role of Gab1 in promoting signals from epidermal growth factor (EGF) and hepatocyte growth factor (HGF), etc (Sachs, M. et al. J Cell Biol 150: 1375-84. (2000), Itoh, M. et al. Mol Cell Biol 20: 3695-704 (2000)).

The insulin signalling pathway is critical for the regulation of intracellular and blood glucose levels (glucose homeostasis), and dysregulation of glucose homeostasis is indicated in numerous disorders. For example, diabetes mellitus is a group of diseases characterized by high levels of blood glucose resulting from defects in insulin production, insulin action, or both. There are two main forms of diabetes; type 1 and type 2. Type 1 patients are unable to produce insulin, and thus must receive exogenous insulin to survive. On the other hand, type 2 patients have at least partially preserved insulin production, but often are insulin resistant. Insulin resistance is caused by defects that may arise at the insulin receptor or post-insulin receptor levels. Post-insulin receptor defects often involve signal transduction proteins.

For the year 2003, the Center for Disease Control estimates that 17 million Americans have some type of diabetes, with an increasing prevalence during the last decade resulting in an incidence of about 1 million new cases per year. The prevalence and incidence of diabetes is even higher world wide, making diabetes a global health problem. Diabetes is the sixth leading cause of death in the United States.

The primary treatment for diabetes is the delivery of exogenous insulin via pumps and/or injection. Total annual costs for treating diabetes is $132 billion, with $92 billion attributed to direct medical costs.

Thus, there exists in the art a need to develop novel treatments for managing glucose homeostasis and blood glucose levels. There also exists in the art, a need to prevent the dysregulation of glucose homeostasis and blood glucose levels. Thus, there is a need in the art to better understand the insulin signaling pathway and Gab1.

SUMMARY OF INVENTION

The invention is directed to the regulation of glucose homeostasis by modulating the Grb2-associated binder 1 (Gab1)/MapK (Erk1/2) pathway in hepatocytes. For example, the methods of this invention can include the administration of small molecules, peptides, nucleotides, antisense nucleotides, siRNA, or antibodies to modulate the levels of Gab1, which in turn will modulate the levels of glucose in the blood. More specifically, the administration of small molecules, peptides, nucleotides, antisense nucleotides, siRNA, or antibodies that reduce levels of Gab1, will in turn reduce blood glucose levels.

This invention also provides for a method for identifying compounds capable of modulating the glucose homeostasis regulatory activity associated with the Gab1/MapK pathway.

This invention also provides a method for diagnosing disorders associated with the dysregulation of the glucose homeostasis regulatory activity associated with the Gab1/Erk1/2 pathway.

In one aspect, the invention provides a method for identifying a compound that can effectively modulate glucose homeostasis regulating activity of Gab1 wherein the method includes (a) contacting Gab1 under conditions suitable to promote MapK (e.g., Erk1/2) activation by insulin; (b) measuring the activity of insulin-stimulated MapK; (c) contacting Gab1 with a candidate compound; and (d) determining the ability of the candidate compound to modulate glucose homeostasis , where modulation of insulin-stimulated MapK activity indicates that the candidate compound is an effective compound that modulates glucose homeostasis.

BRIEF DESCRIPTION OF THE DRAWINGS

FIG. 1*a*: Generation of liver-specific Gab1 knockout mice: the targeting strategy. Genomic DNA fragments were cloned into the targeting vector as left, central and right arms. Three loxP sequences were marked by a black triangle (negative: HSV-TK; positive: PGK-NEO). Another negative selection marker, PGK-DT, was put outside of the right arm. The numbered boxes represent exons in the Gab1 gene. TK: thymidine kinase; NEO: neomycin; DT: diphtheria toxin.

FIG. 1*b*: Southern blot analysis. In the upper panel, genomic DNA was digested with BamHI and hybridized to the 32P-labelled 5' probe. Three properly targeted ES cell clones flox/+ (F/+) showed a 6 kb band for the Gab1flox allele and a 10 kb band for the wild-type allele. The lower panel shows a 24 kb band for the wt allele and a 12 kb band for Gab1 flox allele, detected by the 3' probe upon ApaI digestion of genomic DNA.

FIG. 1*c*: PCR with A and B primers on DNA extracted from a Gab1flox/flox mouse (+/+; F/F) and a LGKO mouse. The Gab1flox allele produces a 630 bp fragment and the Gab1-allele produces a 150 bp band. Deletion of the 1oxP-floxed sequences was detected only in the liver (L), but not in the tail (T), skeletal muscle (M), pancreas (P), brown adipose tissue (Ba), white adipose tissue (Wa), hypothalamus (H), pituitary gland (Pi), and kidney (K).

FIG. 1*d*: Immunoblot analysis of Gab1 protein expression in the liver, skeletal muscle, brain and white adipose tissue (Wa) isolated from mice of different genotypes: wild-type (WT), Albumin-Cre/+ (Cre/+), Gab1flox/flox (F/F), Alb-cre/+: Gab1flox/+ (Cre/+, F/+), and LGKO. Gab1 protein was barely detectable in the liver of LGKO mice.

FIG. 1*e*: hnmunoblot analysis of Gab1 expression in liver and skeletal muscle of control (Ctl, Gab1flox/flox) and LGKO mice at the age of 2-month and 1-year, respectively.

(FIG. 2*a*) Fed body weight of control and LGKO mice at the indicated ages and sex, N=19-24 for 2-month-old groups, N=6-25 for 6-month-old groups, N=7 to 19 for 1-year-old groups. (FIG. 2*b*) Fasting body weight of control and LGKO mice at the indicated ages, N=9-14 for 2-month-old groups, N=5-22 for 6-month-old groups, N=7 for each 1-year-old group. M: Male; F: Female.

(PY-IR), normalized against IR.beta. level (IR), in the liver at 0, 2 or 5 min after insulin treatment (N=4). Relative tyrosine phosphorylation of IR.beta. (PY-IR), in skeletal muscle at 0, 4, 8 min of insulin treatment (N=3). Solid bars represent the Control (Ctl) mice and open bars LGKO mice. No statistical significances were found between the two groups using the Student's t test. Values are the means±SEMs.

FIG. 4*c*: Biochemical analysis of insulin signalling in LGKO mice. Upper graph: relative PY levels of IRS-1, -2, in the liver at 0 and 2 min for insulin treatment (N=3). Lower graph: relative amounts of p85.alpha. binding to IRS-1 & -2, in the liver at 0, 2 min of insulin treatment (N=2 to 3). * P<0.05;  P<0.01; * P<0.001 for control versus LGKO. Values are the means±SEMs.

Figure 4B:
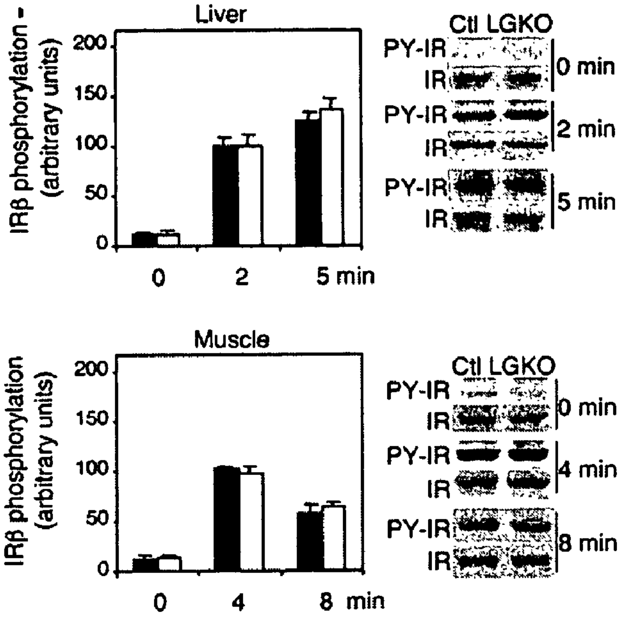
FIG. 4*b*: Insulin-induced tyrosine phosphorylation of IR.beta. in LGKO liver. Left panel is the statistical data of 3-4 experiments using different mice each time, by setting the control value at 2 min to 100. Right panel is a representative immunoblot result. Tyrosine phosphorylation of IR.beta.
Figure 4D:
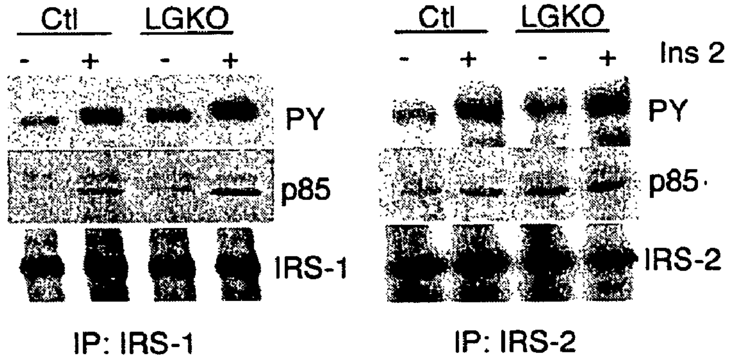
FIG. 4*a*: Biochemical analysis of insulin signalling in LGKO mice. The phosphorylation levels of Akt at Ser473 (p-Akt) were quantified against Akt proteins amounts at different time-points in the liver and muscle. Shown are statistical data collected from 3-4 mice, by setting the value of the control at 2 min to 100, as well as a representative immunoblot. * P<0.05;  P<0.01;* P<0.001 for control versus LGKO. Values are the means±SEMs.

FIG. 4*d*: Deletion of Gab1 leads to enhanced insulin signalling through IRS-1, -2 in hepatocytes. Mice were injected with 5 U insulin (Ins) (+) or saline (−) as a control via vena cava and liver extracts were prepared 2 min after injection. IRS-1 (left panel) or IRS-2 (right panel) were immunoprecipitated from liver lysates with specific antibodies and immunoblotted with antibodies against p85.alpha. subunit of PI3K, phosphotyrosine or against IRS-1, IRS-2 as a loading control.

FIG. 4*e*: Biochemical analysis of insulin signalling in LGKO mice. Tyrosine phosphorylation of Gab1 in the liver were measured 2 min after vena cava injection with 5 U insulin (Ins) (+) or saline (−). Two mice were included in each group. * P<0.05;  P<0.01; * P<0.001 for control versus LGKO. Values are the means±SEMs.

Figure 4F:
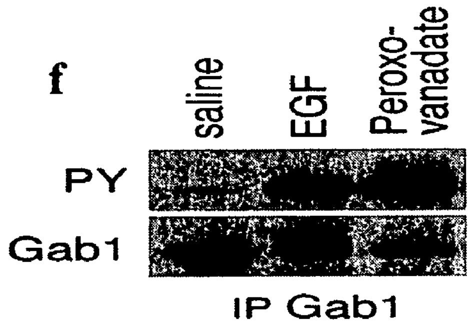

FIG. 4*f*: High levels of Gab1 tyrosine phosphorylation in hepatocytes induced by EGF or peroxovanadate. Tyrosine phosphorylation of Gab1 in the liver was measured 2 min after vena cava injection with EGF or peroxovanadate. Gab1 was immunoprecipitated from liver lysates with Gab1 antibody and immunoblotted with antibodies against phosphotyrosine or Gab1 as a loading control.

FIG. 4*g*: Biochemical analysis of insulin signalling in LGKO mice. Gab1 phosphorylation on the p-YXXM motifs and its association with p85.alpha. in response to saline solution, insulin (Ins), EGF, or peroxovanadate. * P<0.05; ** P<0.01; * P<0.001 for control versus LGKO. Values are the means±SEMs.

FIG. 4*h*: Biochemical analysis of insulin signalling in LGKO mice. Insulin-induced p-Erk1/2 and p-IRS-1S612 were shown together with Erk2 and IRS-1 blots as loading controls. * P<0.05;  P<0.01; * P<0.001 for control versus LGKO. Values are the means±SEMs.

FIG. 4*i*: Biochemical analysis of insulin signalling in LGKO mice. Inhibition of insulin-induced p-Erk1/2 and p-IRS-1S612 by PD98059 MEK inhibitor (left) or U0126 MEK inhibitor (right). * P<0.05;  P<0.01; * P<0.001 for control versus LGKO. Values are the means±SEMs.

Figure 5:
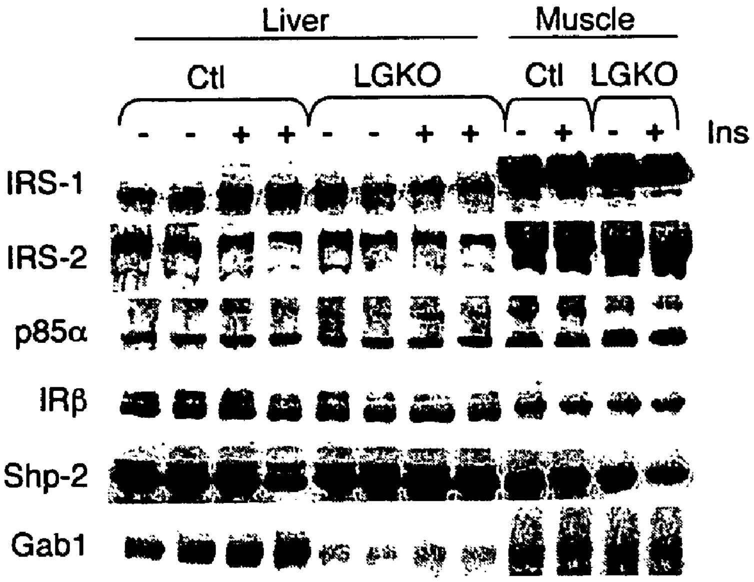

FIG. 5: Normal expression levels of proteins involved in insulin signaling. Immunoblot analysis was performed with lysates from liver or skeletal muscle of control and LGKO mice. Liver and muscle extracts were prepared after saline (−) or insulin (Ins) stimulation for 2 and 4 min, respectively (+). Deletion of Gab1 in the liver did not affect the hepatic expression of IRS-1, IRS-2, p85.alpha., Shp-2 or IR.beta.

Figure 6:
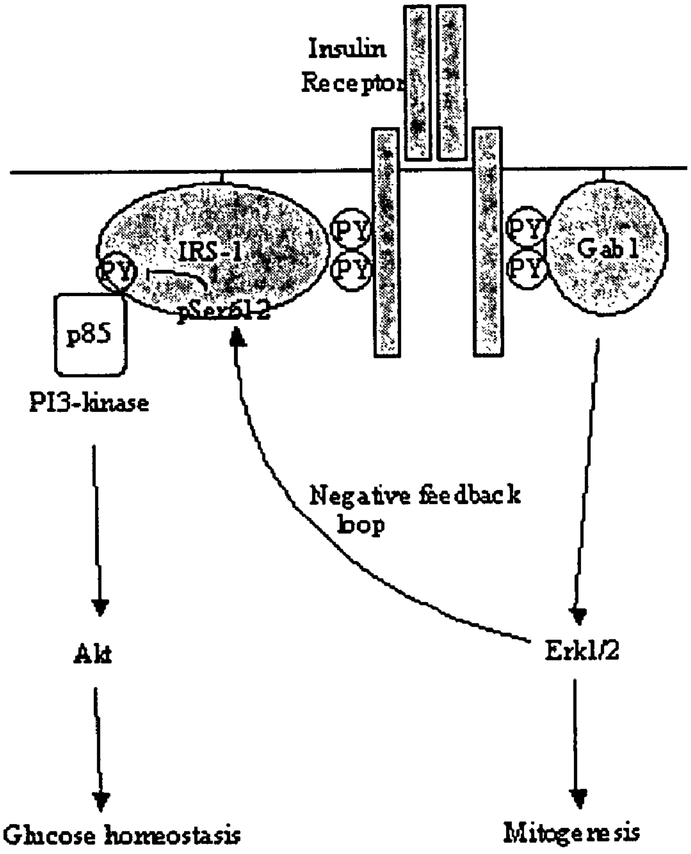

FIG. 6: Inventors model for Gab1 activity (a negative feedback mechanism) in insulin signaling in the liver through the insulin mediated Gab1 protein signaling pathway. Gab1 promotes activation of MapK (Erk), leading to the phosphorylation of the Ser612 residue on IRS-1 and suppressing tyrosine phosphorylation on IRS-1. This, in turn, attenuates insulin-initiated signals flowing through IRS-1/PI3K/Akt pathway.

DETAILED DESCRIPTION OF THE INVENTION

Definitions Used Herein:

The term "site-specific recombination," refers to DNA transfer from a donor DNA or vector to an acceptor DNA or vector.

The term "lox sequence" refers to a nucleotide sequence which undergoes recombination (e.g., DNA cross-over and exchange) when catalyzed by a recombinase, such as Cre, Flp or another member of the Int family of recombinases (Argos et al. (1986) EMBO J. 5: 433). Suitable lox sequences include, for example, the lox sequences recognized by Cre recombinase, and the frt sequences recognized by Flp recombinase.

The term "recombinase" refers to any recombinase capable of catalyzing a site-specific recombination at a lox site. Suitable recombinases include, for example, Cre recombinase (Sauer et al. (1993) Methods in Enzymology 225: 898) and Flp recombinase (Buchholz et al. (1996) Nucl. Acids Res. 24:4256-4262; Buchholz et al. (1998) Nat. Biotechnol. 16:657-662).

The terms "acceptor DNA" and "acceptor vector," are used interchangeably herein and refer to any DNA or vector which, preferably, is capable of integrating into the genome of a cell. For example, the acceptor DNA or vector can be of viral origin, such as a retroviral vector or adeno-associated vector. Generally, the acceptor DNA or vector contains an exchange cassette (i.e., DNA which is replaced by DNA from the donor vector) and can also, optionally, contain a selectable (e.g., negative) marker gene.

The terms "donor DNA" and "donor vector" are used interchangeably herein and refer to any DNA or vector (e.g., circular plasmid DNA) containing DNA which is transferred to the acceptor DNA or vector via a recombinase-mediated exchange reaction. Generally, the donor DNA or vector comprises plasmid DNA and, optionally, also can contain a selectable (e.g., positive) marker gene.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422-428 (1998); Tietze et al., Curr. Biol., 2:363-371 (1998); Sofia, Mol. Divers. 3:75-94 (1998); Eichler et al., Med. Res. Rev. 15:481-496 (1995); and the like. Libraries containing large numbers of natural and synthetic compounds also can be obtained from commercial sources.

The number of different candidate compounds to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about 103, 105 or 107 different compounds, which can be assayed simultaneously or sequentially.

The present invention relates to the discovery that Gab1 protein is a negative regulator of the glucose homeostasis pathway. In the current discovery, Inventors have shown that when Gab1 is knocked-out in the liver in mammals, the mammal will display hypoglycemia and enhanced glucose tolerance. Inventors' showing leads to the discovery that Gab1 promotes action in the MapK (Erk) pathway, which in turn downregulates the IRS pathway, leading to hypoglycemia and enhanced glucose tolerance.

To determine how Gab1 functions in glucose homeostasis, Inventors generated a mouse model in which the Gab1 gene was specifically disrupted in the liver. Methods for generating a knock out mouse are generally well known in the art. (Brown, T. A., Gene Cloning and DNA Analysis, Ed. 4, Blackwell Science Press (2001)). Liver-specific Gab1 knockout (LGKO) mice were created to possess a conditional Gab1 knockout allele, a loxp-floxed allele of Gab1 (Gab1.sup.flox). Two loxP sites were inserted into introns flanking exon 3 of the Gab1 gene using homologous recombination in embryonic stem (ES) cells (FIG. 1*a*). Methods and techniques for achieving efficient and stable site-specific DNA recombination using a recombinase/lox system, such as the Cre/lox system or the Flp/frt system, are well known in the art.

Genomic DNA fragments of Gab1 were isolated by screening a .lambda.DASHII mouse genomic library, (Stratagene, La Jolla Calif.), with a Gab1 cDNA fragment as a probe. The sequence of Gab1 is known and presented in a variety of databases, including Project Ensembl from The Wellcome Trust Sanger Institute. The Mouse Gab1 gene is listed herein as SEQ ID No.: 1. Similarly, the cDNA probe is listed herein as SEQ ID No.: 2, and is generated from a partial sequence of SEQ ID No.: 1. Based on the restriction map, (determined using the Flash Non-Radioactive Gene Mapping Kit, Stratagene, La Jolla Calif.), and partial sequencing of Gab1 genomic DNA fragments, a targeting construct was engineered using a triple-loxP construction system, wherein the genomic DNA fragments were cloned into the targeting vector as left, central and right arms. (See e.g., Jr-Wen Shui and Tse-Hua Tan, Genesis, 39:3, p217. See also, Wang, Xinhe, et al., PNAS, 99:26, 16881; and Zhu, Y.J. et al. Journal of Bio. Chem. 278 (3): 1986-1990; and Gainetdinov, R. R. et al., Neuron, 24, 1029 (1999); and Gainetdinov, R. R. et al., Neuron, 38, 291 (2003)). The Gab1 gene and the target construct are homologously recombined, resulting in three loxP sequences flanking the central arm and the negative/positive selection marker genes (negative: HSV-TK; positive: PGK-NEO), allowing for cell selection. (Dr. R. T. Premont (Duke University, Durham, N.C.) provided the triple-loxp vectors. See also Gainetdinov, R. R. et al., Neuron, 24, 1029 (1999); and Gainetdinov, R. R. et al., Neuron, 38, 291 (2003)). Another negative selection marker, PGK-DT, was put outside of the right arm. Exon 3 codes for amino acids 124-198 of the Gab1 protein and deletion of this exon leads to a frame-shift mutation and to the introduction of a new stop codon immediately. Exon 3 nucleic acids are listed at SEQ ID No.: 3. The recombinant construct DNA is then linearized using NotI (NEB, Inc., Beverly Mass., Catalog No.: R0189S) and introduced into R1 ES cells using electroporation.

ES cell colonies resistant to the Geneticin Antibiotic G418 (Sigma, St. Louis, Mo., Cat No.: G-9516) were screened for homologous recombination by PCR using a primer in the neo cassette and a primer outside of the right arm. The Gab1.sup.flox allele and the Gab1 knockout (Gab1-) allele can be distinguished by PCR analysis using primers A (SEQ ID No.: 4) and B (SEQ ID No.: 5) that produces DNA fragments at 670 bp and 200 bp, respectively. Results were confirmed using Southern Blot analysis with a 5' probe (Southern Blot techniques are well known in the art. See for example, Maniatis et al., Molecular Cloning: A Laboratory Manual (1989), 2nd Ed., Cold Spring Harbor, N.Y.) (FIG. 1*b*). Briefly, genomic DNA was digested with ApaI or BamHI and hybridized to the .sup.32P-labelled 3' probe or 5' probe. Three properly targeted clones (F/+) show one 6 kb band for the Gab1.sup.flox allele and another 10 kb band for the wild-type allele. The lower panel of FIG. 1*b* shows a 24 kb band for the wild-type allele and 12 kb for Gab1.sup.flox allele, detected by the 3' probe upon ApaI digestion of genomic DNA. Gene Targeting techniques are well known to those of ordinary skill in the art, and are described in the literature. (See e.g., Joyner, A., Gene Targeting: A Practical Approach, The Practical Approach Series, edited by B. D. Hames, Oxford University Press $2^{nd}$ Ed., Oxford 1999.)

ES cells were then transiently transfected with a CMV-Cre construct (pBS185; Invitrogen Corp., Carlsbad, Calif.). Cells containing the CMV-cre construct were selected in fialuridine (FIAU)-containing medium against the TK-neo cassette. (FIAU, Moravek Biochemicals, Brea Calif., Cat. No. M-251.) Surviving clones were further screened by PCR analysis using primers A and B (SEQ ID No.: 4 and SEQ ID No.: 5, respectively), described above, thereby allowing for isolation of ES cell clones with a loxP-floxed Gab1 allele (Gab1.sub.flox). The engineered ES cells were injected into C57BL/6 blastocysts and chimeric animals were obtained. Germline transmission of the Gab1.sub.flox allele was obtained from two independent ES cell clones isolated from the screen.

Generation of liver-specific Gab1 knockout (LGKO) mice:

The Gab1.sup.flox allele was generated in a 129/Sv background and mutant mice were crossed with wild-type C57BL/6 animals for 4 generations to acquire the C57BL/6 background. To generate liver-specific Gab1 knockout (LGKO) mice, Gab1.sup.flox/+ mice were crossed with Albumin-Cre transgenic mice (C57BL/6-TgN (Alb-cre) 21Mgn). (See e.g., Michael, et al. *Mol Cell* 6: 87-97 (2000); and Postic et al., J Biol Chem 274, 305-15 (1999)). LGKO mice (Gab1.sup.flox/flox:Alb-cre/+) were born with the expected Mendelian frequency, morphologically indistinguishable from their wild-type (WT) littermates. All animals were housed in virus-free facility on a 12 hr light/dark cycle and were fed with a standard mouse food. All protocols for animal use and euthanasia were approved by the institutional animal committee.

To determine the efficiency of exon 3 deletion in the bred mice, PCR analysis was performed on genomic DNA extracted from the tails and liver of weaned mice. Genotyping PCR used the following primers: Cre primers GCC TGC ATT ACC GGT CGA TGC AAC GA, (SEQ ID No.: 6) GTG GCA GAT GGC GCG GCA ACA CCA TT (SEQ ID No.: 7) and Gab1.sup.Flox/wild-type primers: GGT GAA TCG ACG GGT GCT TGT GA, (SEQ ID No.: 8) CAG ATT GGC CTT GAA CTG GTA AG (SEQ ID No.: 9). The PCR program used was: 94° C. for 5 min; 39 cycles at 94° C. for 30 s, 58° C. for 30 s, 72° C. for 45 s; 72° C. for 5 min. PCR analysis of the LGKO mice showed an efficient deletion of exon 3 in the liver but not other organs such as skeletal muscles, pancreas, brown and white adipose tissue, hypothalamus, pituitary and kidney. (FIG. 1*c*).

The efficiency of Gab1 deletion in LGKO hepatocytes was further demonstrated by immunoblot analysis.

Male mice at age of 2 month were fasted for 16 hr and were anaesthetized intraperitoneally with Avertin (0.015 ml/g) (2,2,2 tribromoethanol, purchased at Aldrich Cat. No.: T4,840.2). Either 5 U of human insulin (Humalin, Eli Lilly & Company) or 20 microliters saline solution was injected into the inferior vena cava. Liver and muscle tissue were harvested as indicated above, and quickly frozen in liquid nitrogen.

Frozen liver and muscle samples were homogenized in a Dounce apparatus in Protein lysis buffer (50 mM Hepes pH7.5, 150 mM NaCl, 10% glycerol, 1% Triton X-100, 1 mM EGTA, 100 mM NaF, 10 mM sodium pyrophosphate, 10 mM Na3VO4, 10 micrograms/ml leupeptin, 10 ug/ml aprotinin, 2 mM PMSF). After 30 min incubation on ice, tissue lysates were clarified by centrifugation at 37,000 g for 1 hr at 4° C. Protein concentration was determined using a kit from Bio-Rad (Bio-Rad Protein Assay, Hercules, Calif., Catalogue No.: 500-0001).

For immunoprecipitation, 1.5 mg of total protein was incubated with 4-5 μl antibody for 2-4 hr at 4° C. and the mixture was further incubated for 2-4 hr at 4° C. with protein A/G plus agarose (Santa-Cruz Biotechnology, Santa Cruz, Calif., Cat No.: sc-2003). The bead-bound complex was washed three times with cold HNTG buffer (20 mM Hepes, pH7.5, 150 mM NaCl, 10% glycerol, 0.1% Triton X-100) and resuspended in 10 μl SDS sample buffer. For immunoblot analysis, lysates were separated on SDS-polyacrylamide gels, transferred to a nitrocellulose membrane, and blotted with primary antibodies as indicated. Specific signals were detected by enhanced chemiluminescence (ECL analysis kit; Amersham Corp.) following blotting with horseradish peroxidase-conjugated secondary antibodies. Antibody against Gab1 was produced by injection of rabbits with purified glutathione S-transferase fusion protein of Gab1 following standard procedures. Antibodies to phospho-Akt (serine 473), Akt, phospho-p44/42 Erk, Phospho-(Tyr) p85 of PI3K, phospho-IRS-1 (Ser612) were obtained from Cell Signaling Technologies (Beverly Mass.). Antibodies to p85.alpha., p110.alpha., IR.beta., Erk1/2 were obtained from Santa Cruz Biotechnology (Santa Cruz, Calif.). Anti-phosphotyrosine antibody was purchased from Upstate Biotechnology Inc. (Charlottesville, Va.). IRS-1 and IRS-2 antibodies were kindly provided by Joslin Diabetes Center, Boston, Mass., and are further available from Upstate—Cell Signaling Solutions (Charlottesville, Va., Catalog Nos.: 06-248 and 06-506). Those of skill in the art will readily prepare antibodies to an antigen using well known techniques (See e.g., Harlow, Ed, Lane, David, Antibodies: A Laboratory Manual, 1988, Cold Springs Harbor Press). Blots were scanned and signals were quantified using IMAGEQUANT.sup.™ software. Statistical analysis of the data was performed using a two-tailed unpaired t-test, expressing values as mean±SEM.

Figures 2A, 2B:
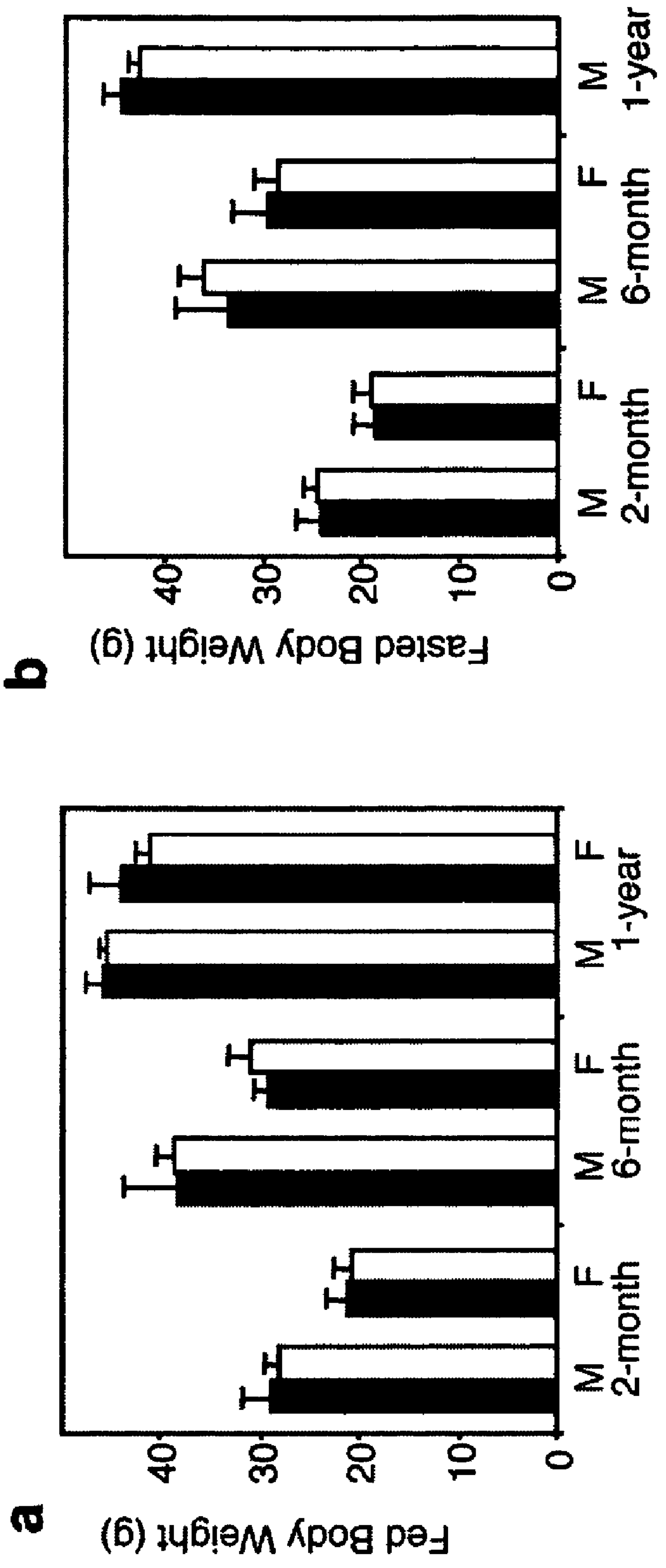
FIGS. 2*a* and 2*b*: Body weights of LGKO mice. Solid bars are for the control and open bars for LGKO mice. No statistically significant difference was observed between the two groups using the Student's t test analysis. Values are the means ±SEM.

As seen in FIG. 1*d*, the efficiency of Gab1 deletion was higher than 90% in LGKO liver, but Gab1 expression was not changed in skeletal muscle, brain or white adipose tissue. Gab1 protein was barely detectable in the liver of LGKO mice (Gab1.sup.flox/flox Alb-Cre/+), but Gab1 expression was not changed in the liver of Gab1.sup.+/+:+/+ (wt); Gab1.sup.+/+: Alb-Cre/+ (Cre/+); Gab1.sup.flox/flox:+/+ (F/F); Gab1.sup.flox/+:Alb-cre/+ (Cre/+, F/+) mice. Stable deletion of Gab1 was detected in young adult mice (2 months) as well as in aged 1-year old mice (FIG. 1*e*). Deletion of Gab1; however, did not affect normal development and morphology of the liver. The ratio of liver versus body weight of mutant mice was normal (WT: 5.21±0.22%, N=6; LGKO: 5.23±0.13%, N=9). The body weight for mutant mice was also similar to the wild-type over a one-year period in both fed and fasted mice. (FIGS. 2*a* and 2*b*).

Glucose Homeostasis and LGKO Mice:

To determine the effects of the Gab1 knockout on glucose homeostasis a series of metabolic and biochemical studies were performed.

Figures 3A, 3B, 3C:
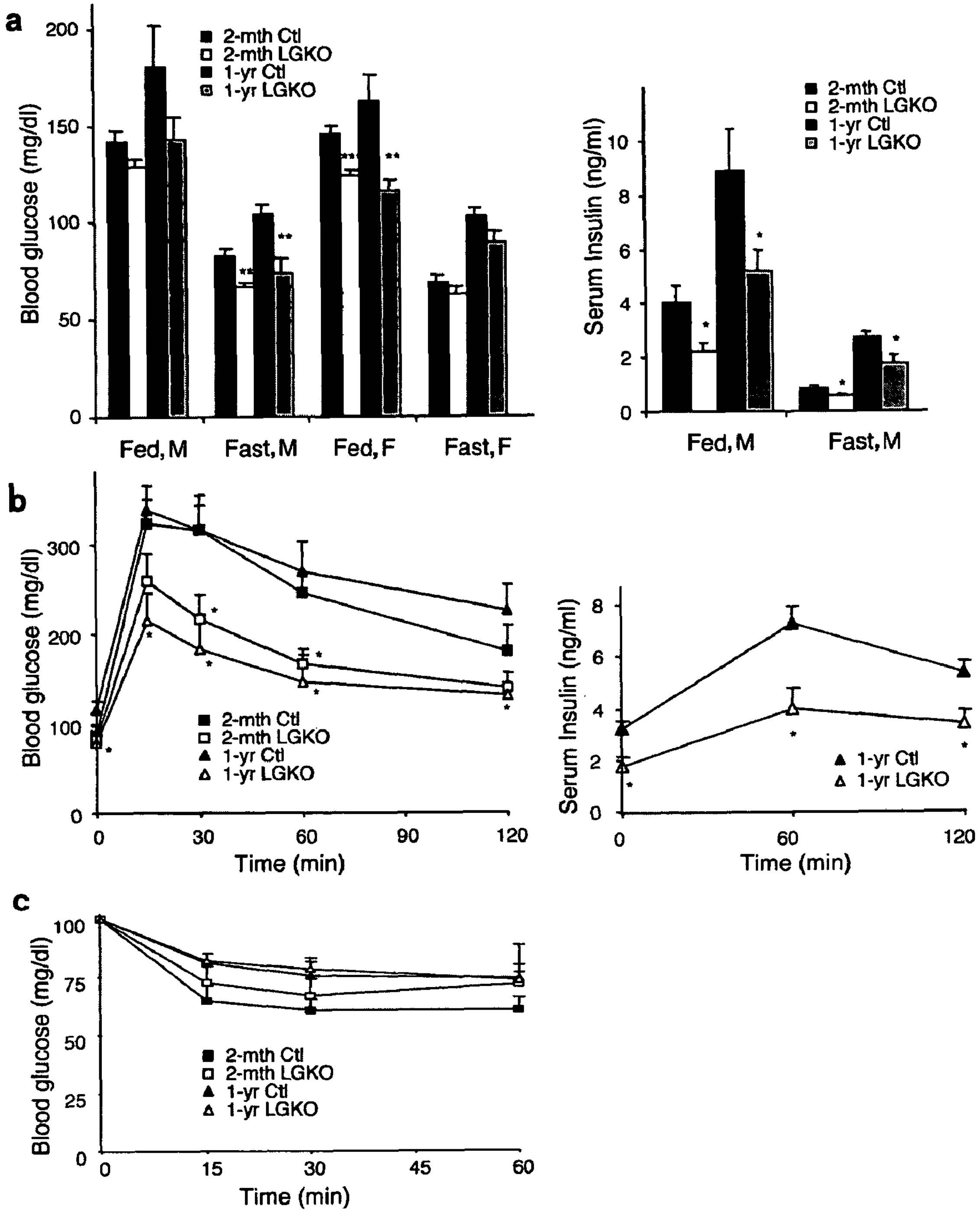
FIG. 3*a*. Metabolic changes of LGKO mice. Blood glucose levels were measured on randomly-fed (Fed) or 16-hr fasted (Fast) male (M) or female (F) mice; N=8 to 39 for each group. Serum insulin levels were measured on fed and fasted male mice; N=10 to 13 for each group. * P<0.05;  P<0.01; * P<0.001 for control versus LGKO. Values are the means±SEMs.
FIG. 3*b*. Metabolic changes of LGKO mice. Blood glucose and serum insulin during glucose tolerance test performed on 16-hr-fasted male mice; N=5 to 8 for each group. * P<0.05;  P<0.01; * P<0.001 for control versus LGKO. Values are the means±SEMs.
FIG. 3*c*. Metabolic changes of LGKO mice. Blood glucose level during insulin tolerance test performed on randomly-fed male animals; N=6 to 10 per group. * P<0.05;  P<0.01; * P<0.001 for control versus LGKO. Values are the means±SEMs.

Blood glucose levels of both WT and LGKO mice were measured using whole venous blood and an automatic glucose monitor (e.g., One Touch Basic, Lifescan, Milpitas, Calif.). Surprisingly, the results of these studies revealed that LGKO animals are hypoglycaemic under both fed and fasted status when blood glucose levels are measured on sex- and age-matched mice (FIG. 3*a*). Selective deletion of hepatic Gab1 led to reduced blood glucose levels, ranged from 9.1 to 28.9%, in comparison between both fed and fasted states for gender- and age-matched mice (FIG. 3*a*). For example, in comparison to control mice, the blood glucose concentrations in fasted male LGKO mice at the age of 2-month and 1-year were reduced by 19% (P=0.006) and 28.9% (P=0.009), respectively. Significant decrease of blood glucose levels was also detected in fed female LGKO animals (FIG. 3*a*). Consistently, serum insulin levels in fed and fasted LGKO male mice were significantly lower than control littermates when measured at 2-month (Fed: P=0.0192; Fasted: P=0.0275) or 1-year (Fed: P=0.0356; Fasted: P=0.0171) (FIG. 3*a*). This result strongly suggests a negative regulatory role of Gab1 in insulin-controlled glucose homeostasis.

To further determine the role of Gab1 in glucose homeostasis, Inventors performed a glucose tolerance test (GTT). Glucose tolerance tests were performed intravenously (IGTT), although the test can be performed orally (OGTT). In the current discovery, mice were fasted for 16 hours, and then given a solution containing a known amount of glucose via intra-peritoneal (IP) injection (2 g glucose per 1 kg body weight). Blood was obtained before IP injection of the glucose solution (time point 0), and was drawn again at 15, 30, 60 and 120 min (time point 15, 30, 60 and 120, respectively). Following intraperitoneal glucose injection, LGKO mice exhibited significantly reduced plasma glucose levels for each of the sampling time-points during the 120-minute glucose tolerance test, GTT (FIG. 3*b*); and thus the area under the glucose curve was significantly decreased (72% of control at 2-month; 59% at 1 year) for LGKO animals as compared to controls. In addition, the insulin response to the glucose load, measured at 60 and 120 min during the GTT, was significantly diminished in LGKO animals, with a decrease in the area under the curve by 44% (FIG. 3*b*). Thus, selective deletion of hepatic Gab1 significantly improved glucose tolerance. In addition, the lower glucose response curve, in spite of significantly diminished insulin levels, also implicates enhanced insulin sensitivity.

To assess the potential difference in peripheral glucose disposal between the genotypes of mice, we first performed in vivo insulin tolerance tests. Insulin tolerance tests (ITT) were performed on randomly fed animals via IP delivery of a bolus of insulin (1 U insulin per kg of body weight), (Humulin, Eli Lilly and Company, Indianapolis, Ind. 46285). Blood glucose levels were measured at time point 0, 15, 30 and 60 minutes after intra-peritoneal injection of human insulin using Lifescan's One Touch system. Serum insulin levels were measured by ELISA, using rat insulin as a standard (Cat#: INSKR 020, Crystal Chem. Inc. Downers Grove, Ill. 60515). Serum triglyceride levels were measured by Animal Care Program, Diagnostic Laboratory, University of California, San Diego. As seen in FIG. 3*c*, insulin's ability to reduce circulating glucose levels was similar between the genotypes at both ages. Since the insulin tolerance test is a relatively crude technique for assessment of insulin stimulated glucose disposal, the more accurate glucose clamp technique was used to quantitatively assess overall in vivo insulin action, quantify the rates of glucose disposal and hepatic glucose production.

Briefly, at 1 year of age each mouse was implanted with two catheters in the right jugular vein which were tunneled subcutaneously, exteriorized at the back of the neck, and encased in silastic tubing. Four days after surgery, animals were fasted for 6 hours and glucose turnover was measured in the basal state and during a hyperinsulinemic-euglycemic clamp. Following basal sampling (approximately 90 min), a constant infusion (5.micro.Ci/h) of [3-3H] D-glucose (NEN Life Science Products Inc.) was infused into one of the jugular cannulas. One hour after the start of the tracer infusion, a second basal blood sample was taken for measurement of glucose concentration and tracer specific activity as previously described 28. Following this, regular human insulin (12 mU. kg-1. min-1, Novolin R; Novo Nordisk Pharmaceutical Industries Inc.) combined with [3-3H] D-glucose (5.micro.Ci/h) was infused. Steady state was achieved by 80 minutes and held for the duration of the 120 minutes clamp. Following the steady state period (minimal of 30 minutes) at the end of the clamp, a final blood sample was taken for measurement of glucose turnover. Plasma glucose concentration was measured with a HemoCue glucose analyzer (Hemocue Inc., Lake Forrest, Calif. 92630). Circulating plasma human insulin following the clamp was measured using a radioimmunoassay kit (Linco Research, St. Charles, Mo. 63304, RIA Kit, Catalog No.: MENDO-75K). Plasma glucose specific activity was measured after deproteinization with barium hydroxide and zinc sulfate as previously described by our laboratory. Hepatic glucose production (HGP) and glucose disposal rate (GDR) were calculated at basal and during the 30-minute steady state portion of the glucose clamp. Tracer determined rates were quantified using the Steele equation for steady state conditions. Comparisons between the two groups were conducted using analysis variance (ANOVA), and values were presented as means±SEMs. Clamp techniques are well know in the art. (Miles, P. D., Barak, Y., He, W., Evans, R. M. & Olefsky, J. M. Improved insulin-sensitivity in mice heterozygous for PPAR-gamma deficiency. J Clin Invest 105, 287-92 (2000); Revers, R. R., Fink, R., Griffin, J., Olefsky, J. M. & Kolterman, O. G. Influence of hyperglycemia on insulin's in vivo effects in type II diabetes. J Clin Invest 73, 664-72 (1984); Steele, R. Influences of glucose loading and of injected insulin on hepatic glucose output. Ann N Y Acad Sci 82, 420-30 (1959).)

Figures 3D, 3E, 3F, 3G:
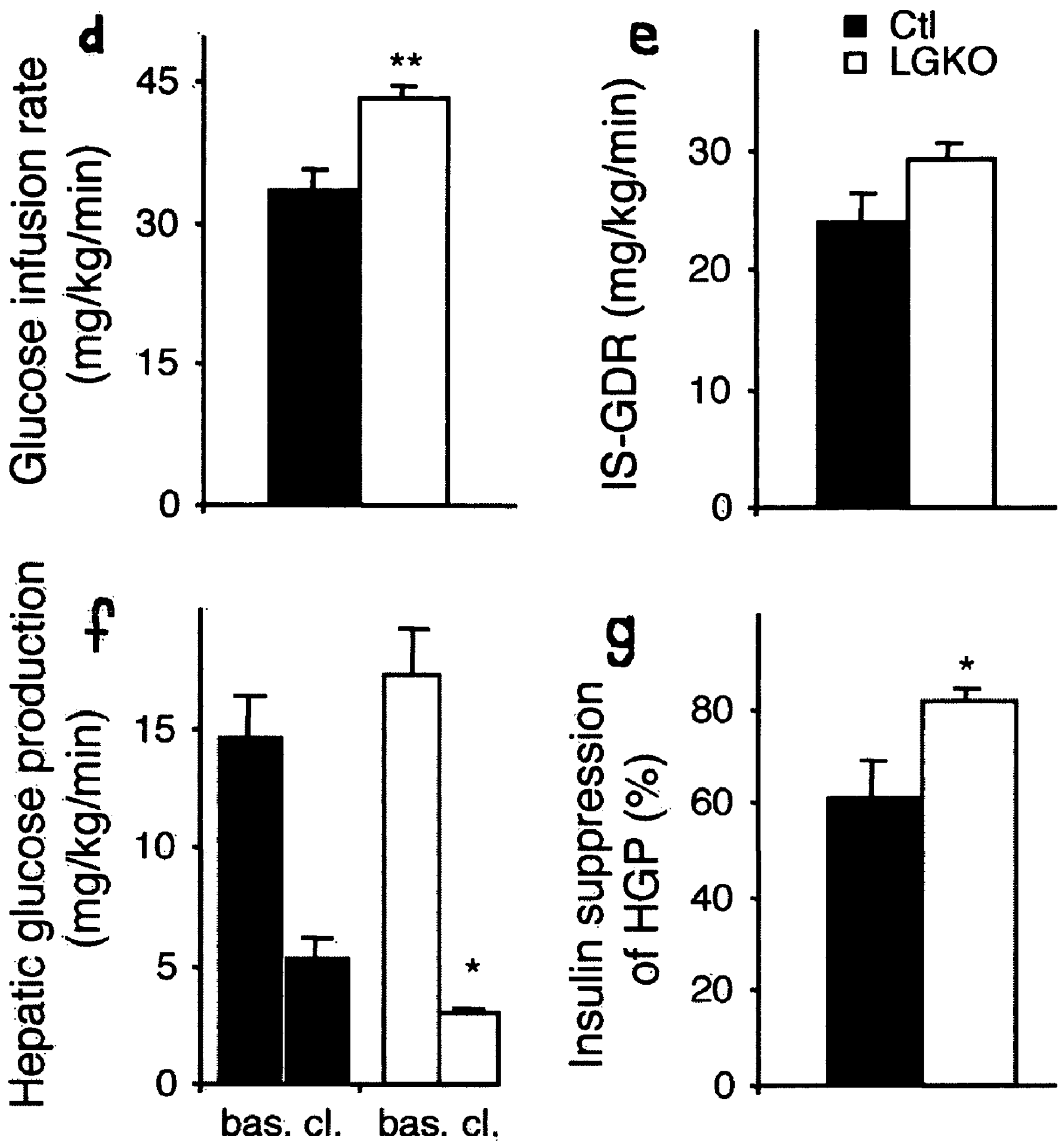
FIG. 3*d*: In vivo insulin sensitivity measured by Glucose infusion rate. One-year-old male mice were used, N=8. * P<0.05; ** P<0.01 for control versus LGKO. Values are the means±SEMs.
FIG. 3*e*: In vivo insulin sensitivity measured by IS-GDR at the infusion rate of 12 mU/kg/min. One-year-old male mice were used, N=8. * P<0.05; ** P<0.01 for control versus LGKO. Values are the means±SEMs.
FIG. 3*f*: In vivo insulin sensitivity measured by basal (bas.) and clamped (cl.) hepatic glucose productions (HGP). One-year-old male mice were used, N=8. * P<0.05; ** P<0.01 for control versus LGKO. Values are the means±SEMs.
FIG. 3*g*: In vivo insulin sensitivity measured by insulin suppression of HGP, as determined by euglycemic, hyperinsulinemic clamp analyses. One-year-old male mice were used, N=8. * P<0.05; ** P<0.01 for control versus LGKO. Values are the means±SEMs.

Both groups of animals were clamped at the 6-h fasting blood glucose values, 125±2.4 mg/dl. The exogenous glucose infusion rate (GIR) required to maintain euglycemia during the glucose clamp was increased by ~30% (P=0.0016) in LGKO mice (FIG. 3*d*). Similar to results for the insulin tolerance test (FIG. 3*c*), no significant difference was observed between the genotypes with respect to insulin's ability to stimulate glucose disposal into skeletal muscle (IS-GDR, FIG. 3*e*). However, we did detect more marked suppression of hepatic glucose production (HGP) from basal during the clamp in LGKO mice (FIGS. 3*f* and 3*g*), revealing enhanced hepatic insulin sensitivity.

Figure 3H:
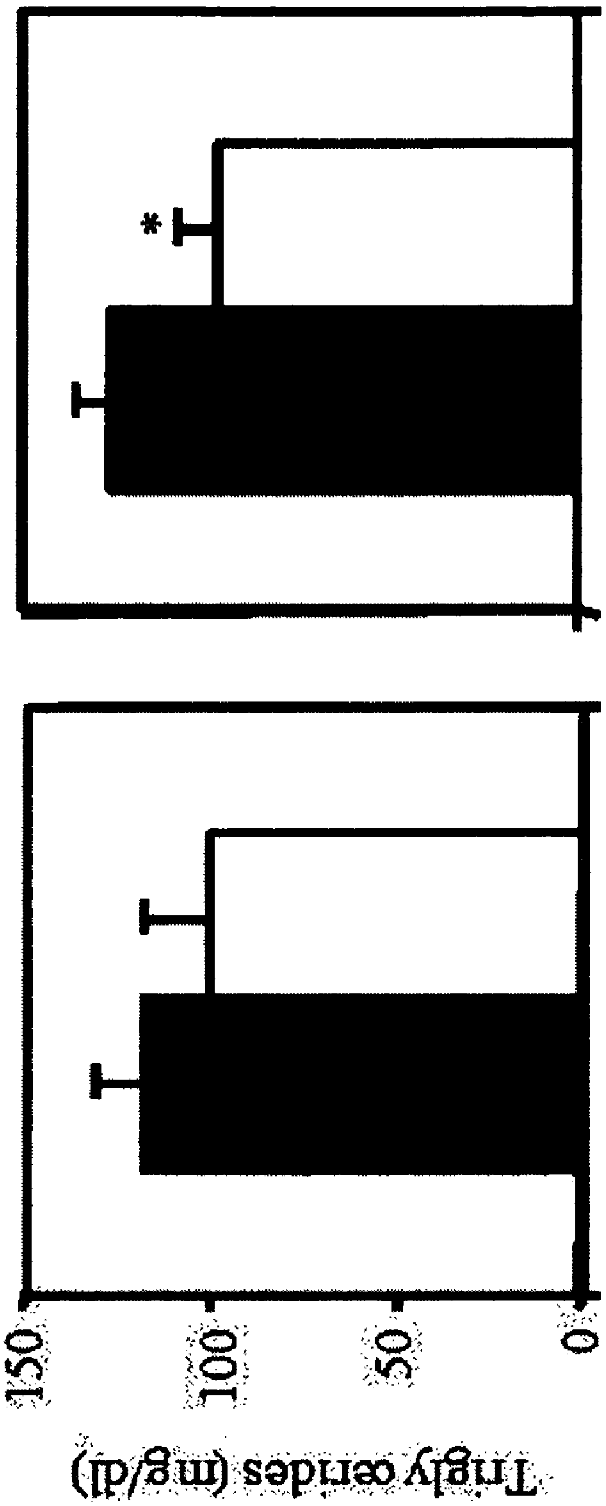
FIG. 3*h*: Serum triglyceride levels were measured for 16 hr-fasted mice (N=8, for 2-month-old mice; N=12-13 for 1-year-old animals). Solid bars represent the control mice and open bars and squares represent the LGKO mice. * P<0.05;  P<0.01; * P<0.001 for control versus LGKO, Student's t tests. Values are the mean±SEM.

Glucose is converted to fat in the liver, and triglycerides are released in blood by the liver. The amount of fasting triglycerides was slightly lower for both the 2-month-old (14.8% reduction) and 1-year-old (22.7% reduction) knockout mice (FIG. 3*h*). At 2-months-old, the difference was not significant (P=0.41), whereas at one-year-old of age, the difference was statistically significant (P<0.05). Thus, Gab1 deletion in the liver also changed hepatic lipid metabolism.

Inventors' have discovered that hypoglycemia and enhanced glucose tolerance in LGKO is related to the Gab1 actions in the liver. Gab1 promotes the Erk pathway in attenuating insulin-elicited signals through the IRS signalling pathway. Thus, Gab1 deficiency in hepatocytes removes Gab1 mediated attenuation of IRS, resulting in increased basal and insulin-stimulated Akt/PKB activity.

To investigate the molecular basis for hypoglycemia and improved glucose tolerance, we examined the activity of Akt/PKB kinase, a critical enzyme in insulin signaling, by measuring levels of phospho-Akt (p-Akt) in both liver and muscle of wild-type and LGKO mice. Tissue lysates were made from the liver at 0, 2 and 5 min after insulin administration, and muscle lysates were prepared at 0, 4 and 8 min following insulin injection (FIG. 4*a*), and lysates were detected using immunoblot techniques as described hereinabove. Both basal and insulin-stimulated levels of p-Akt were higher in LGKO liver than that in wild-type, without a change in protein expression levels of Akt. Notably, elevated Akt activity was detected in the LGKO liver only, with no difference observed in skeletal muscle. Immunoblot and other techniques for measuring the level of protein in tissue samples are well known in the art.

Inventors measured the tyrosine phosphorylation status of the beta subunit of insulin receptor (IR.beta.) and observed its normal activation in LGKO liver as well as in muscle (FIGS. 4*b* and 4*c*). The IR.beta. expression level was not changed either (FIG. 5). Therefore, the increased Akt activity can not be attributed to a change in IR.beta. activation or expression but is rather caused by a downstream event.

Inventors then examined the protein amounts of IRS-1, IRS-2, Shp-2, and the p85.alpha. subunit of PI3-kinase in both liver and muscle, and found no change in their expression in LGKO mice (FIG. 5). However, using antibodies specific for the phosphorylated form of IRS-1 or IRS-2, Inventors discovered that enhanced tyrosine phosphorylation levels of both IRS-1 and IRS-2 were detected in the LGKO liver with or without insulin stimulation (FIGS. 4*c* and 4*d*). IRS-1 tyrosine phosphorylation was the most affected, with a 2.0 fold increase at the basal level and a 1.4 fold increase after insulin stimulation, whereas it was about 1.4 fold improved at both conditions for IRS-2. Consistently, higher amounts of p85 were detected in complex with IRS-1 and IRS-2 in Gab1-deficient hepatocytes, under both control and insulin-stimulated status (FIGS. 4*c* and 4*d*). Thus, Gab1 acts to attenuate insulin-triggered signals going through both IRS-1 and IRS-2, and deletion of Gab1 in the liver leads to augmented activation of the IRS proteins, which results in promotion of the PI3K/Akt pathway. The binding of IRS-1, -2 to IR.beta. is not affected by Gab1 deletion (FIG. 4*d*), excluding the possibility of a competition between IRS and Gab1 for binding IR.beta.. Unlike the IRS proteins, Gab1 is weakly tyrosine-phosphorylated following insulin stimulation (FIGS. 4*e*, 4*f* and 4*g*), despite high levels of Gab1 phosphorylation being detected following induction by injection of EGF or peroxo-vanadate (an agent known to induce tyrosine phosphorylation). Neither phosphorylation of the p85 binding motif on Gab1 (p-YXXM), nor association of Gab1 with p85 was detected in insulin treated liver (FIG. 4*g*), suggesting that Gab1 may not be found directly involved in insulin stimulated pI3K/Akt pathway. Instead it appears that Gab1 has a negative effect on insulin stimulated IRS activation and thus deletion of Gab1 in the liver leads to augmented IRS tyrosine phosphorylation. This observation is contrary to what would be expected if Gab1 was directly involved in modulation of PI3K/Akt pathway in response to insulin.

Those of ordinary skill in the art are familiar with a variety of techniques for detecting phosphorylation of an amino acid residue within a protein or peptide fragment. Briefly, and by way of example only, wild-type mice were injected via vena cava with a saline solution (control), insulin (5 U), EGF (100 μg), or peroxo-vanadate. Liver extracts were prepared 2 min after injection; immunoprecipitated with Gab1 antibody; and immunoblotted with antibodies against either phospho-tyrosine (PY), Gab1, phospho-(Tyr) p85 PI3K (p-YXXM), or p85. Peroxo-vanadate solution was prepared following a procedure published previously (S. J. Ruff, K. Chen, S. Cohen, *J Biol Chem* 272, 1263-7 (Jan. 10, 1997)).

Vena cava injection of insulin dramatically induced the activation of extracellular signal-regulated kinase (Erk) in the liver in vivo (FIG. 4*h*). However, the insulin-stimulated Erk activity was abolished in Gab1 deficient hepatocytes (FIG. 4*h*). This result suggests that Gab1, rather than IRS protein, plays a critical role in mediating insulin-stimulated activation of the Erk pathway in hepatocytes. It was previously reported that serine phosphorylation of IRS-1 by Erk down regulated its tyrosine phosphorylation and association with p85 ((Mothe, I. & Van Obberghen, E. *J Biol Chem* 271: 11222-7 (1996), De Fea, K. & Roth, R. A. *Biochemistry* 36: 12939-47 (1997), De Fea, K. & Roth, R. A. *J Biol Chem* 272: 31400-6 (1997)). Using an antibody specific for phospho-serine 612 (p-IRS-1.sup.S612), Inventor detected insulin-induced phosphorylation of IRS-1 on this amino acid residue, a known negative regulatory site on IRS-1 for insulin signaling (De Fea, K. & Roth, R. A. *Biochemistry* 36, 12939-47 (1997)). Notably, this serine-phosphorylation event was abolished in Gab1-deficient hepatocytes (FIG. 4*h*). Consistently, injection of MEK inhibitors (PD98059 or U0126. Cell Signaling Technologies, Beverly, Mass., Cat. Nos.: 9900S and 9903, respectively) also attenuated Erk activation as well as phosphorylation of IRS-1 on Ser612 (FIG. 4*i*).

Inventors have discovered and herein disclosed that Gab1 is the primary mediator for insulin-stimulated Erk activation, which leads to serine phosphorylation of IRS-1 and attenuation of its tyrosine phosphorylation. This, in turn, results in down-regulation of the IRS/PI3K/Akt pathway. This negative feedback loop in hepatocytes is a critical molecular mechanism for glucose homeostasis, as controlled by insulin (FIG. 6). Interestingly, the negative regulatory role of Gab1 in glucose metabolism is connected with its positive effect in mediating cell mitogenesis via the Erk pathway. Thus, pharmaceutical interference of the Gab1 activity in insulin signaling not only reduces blood glucose levels but also may suppress unwanted mitogenic activities in the liver.

Dysregulation of the glucose homeostasis pathway can lead to numerous disorders ranging from altered blood pressure to diabetes. Diabetes mellitus is the most common public health problem worldwide, affecting over 5% of the population in western countries. Ninety-five percent (95%) of the cases are classified as type II or non-insulin-dependent diabetes mellitus, which results from resistance to insulin activity (Kahn, B. B. & Rossetti, L. *Nat Genet* 20, 223-5 (1998), Taylor, S. I. *Cell* 97, 9-12 (1999)). To this end, search for negative regulators of the glucose homeostasis pathway is of particular interests in development of therapeutic strategies for related diseases.

Through Inventor's novel discovery of the Gab1 signalling pathway, Gab1 presents as an attractive target for addressing these goals. The negative regulatory role of Gab1 in glucose homeostasis is connected with its positive effect in mediating cell mitogenesis via the Erk pathway. Disruption of the Gab1 activity in insulin signalling may not only reduce blood glucose level but also may suppress unwanted mitogenic activities in the liver, thereby preventing hepatic carcinogenesis.

Thus, Inventors have uncovered a novel balancing mechanism for control of insulin signal strength in liver via the actions of Gab1. Inventors' discovery leads to a novel method for discovering new therapeutic modulators for treating type II diabetes mellitus, and other regulatory disorders of the glucose homeostasis pathway. Inventors' discovery also leads to a novel method for diagnosing the origin of disorders related to glucose homeostasis dysregulation, and developing specific treatments therefore.

EXAMPLES

While the present invention has been described in some detail for purposes of clarity and understanding, one skilled in the art will appreciate that various changes in form and detail can be made without departing from the true scope of the invention.

High Throughput Screening techniques are well known in the art and applicable to methods using Inventors' discovery. The number of different candidate compounds used to test in the methods of the invention will depend on the application of the method. For example, one or a small number of candidate compounds can be advantageous in manual screening procedures, or when it is desired to compare efficacy among several predicted ligands, agonists or antagonists. However, it is generally understood that the larger the number of candidate compounds, the greater the likelihood of identifying a compound having the desired activity in a screening assay. Additionally, large numbers of compounds can be processed in high-throughput automated screening assays. Therefore, "one or more candidate compounds" can be, for example, 2 or more, such as 5, 10, 15, 20, 50 or 100 or more different compounds, such as greater than about 103, 105 or 107 different compounds, which can be assayed simultaneously or sequentially The following non-limiting examples are useful in describing Inventor's discovery, and are in no way meant to limit the current invention. Those of ordinary skill in the art will readily adopt the underlying principles of Inventor's discovery to design a variety of screening assays without departing from the spirit of the current invention.

Screening Assay One

A first screening assay takes advantage of the methods and procedures described above. In this example, LGKO and WT mice are generated using the previously described procedures. Blood glucose levels, Glucose tolerance tests and Insulin tolerance tests are performed at time point 0, as described. The mice are then given a bolus of glucose. The control group comprises both WT mice and the LGKO mice, which receive the bolus of glucose alone. Similarly, the test group comprises WT and the LGKO mice; however, the test group receives a bolus of glucose and one or more candidate compounds. A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods. Candidate compounds can be given concurrently with the bolus of glucose or at a time point before or after the administration of said bolus of glucose. The Blood glucose levels, Glucose tolerance tests and Insulin tolerance tests are again performed, this time at time points 15, 30, 60 and 120, as described.

Measurements received from the control group establish baseline glucose levels, glucose tolerance and baseline insulin tolerance. As described above, there is a difference in the blood glucose levels and in glucose tolerance, but not insulin tolerance, between the WT and LGKO mice, thus the control group will establish data parameters for mice with functional Gab1 and with a knockout Gab1.

The test group will receive a glucose bolus and one or more candidate compounds. Each candidate compound will be tested in WT and LGKO mice. Candidate compounds that modulate the glucose homeostasis pathway are useful in treating the conditions associated with dysregulation of said glucose homeostasis pathway. For example, LGKO mice receiving a candidate compound that increases blood glucose levels reveal an ideal candidate modulator for treating hypoglycemia. Similarly, WT mice receiving a candidate compound that decreases blood glucose levels reveal an ideal candidate modulator for treating hyperglycemia. Glucose tolerance modulators are also discovered using this screening method.

Those of skill in the art will readily use Inventor's disclosure and will design numerous animal models to screen candidate compounds for modulators of the glucose homeostasis pathway. Such uses are all within the spirit of the current invention.

Screening Assay Two

In a second example, test agents are screened to see if said test agent is capable of modulating Gab1 mediated Erk1/2 activity. Those of ordinary skill in the art will readily uncover this same information using a variety of methods; however, in this example hepatic cell lines containing the Gab1 mediated glucose homeostasis pathway are used.

Briefly, hepatic cells are plated in a multi-well cell culture plate containing 96 wells, 384 wells, 1594 or other commercially available well numbers, and are incubated according to well known procedure. Otherwise identical wells are then either exposed to one or more candidate compounds in a glucose solution (test wells) or are exposed to glucose solution alone (control wells). A candidate compound can be a naturally occurring macromolecule, such as a polypeptide, amino acid, nucleic acid, carbohydrate, lipid, or any combination thereof. A candidate compound also can be a partially or completely synthetic derivative, analog or mimetic of such a macromolecule, or a small organic molecule prepared by combinatorial chemistry methods.

The wells are immediately and incrementally assayed for glucose concentration. In this situation, the response of the test cell to a candidate compound is compared to the response (or lack of response) of the control cell to the same compound under substantially the same reaction conditions. Candidate compounds that reduce the level of glucose in the test well as compared to the control are considered to negatively modulate Gab1 mediated Erk1/2 activity, thereby leading to a hypoglycemic environment. Conversely, candidate compounds that result in a higher level of glucose in the test well as compared to the control are considered to positively modulate Gab1 mediated Erk1/2 activity, thereby leading to a hyperglycemic environment.

Candidate compounds shown to modulate Gab1 mediated Erk1/2 activity are useful in treating the conditions associated with dysregulation of the glucose homeostasis pathway.

Screening Assay Three

In an alternative embodiment of Screening Assay Two, hepatic cell lines comprise either a wild type Gab1 or a Gab1 knockout. In this embodiment, the assay is performed as is Screening Assay Two: cells are plated in wells; the wells are exposed to glucose alone (control well) or glucose and one or more candidate compounds (test wells); and subsequent glucose concentration data is acquired.

In this embodiment, the control wells present data for the Gab1 mediated glucose homeostasis pathway wherein either Gab1 is functional or wherein Gab1 is knocked out. Candidate compounds that cause a decrease in glucose concentration in the wild type wells function to modulate the Gab1 mediated glucose homeostasis pathway in a manner similar to when Gab1 is knocked out. These modulators are useful for treating hyperglycemia. Conversely, candidate compounds that cause an increase in glucose concentration in the LGKO wells function to modulate the Gab1 mediated glucose homeostasis pathway in a manner similar to when Gab1 is functionally present.

Screening Assay Four

In a fourth example, candidate compounds are screened to determine whether said candidate compound is capable of modulating Gab1 wherein said screening method includes (a) contacting Gab1 under conditions suitable to promote MapK activation by insulin; (b) measuring the activity of insulin-stimulated MapK; (c) contacting Gab1 with a candidate compound; and (d) determining the ability of the candidate compound to modulate glucose homeostasis, where modulation of insulin-stimulated MapK activity indicates that the candidate compound is an effective compound that modulates glucose homeostasis.

For example, such a screening method can include a hepatic cell line comprising the Gab1 signaling pathway. The hepatocytes are plated in a cell culture well under suitable conditions. Such cell culture wells may be part of a multi-well plate having 96-wells, 384-wells or any number of wells commercially available. Those of skill in the art will readily adapt the current example to high throughput screening. Such applications are anticipated by the current disclosure.

The wells are designated as either negative control (cell media only); positive control (cell media and insulin) or test wells type A (cell media, insulin and candidate compound) and test wells type B (cell media and candidate compound). The cells are incubated under suitable conditions along with negative control media, positive control media, type A media or type B media. Following incubation, the cells are lysed at the optimal time and the extracts are assayed for MapK (Erk1/2) activity using immunoblot techniques. An antibody specific for phospho serine 612 of IRS-1 is used to detect insulin mediated activity of Erk1/2 t. In short, wells are stained for IRS-1 phosphorylation using p-IRS-1.sup.Ser612 antibodies followed by Cy3 conjugated anti-goat IgG (Cell Signaling Technologies, Beverly, Mass.). Fluorescent images can be collected and analyzed using, for example, MRC-1024 MP laser-scanning confocal microscope, and the images then compared.

The phosphorylation of IRS-1 in the presence of a candidate compound is compared to the control wells. Data acquired from the control wells establishes the degree of Gab1 mediated glucose homeostasis pathway activity in the presence and absence of insulin. Data from the test wells can be compared to the control wells. Candidate compounds causing an increase or decrease in insulin mediated activity of Erk1/2, as compared to control wells, determined by relative levels of phosphorylation at Ser612 residue of IRS-1, are useful as modulators of the Gab1 mediated glucose homeostasis pathway. Furthermore, the action of these modulators is further elucidated in that those that activate the Gab1 pathway in the absence of insulin are useful for treating insulin production and/or release mediated disorders, while those that act in the presence of insulin are useful for disorder occurring despite the presence of insulin. Modulators that increase IRS-1 phosphorylation are useful for treating hypoglycemia, while those that reduce IRS-1 phosphorylation are useful for treating hyperglycemia.

Diagonostic Assay

The current invention is additionally useful in diagnosing whether a dysregulation of the glucose homeostasis pathway is related to the Gab1 signaling pathway. For example, using the technique described in Screening Assay Two, hepatic cells obtained from the liver biopsy of a patient suffering from a disorder related to glucose homeostasis dysregulation can be assayed.

Biopsied hepatic cells are plated in a cell culture plate, which may be multi well containing 96 wells, 384 wells, 1594 wells or other commercially available well numbers, and are incubated according to well known procedure. Otherwise identical wells are then either exposed to Gab1 modulators in a glucose solution (test wells) or are exposed to glucose solution alone (control wells). Gab1 modulators, as used in this Diagnostic Assay, are those that have been identified to restore glucose homeostasis in LGKO mice, or other Gab1 deficient systems.

The wells are immediately and incrementally assayed for glucose concentration. In this situation, the response of the test cell to the modulator is compared to the response in the control cell under substantially the same reaction conditions. If the Gab1 modulator causes a restoration of glucose homeostasis in said test cell, then the diagnosis and subsequent treatments can be tailored to treating a Gab1 deficiency.

Pharmaceutical Compositions

Methods of using the compounds and pharmaceutical compositions of the invention are also provided herein. The methods involve both in vitro and in vivo uses of the compounds and pharmaceutical compositions for altering preferred nuclear receptor activity, in a cell type specific fashion.

In certain embodiments, the claimed methods involve the discovery and use of modulating compounds including agonists, antagonists, ligands, small molecules, peptides and nucleic acid molecules.

Once identified as a modulator using a method of the current invention, an agent can be put in a pharmaceutically acceptable formulation, such as those described in Remington's Pharmaceutical Sciences, 18th ed., Mack Publishing Co., Easton, Pa. (1990), incorporated by reference herein, to generate a pharmaceutical composition useful for specific treatment of diseases and pathological conditions.

Agents identified by the methods taught herein can be administered to a patient either by themselves, or in pharmaceutical compositions where it is mixed with suitable carriers or excipient(s). In treating a patient exhibiting a disorder of interest, a therapeutically effective amount of agent or agents such as these is administered. A therapeutically effective dose refers to that amount of the agent resulting in amelioration of symptoms or a prolongation of survival in a patient.

The agents also can be prepared as pharmaceutically acceptable salts. Examples of pharmaceutically acceptable salts include, but are not limited to acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the agent is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the agent, for example, to increase the solubility of the agent. Examples of carriers and excipients include calcium carbonate, calcium phosphate, various sugars or types of starch, cellulose derivatives, gelatin, vegetable oils, polyethylene glycols and physiologically compatible solvents.

For applications that require the compounds and compositions to cross the blood-brain barrier, or to cross the cell membrane, formulations that increase the lipophilicity of the compound are particularly desirable. For example, the compounds of the invention can be incorporated into liposomes (Gregoriadis, Liposome Technology, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer. Additionally, the therapeutic compound can be conjugated to a peptide that facilitates cell entry, such as penetratin (also known as Antennapedia peptide), other homeodomain sequences, or the HIV protein Tat.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Agents which exhibit large therapeutic indices are preferred. The data obtained from these cell culture assays and animal studies can be used in formulating a range of dosage for use in humans. The dosage of such agents lies preferably within a range of circulating concentrations that include the ED50 with little or no toxicity. The dosage may vary within this range depending upon the dosage form employed and the route of administration utilized.

For any agent identified by the methods taught herein, the therapeutically effective dose can be estimated initially from cell culture assays. For example, a dose can be formulated in animal models to achieve a circulating plasma concentration range that includes the IC50 as determined in cell culture (i.e., the concentration of the test agent which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in The Pharmacological Basis of Therapeutics, Ch. 1 p. 1 (1975)). It should be noted that the attending physician would know how to and when to terminate, interrupt, or adjust administration due to toxicity, or to organ dysfinctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the agents herein disclosed into dosages suitable for systemic administration is contemplated. With proper choice of carrier and suitable manufacturing practice, these agents, in particular, those formulated as solutions, may be administered parenterally, such as by intravenous injection. The agents can be formulated readily using pharmaceutically acceptable carriers well known in the art into dosages suitable for oral administration. Such carriers enable the agents of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the context of the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active agents into preparations which can be used pharmaceutically. The preparations formulated for oral administration may be in the form of tablets, dragees, capsules, or solutions. The pharmaceutical compositions contemplated by the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active agents in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the agents to allow for the preparation of highly concentrated solutions.

Pharmaceutical preparations for oral use can be obtained by combining the active agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

We claim:

1. A method of identifying modulators of the glucose homeostasis pathway, that act on the Gab1 protein signaling pathway comprising the steps of:

(a) obtaining a system comprising a control group and a test group, wherein the control group and the test group comprise one set of cells expressing Gab1 protein and another set of cells not expressing Gab1 protein;

(b) exposing the control group to a solution of glucose and the test group to a solution of glucose and one or more candidate compounds, wherein the candidate compound is not insulin;

(c) measuring the glucose levels of the control group and the test group;

(d) comparing the glucose levels of the control group to the glucose levels of the test group; and (e) identifying whether the one or more candidate compounds are modulators of the Gab1 protein signaling pathway, wherein a difference in the glucose levels between the cells expressing Gab1 protein and the cells not expressing Gab1 protein in the test group indicates that the candidate compound is a modulator of the glucose homeostasis pathway.

2. The method of claim 1, wherein the system is a mammalian system.

3. The method of claim 2, wherein the mammalian system is murine.

4. The method of claim 3, wherein the mammalian system is a knockout mouse.

5. The method of claim 2, wherein the mammalian system is a hepatic cell line.

6. The method of claim 1, wherein the system comprises an endogenous insulin mediated Gab1 protein signaling pathway.

7. The method of claim 6, wherein the endogenous insulin mediated Gab1 protein signaling pathway has a dysfunctional Gab1 protein.

8. The method of claim 1, wherein the candidate compound is selected from the group consisting of: a peptide, polypeptide, peptidomimetic, carbohydrate, lipid, an antibody or antibody fragment, and a nucleotide sequence.

9. The method of claim 8, wherein the candidate compound modulates the insulin mediated Gab1 protein signaling pathway.

10. The method of claim 9, wherein the candidate compound modulates activity of MapK within the insulin mediated Gab1 protein signaling pathway.

11. The method of claim 8, wherein the candidate compound modulates glucose homeostasis via the insulin mediated Gab1 protein signaling pathway.

12. The method of claim 1, wherein the steps (b), (c), (d) or (e) are performed by high-throughput screening.

13. The method of claim 1, wherein an increase in glucose levels in the test cells not expressing Gab1 compared to the glucose levels in the test cells expressing Gab1 indicates that the candidate compound positively modulates the glucose homeostasis pathway.

14. The method of claim 1, wherein a decrease in glucose levels in the test cells not expressing Gab1 compared to the glucose levels in the test cells expressing Gab1 indicates that the candidate compound negatively modulates the glucose homeostasis pathway.

15. A method of identifying candidate compounds capable of positively modulating a Gab1 mediated glucose homeostasis pathway, comprising the steps of:

(a) obtaining, a system comprising cells which express Gab1 protein and cells which do not express Gab1 protein:

(b) exposing the cells in the system to a glucose solution:

(c) exposing the cells in the system of (b) to one or more candidate compounds;

(d) measuring glucose levels in the system in the presence of one or more candidate compounds:

(e) comparing the glucose levels of the system;

(f) identifying those candidate compounds which have a measurable effect on glucose levels of the cells which express Gab1 protein when compared to the cells which do not express Gab1 protein; and (g) an increase in glucose levels in the cells not expressing Gab1 protein compared to the glucose levels in the cells expressing Gab1 protein indicates that the candidate compound positively modulates the Gab1 mediated glucose homeostasis pathway.

16. A method of identifying candidate compounds capable of negatively modulating, a Gab1 mediated glucose homeostasis pathway, comprising the steps of:

(a) obtaining a system comprising cells which express Gab1 protein and cells which do not express Gab1 protein;

(b) exposing the cells in the s stem to a glucose solution;

(c) exposing the cells in the system of (b) to one or more candidate compounds (d) measuring glucose levels in the system in the presence of one or more candidate compounds;

(e) comparing the glucose levels of the system;

(f) identifying those candidate compounds which have a measurable effect on glucose levels of the cells which express Gab1 protein when compared to the cells which do not express Gab1 protein; and (g) a decrease in glucose levels in the cells not expressing Gab1 compared to the glucose levels in the cells expressing Gab1 indicates that the candidate compound negatively modulates the Gab1 mediated glucose homeostasis pathway.

* * * * *